(12) United States Patent
Sakai et al.

(10) Patent No.: US 6,207,652 B1
(45) Date of Patent: Mar. 27, 2001

(54) APOPTOSIS INDUCERS

(75) Inventors: Takeshi Sakai; Hideo Kitano; Fu-Gong Yu; Shinji Nakayama; Kaoru Kojima; Hitomi Kimura; Yoshikuni Nakanishi; Kaoru Katayama, all of Hirosaki; Takanari Tominaga, Otsu; Kazuo Shimanaka, Otsu; Katsushige Ikai, Otsu; Ikunoshin Kato, Hirosaki, all of (JP)

(73) Assignees: Takara Shuzo Co., Ltd., Kyoto; Research Institute for Glycotechnology, Aomori, both of (JP)

( * ) Notice: Subject to any disclaimer, the term of this patent is extended or adjusted under 35 U.S.C. 154(b) by 0 days.

(21) Appl. No.: 09/051,284

(22) PCT Filed: Jan. 21, 1997

(86) PCT No.: PCT/JP97/00116

§ 371 Date: Apr. 9, 1998

§ 102(e) Date: Apr. 9, 1998

(87) PCT Pub. No.: WO97/26896

PCT Pub. Date: Jul. 31, 1997

(30) Foreign Application Priority Data

| Jan. 26, 1996 | (JP) | ................................................ 8-031187 |
| Feb. 8, 1996 | (JP) | ................................................ 8-045583 |
| Feb. 8, 1996 | (JP) | ................................................ 8-045593 |
| Jun. 12, 1996 | (JP) | ................................................ 8-171658 |
| Jul. 16, 1996 | (JP) | ................................................ 8-204187 |

(51) Int. Cl.$^7$ .......................... A61K 31/715; C07H 15/00
(52) U.S. Cl. .................. 514/54; 514/25; 514/61; 536/4.1; 536/18.5; 536/118; 536/122; 536/123.1; 536/124
(58) Field of Search .................... 536/4.1, 18.5, 536/118, 122, 123.1, 124; 514/25, 54, 61

(56) References Cited

FOREIGN PATENT DOCUMENTS

| 2217746 | * | 10/1996 | (CA) . |
| 4-91027 | | 3/1992 | (JP) . |
| 8-000266 | * | 1/1996 | (JP) . |

OTHER PUBLICATIONS

Nishino et al. Carbohydrate Research 1994, 25S, 213–224, month not available.*

* cited by examiner

Primary Examiner—Kathleen K. Fonda
(74) Attorney, Agent, or Firm—Wenderoth, Lind & Ponack, L.L.P.

(57) ABSTRACT

Apoptosis inducers, anticancer drugs and carcinostatic drugs containing sulfated-fucose-containing polysaccharide(s) and/or degradation product(s) thereof, and a method for inducing apoptosis by using sulfated-fucose-containing polysaccharide(s) and/or degradation product(s) thereof as the active ingredient. A degrading enzyme which is useful in the production of the degradation products of sulfated-fucose-containing polysaccharides.

21 Claims, 33 Drawing Sheets

SIGNAL INTENSITY

SIGNAL INTENSITY

APOPTOSIS INDUCERS

This application is a national stage of international application no. PCT/JP97/00116 filed Jan. 21, 1997.

BACKGROUND OF THE INVENTION

1. Field of the Invention

This invention relates to apoptosis inducers, anticancer drugs and carcinostatic drugs which are usable as medicines. It further provides a method for inducing apoptosis which is useful in, for example, clarifying the mechanism of apoptosis and screening apoptosis induction inhibitors. Furthermore, it provides purified sulfated-fucose-containing polysaccharides and degradation products thereof and a sulfated-fucose-containing polysaccharide degrading enzyme which is useful in producing sulfated-fucose-containing polysaccharide degradation products and studying the structures thereof.

2. Description of the Related Art

In recent years, the style of apoptosis (self-destructive cell death or suicidal cell death) has attracted attention regarding the death of cell tissues.

It is considered that apoptosis is the death inherently programmed in genes, different from necrosis meaning pathological cell death. Namely, some external or internal factors trigger the activation of genes programming apoptosis. On the basis of this genes, a programmed death gene protein is subsequently biosynthesized and decomposed the cells per se, thus causing death.

It is highly meaningful to express the apoptosis in a desired tissue or cells, if possible, since unnecessary or pathogenic cells can be spontaneously eliminated from the living body thereby.

The present invention aims at developing highly safe compounds having effects of inducing apoptosis and thus providing apoptosis inducers, anticancer drugs and carcinostatic drugs containing these compounds and a method for inducing apoptosis by using these compounds as the active ingredient. The present invention further aims at providing an enzyme capable of degrading the compounds of the present invention which is useful in the production of the degradation products of these compounds.

SUMMARY OF THE INVENTION

In summary, the first invention of the present invention relates to apoptosis inducers which contain sulfated-fucose-containing polysaccharide(s) and/or degradation product(s) thereof.

The second invention of the present invention relates to a method for inducing apoptosis which comprises using as the active ingredient sulfated-fucose-containing polysaccharide(s) and/or degradation product(s) thereof.

The third invention of the present invention relates to anticancer drugs containing sulfated-fucose-containing polysaccharide(s) and/or degradation product(s) thereof of the fifth or sixth invention of the present invention.

The fourth invention of the present invention relates to carcinostatic drugs containing sulfated-fucose-containing polysaccharide(s) and/or degradation product(s) thereof.

The fifth invention of the present invention relates to sulfated-fucose-containing polysaccharides having the following physicochemical properties:

(1) constituting saccharide: containing uronic acid; and (2) being degraded by the fucoidanase produced by Flavobacterium sp. SA-0082 (FERM BP-5402) to thereby form at least one of the compounds selected from those represented by the following formulae (I), (II) and (III):

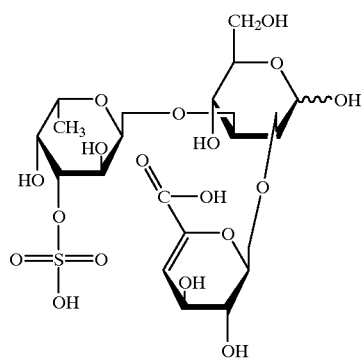

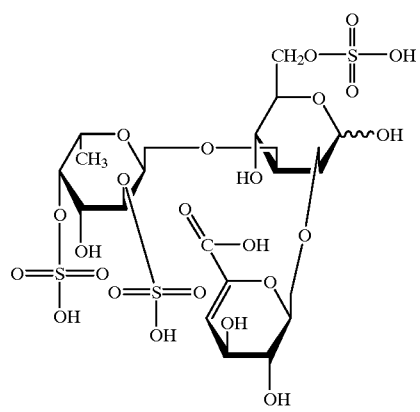

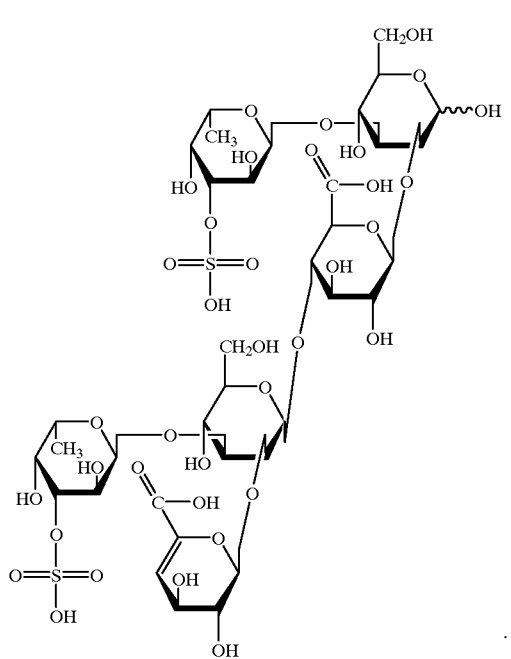

The sixth invention of the present invention relates to sulfated-fucose-containing polysaccharides having the following physicochemical properties:

(1) constituting saccharide: substantially being free from uronic acid; and (2) substantially incapable of being degraded by the fucoidanase produced by Flavobacterium sp. SA-0082 (FERM BP-5402).

The seventh invention of the present invention relates to a process for producing sulfated-fucose-containing polysaccharides of the fifth invention of the present invention which involves the step of treating a mixture of sulfated-fucose-containing polysaccharides with a chemical capable of aggregating acidic polysaccharides in the presence of salts and eliminating the precipitate.

The eighth invention of the present invention relates to a process for producing sulfated-fucose-containing polysaccharides of the fifth invention of the present invention which involves the step of treating a mixture of sulfated-fucose-containing polysaccharides with an anion exchange resin in the presence of a divalent cation to thereby take up the target polysaccharides.

The ninth invention of the present invention relates to a process for producing sulfated-fucose-containing polysaccharides of the fifth invention of the present invention which involves, in the process of producing the sulfated-fucose-containing polysaccharides of the fifth invention of the present invention, the step of eliminating the coexisting coloring matters by using a polysaccharide substance or a substance having an anion exchange group.

The tenth invention of the present invention relates to a process for producing sulfated-fucose-containing polysaccharides of the sixth invention of the present invention which involves the step of treating a mixture of sulfated-fucose-containing polysaccharides with a degrading enzyme capable of degrading sulfated-fucose-containing polysaccharides containing uronic acid or a microorganism having this enzyme to thereby take up the target sulfated-fucose-containing polysaccharides.

The eleventh invention of the present invention relates to a process for producing sulfated-fucose-containing polysaccharides of the sixth invention of the present invention which involves the step of treating a mixture of sulfated-fucose-containing polysaccharides with a chemical capable of aggregating acidic polysaccharides in the presence of salts to thereby precipitate the target polysaccharides.

The twelfth invention of the present invention relates to a process for producing sulfated-fucose-containing polysaccharides of the sixth invention of the present invention which involves the step of treating a mixture of sulfated-fucose-containing polysaccharides with an anion exchange resin in the presence of a divalent cation to thereby take up the target polysaccharides.

The thirteenth invention of the present invention relates to a process for producing sulfated-fucose-containing polysaccharides of the sixth invention of the present invention which involves, in the process of producing the sulfated-fucose-containing polysaccharides of the sixth invention of the present invention, the step of eliminating the coexisting coloring matters by using a polysaccharide substance or a substance having an anion exchange group.

The fourteenth invention of the present invention relates to a process for producing a sulfated-fucose-containing polysaccharide mixture which comprises effecting the extraction of sulfated-fucose-containing polysaccharide mixtures to be used in the seventh, eighth, tenth, eleventh or twelfth invention of the present invention from marine algae in the coexistence of acetate and calcium ions.

The fifteenth invention of the present invention relates to an endo-sulfated-fucose-containing polysaccharide degrading enzyme having the following physicochemical properties:

(i) function: acting on sulfated-fucose-containing polysaccharides having the following physicochemical properties and degrading the sulfated-fucose-containing polysaccharides:
  (a) constituting saccharide: substantially being free from uronic acid; and
  (b) substantially incapable of being degraded by the fucoidanase produced by Flavobacterium sp. SA-0082 (FERM BP-5402);
  but not acting on sulfated-fucose-containing polysaccharides having the following physicochemical properties:
  (c) constituting saccharide: containing uronic acid; and
  (d) being degraded by the fucoidanase produced by Flavobacterium sp. SA-0082 (FERM BP-5402) to thereby form at least one of the compounds selected from those represented by the following formulae (I), (II) and (III):

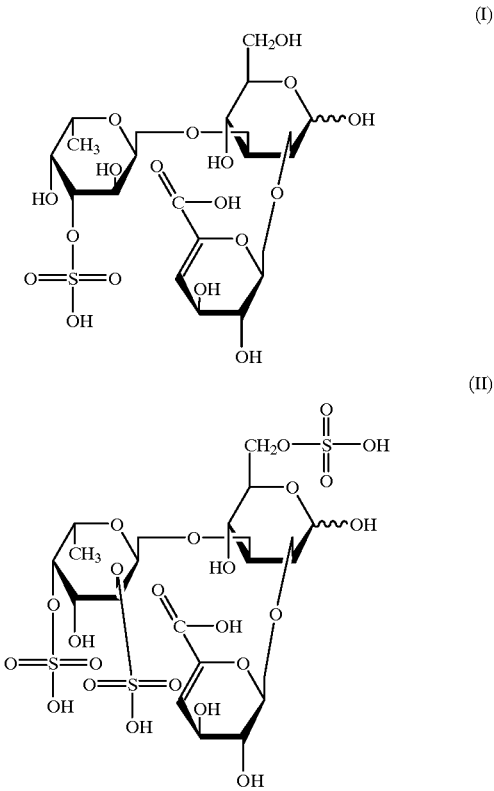

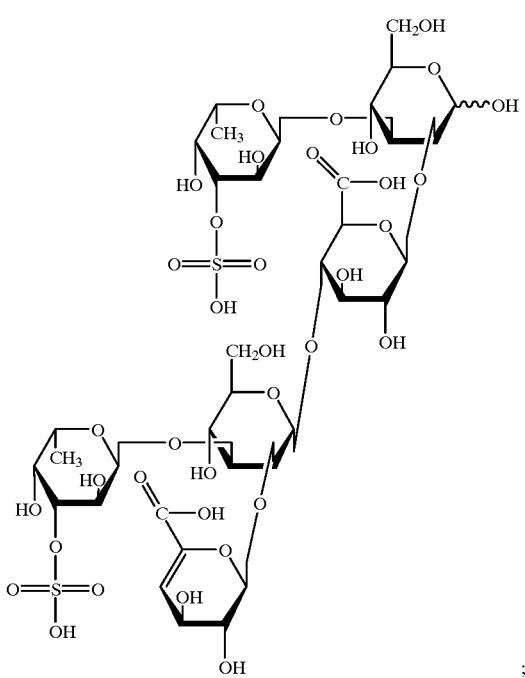

(ii) optimum pH value: being from about pH 7 to 8; and
(iii) optimum temperature: being from about 30 to 35° C.

The sixteenth invention of the present invention relates to an enzyme composition containing a calcium source and an endo-sulfated-fucose-containing polysaccharide degrading enzyme of the fifteenth invention of the present invention.

The seventeenth invention of the present invention relates to a process for producing an endo-sulfated-fucose-containing polysaccharide degrading enzyme of the fifteenth invention of the present invention which comprises incubating an Alteromonas capable of producing the endo-sulfated-fucose-containing polysaccharide degrading enzyme of the fifteenth invention of the present invention and recovering the enzyme from the culture medium.

The eighteenth invention of the present invention relates to degradation products of sulfated-fucose-containing polysaccharides obtained by treating sulfated-fucose-containing polysaccharides of the sixth invention of the present invention with an endo-sulfated-fucose-containing polysaccharide degrading enzyme of the fifteenth invention of the present invention.

The present inventors have successfully obtained various purified sulfated-fucose-containing polysaccharides and degradation products thereof and subsequently examined biological activities of these substances. As a result, they have found out that these substances induce apoptosis of cancer cells and have potent anticancer effects. They have further found out that the sulfated-fucose-containing polysaccharides and/or degradation products thereof have potent carcinostatic effects. They have furthermore succeeded in the isolation of an enzyme capable of degrading sulfated-fucose-containing polysaccharides and being useful in the preparation of the degradation products of the present invention, thus completing the present invention.

DESCRIPTION OF THE PREFERRED EMBODIMENTS

Figure 1:
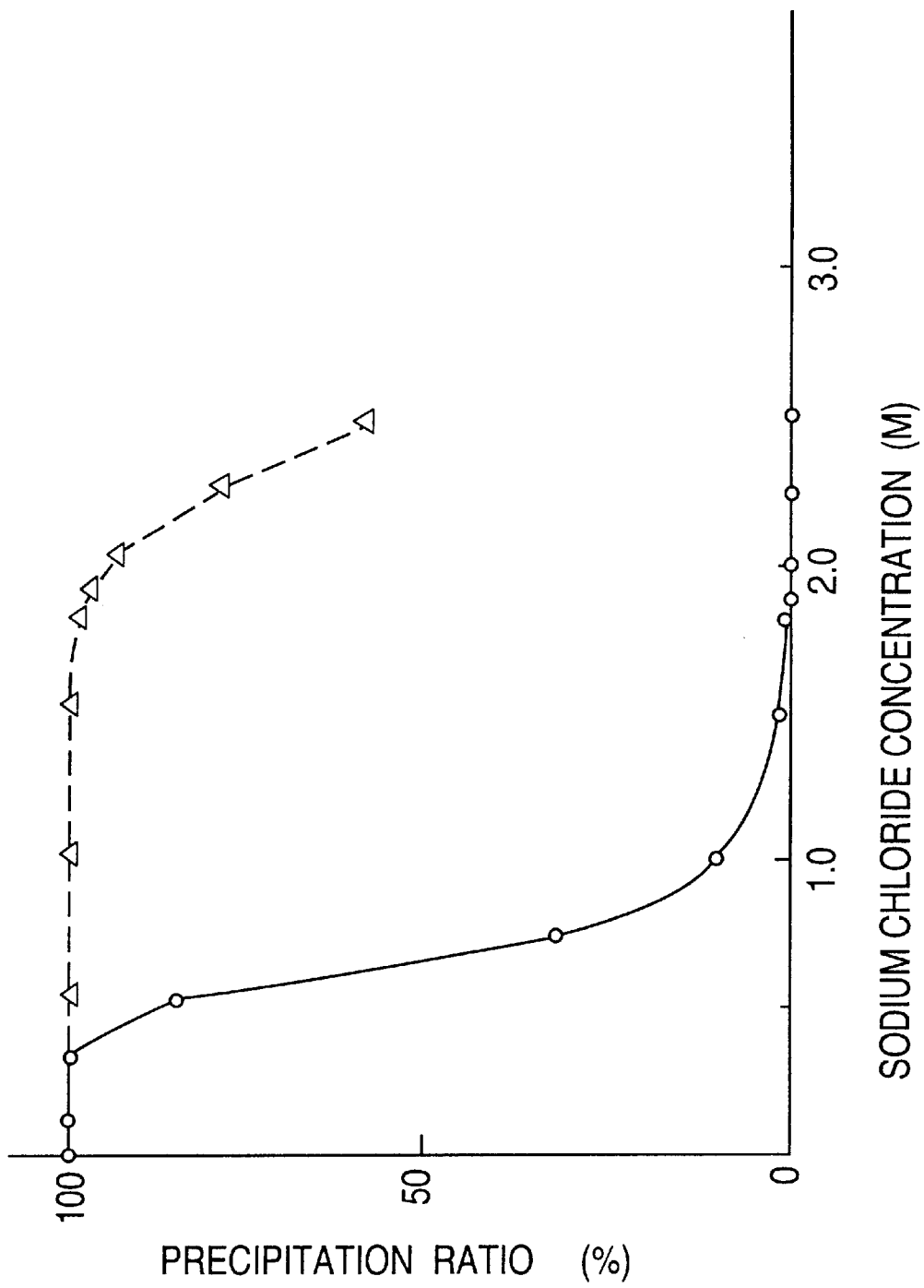
FIG. 1 shows the precipitation ratios of sulfated-fucose-containing polysaccharides.

Now, the present invention will be described in greater detail.

The sulfated-fucose-containing polysaccharides to be used in the present invention are not particularly restricted. For example, use can be made therefor of those originating in *Kjellmaniella crassifolia, Laminaria japonica, Undaria pinnatifida* and any other brown algae (Phaeophyta). It is known that sea cucumber has sulfated-fucose-containing polysaccharides in its somatic wall. It is also possible in the present invention to use the sulfated-fucose-containing polysaccharides originating in sea cucumber. Moreover, degradation products of sulfated-fucose-containing polysaccharides are usable in the present invention. Sulfated-fucose-containing polysaccharides may be degraded by, for example, chemical degradation methods such as a treatment with an acid, physical degradation methods such as ultra-sonication or enzymatic degradation methods.

The present inventors have found out that when various sulfated-fucose-containing polysaccharides and/or degradation products thereof as described above are added to a culture medium of cancer cells, the cancer cells undergo apoptosis within one to several days following the addition. They have also confirmed that the sulfated-fucose-containing polysaccharides and/or degradation products thereof exhibit no toxicity on normal cells.

The term "sulfated-fucose-containing polysaccharide" as used herein means a polysaccharide having sulfated fucose in its molecule without particular restriction. Examples thereof include those contained in brown algae and sea cucumber ["Tatorui Kagaku", supervised by Tokuro Soda, edited by Fujio Egami, Kyoritsu Shuppan K.K., Dec. 15, 1955, p. 319, p. 321]. Sulfated-fucose-containing polysaccharides originating in brown algae are commonly called fucoidan, fucoidin and fucan. Although it is known that there are several molecular species thereof, these sulfated-fucose-containing polysaccharide are frequently called fucoidan in general. For example, it is reported that fucoidan manufactured by Sigma Chemical Co. is divided into 13 molecular species [Carbohydrate Research, 255, 213–224 (1994)] including a group containing fucose as the main component and another group containing several % of uronic acid and being rich in fucose and mannose as the constituting saccharides. There has been reported that these sulfated-fucose-containing polysaccharides have various biological activities of, for example, potentiating macrophage activity, inhibiting cancerous metastasis and inhibiting blood coagulation. However the sulfated-fucose-containing polysaccharides involve various molecular species and it is therefore necessary to separate and purify the sulfated-fucose-containing polysaccharides in order to clarify which molecular species actually has a certain activity. Sulfated-fucose-containing polysaccharides involve those which are substantially free from uronic acid and contain fucose as the main component of the constituting saccharides and those which contain several % of uronic acid and are rich in fucose and mannose as the constituting saccharides. Hereinafter, the sulfated-fucose-containing polysaccharides substantially free from uronic acid will be referred to as sulfated-fucose-containing polysaccharide-F, those containing uronic acid will be referred to as sulfated-fucose-containing polysaccharide-U and a mixture of both of these sulfated-fucose-containing polysaccharides is referred to as a sulfated-fucose-containing polysaccharide mixture.

Although there have been known methods for separating the sulfated-fucose-containing polysaccharide-F and the sulfated-fucose-containing polysaccharide-U such as molecular weight fractionation and separation with the use of an anion exchange resin, only insufficient separation can be achieved thereby, which makes it difficult to prepare sulfated-fucose-containing polysaccharides on a large scale as drugs or functional foods.

It is also known that coloring matters can be hardly eliminated completely from sulfated-fucose-containing polysaccharides. Commercially available fucoidan products, etc. are also contaminated with the coloring matters. In usual, these coloring matters, which consist of polyphenol polymers, are highly reactive and inhibit various enzymatic reactions or growth of cells. Further, these coloring matters are sometimes irreversibly adsorbed onto resins or containers made of resins being in contact therewith. Accordingly, it is required to eliminate these highly reactive coloring matters from sulfated-fucose-containing polysaccharides in order to accurately examine the biological activities of the sulfated-fucose-containing polysaccharides and prevent the containers or resins from contamination.

It is known that when a sulfated-fucose-containing polysaccharide mixture is extracted from, for example, brown algae or the alcohol-washing residue thereof, the contamination of the extract with alginic acid can be inhibited by adding soluble barium acetate, barium chloride, calcium chloride or the like, which facilitates the subsequent purification. However, the addition of a soluble barium salt makes the treatment of the waste liquor troublesome. On the other hand, calcium chloride causes a change in pH value when mixed with marine algae, which makes it necessary to regulate the pH value in order to give an undegradable sulfated-fucose-containing polysaccharides. In the step of regulating the pH value, it is sometimes observed that marine algae become viscous and aggregate. In such a case, the efficiency in the subsequent extraction is lowered or the solid/liquid separation, in particular, filtration becomes difficult.

Although the usefulness of sulfated-fucose-containing polysaccharides has been expected in the art, there is available neither any marketed product of sulfated-fucose-containing polysaccharide-F or sulfated-fucose-containing polysaccharide-U with sufficient fractionation of molecular species nor a report on a method for efficiently producing sulfated-fucose-containing polysaccharides. Moreover, marketed sulfated-fucose-containing polysaccharides contain highly reactive coloring matters as described above.

Although sulfated-fucose-containing polysaccharides have various activities there has been obtained neither substantially purified sulfated-fucose-containing polysaccharide-F nor sulfated-fucose-containing polysaccharide-U hitherto due to the difficulty in the fractional preparation thereof as described above.

However, the present invention provides substantially purified sulfated-fucose-containing polysaccharide-U, a convenient method for extracting the same and a process for producing the sulfated-fucose-containing polysaccharide-U. The present invention further provides the sulfated-fucose-containing polysaccharide-U from which highly reactive coloring matters which are usually hard to remove from sulfated-fucose-containing polysaccharides and which inhibit enzymatic reactions and contaminate resins, etc. have been eliminated.

The present invention furthermore provides substantially purified sulfated-fucose-containing polysaccharide-F, a convenient method for extracting the same and a process for producing the sulfated-fucose-containing polysaccharide-F.

The present invention further provides the sulfated-fucose-containing polysaccharide-F from which highly reactive coloring matters which are usually hard to remove from sulfated-fucose-containing polysaccharides and which inhibit enzymatic reactions and contaminate resins, etc. have been eliminated.

As the sulfated-fucose-containing polysaccharides to be used in the present invention, use can be made of sulfated-fucose-containing polysaccharide-containing materials such as brown algae and sea cucumber which have been, for example, dried as such and ground. Alternatively, use can be made of a sulfated-fucose-containing polysaccharide-containing extract obtained from a sulfated-fucose-containing polysaccharide-containing material either as such or in the purified state. The sulfated-fucose-containing polysaccharide-containing extract may be prepared and purified each by a publicly known method without restriction.

The degradation products of the sulfated-fucose-containing polysaccharides to be used in the present invention are those obtained by degrading the sulfated-fucose-containing polysaccharides by enzymatic, chemical or physical methods and use can be made of publicly known enzymatic, chemical or physical methods therefor.

The sulfated-fucose-containing polysaccharides and degradation products of the sulfated-fucose-containing polysaccharides to be used in the present invention include pharmaceutically acceptable salts thereof.

Examples of the brown algae containing sulfated-fucose-containing polysaccharides from which sulfated-fucose-containing polysaccharide can be prepared include those described in "Colored Illustrations of Marine Algae of Japan" [foreword: Sachio Yamada, written by Sokichi Segawa, Hoikusha Publishing Co., Ltd., 22–52 (1977)] such as *Kjellmaniella crassifolia, Laminaria japonica* and *Undaria pinnatifida*.

As the sea cucumber containing sulfated-fucose-containing polysaccharides from which sulfated-fucose-containing polysaccharides can be prepared, use can be made of, for example, those described in Japanese Patent Laid-Open No. 91027/1992 such as *Stichopus japonicus* and *Holothuria leucospilota*.

A sulfated-fucose-containing polysaccharide carries in its molecule sulfate groups which react with various bases to thereby form salts. These sulfated-fucose-containing polysaccharides and degradation products of the same become stable when converted into salts thereof. They are usually isolated in the form of sodium and/or potassium salts or the like. The salts of these substances can be converted into free sulfated-fucose-containing polysaccharides and free degradation products of the same by treating with a cation exchange resin such as Dowex 50W. Furthermore, these salts may be subjected to salt exchange reactions in a conventional manner to thereby convert into various desired salts, if necessary. As the salts of the sulfated-fucose-containing polysaccharides and degradation products thereof, use can be made of pharmaceutically acceptable ones, for example, salts of alkali metals such as potassium and sodium, salts of alkaline earth metals such as calcium, magnesium and barium, salts with organic bases such as pyridinium, and ammonium salts.

A powder containing sulfated-fucose-containing polysaccharides may be prepared by drying brown algae, sea cucumber and the like containing sulfated-fucose-containing polysaccharides and then ground.

An extract containing sulfated-fucose-containing polysaccharides may be prepared by extracting the powder containing sulfated-fucose-containing polysaccharides with hot water or a dilute acid.

To extract substances containing sulfated-fucose-containing polysaccharides, the extraction temperature and time may be appropriately selected depending on the purpose respectively from the ranges of 0 to 200° C. and 1 to 360 minutes. The extraction temperature and time are usually selected from the range of 10 to 150° C., preferably 50 to 130° C., and from the range of 5 to 240 minutes, preferably 10 to 180 minutes, respectively.

As a means for purifying the extract so as to elevate the sulfated-fucose-containing polysaccharide content, use can be made of, for example, fractionation of the sulfated-fucose-containing polysaccharides with the use of calcium chloride, barium acetate, etc.; fractionation of the sulfated-fucose-containing polysaccharides with the use of an acidic polysaccharide agglutinating agent such as cetylpyridinium chloride; fractionation of the sulfated-fucose-containing polysaccharides with the use of an acidic polysaccharide agglutinating agent in the presence of salts; gel filtration; and ion exchange chromatography. If necessary, purification may be effected by combining these procedures.

The sulfated-fucose-containing polysaccharides may be degraded by the methods publicly known for degrading sulfated-fucose-containing polysaccharides, for example, use of a sulfated-fucose-containing polysaccharide degrading enzyme, degradation with an acid, and ultrasonication. The degradation products may be purified in accordance with the methods described above.

Brown algae usually contain a number of sulfated-fucose-containing polysaccharides. The brown algae to be used in the present invention are not particularly restricted. For example, use can be made of those originating in *Kjellmaniella crassifolia, Laminaria japonica, Undaria pinnatifida* and any other brown algae.

To produce the sulfated-fucose-containing polysaccharides, brown algae are first extracted with an aqueous solvent.

The marine algae to be extracted may be fresh ones. However, it is advantageous that, prior to the preparation of the extract, the brown algae are dried, powdered, washed with 60 to 100% alcohol or acetone or soaked in an aqueous solution containing formaldehyde, acetaldehyde, glutaraldehyde, ammonia or the like, since the contamination of the sulfated-fucose-containing polysaccharides with coloring matters can be considerably relieved thereby.

When sulfated-fucose-containing polysaccharides are extracted from, for example, brown algae or the alcohol-washing residue thereof, the contamination of the extract with alginic acid can be inhibited by adding soluble barium acetate, barium chloride, calcium chloride or the like, which facilitates the subsequent purification. For the reason described above, it is preferable to extract the sulfated-fucose-containing polysaccharides with a calcium acetate solution of 1 mM to 1 M at a temperature of 50 to 130° C.

When the algae are thick and the powder consists of large particles, it is sometimes observed that only a poor extraction efficiency can be achieved by using a calcium acetate solution of a concentration of 0.2 M or more from beginning. In such a case, it is recommended that the sulfated-fucose-containing polysaccharides are first extracted with water and then calcium acetate is added to the extract followed by the elimination of the alginic acid thus precipitated.

When the sulfated-fucose-containing polysaccharides are to be extracted together with alginic acid or partly degraded products are to be obtained in the step of the extraction, the solvent and conditions for the extraction are not particularly restricted. In such a case, use can be made of water, aqueous solutions of neutral salts such as sodium chloride and magnesium chloride at various concentrations, acidic aqueous solutions of, for example, citric acid, phosphoric acid and hydrochloric acid at various concentrations, and alkaline aqueous solutions of, for example, sodium hydroxide and potassium hydroxide at various concentrations. Moreover, buffers and preservatives may be added thereto. Also, the pH value of the extract, the extraction temperature and extraction time are not particularly restricted. However, sulfated-fucose-containing polysaccharides have generally little resistance against acids and alkalis. Thus, the degradation tends to easily proceed when an acidic or alkaline solution is employed. Arbitrary degradation products can be prepared by controlling the heating temperature, heating time, pH value, etc. For example, the average molecular weight, molecular weight distribution and the like of the degradation products can be controlled by effecting gel filtration, treating with a molecular weight fractionation membrane, etc.

That is to say, the molecular weights and saccharide compositions of the sulfated-fucose-containing polysaccharide-U and sulfated-fucose-containing polysaccharide-F of the present invention vary depending on the harvest time of the sulfated-fucose-containing polysaccharide materials, the method employed for drying the materials, the method employed for storing the materials and the conditions of the extraction of the sulfated-fucose-containing polysaccharides such as heating conditions and pH value. For example, sulfated-fucose-containing polysaccharides are hydrolyzed with acids. Under alkaline conditions, on the other hand, the degradation of sulfated-fucose-containing polysaccharides proceeds as a result of the β-elimination of uronic acid. Accordingly, the molecular weights and molecular weight distributions of the sulfated-fucose-containing polysaccharide-U and the sulfated-fucose-containing polysaccharide-F described herein are each a mere example thereof. The molecular weight and molecular weight distribution can be easily varied by controlling the conditions for treating the sulfated-fucose-containing polysaccharides. For example, the sulfated-fucose-containing polysaccharide-U and the sulfated-fucose-containing polysaccharide-F of about 1,000 to 10,000 in molecular weight distribution can be prepared by heating the starting material at 100° C. for 1 hour under weakly alkaline conditions and using a molecular sieve membrane of 300 in pore size in the step of desalting. The sulfated-fucose-containing polysaccharide-U and the sulfated-fucose-containing polysaccharide-F of the present invention with arbitrary molecular weight and molecular weight distribution can be prepared by appropriately selecting the treating conditions.

Alginic acid and neutral saccharides may be eliminated from the above-mentioned brown alga extract by, for example, adding an acidic polysaccharide agglutinating agent such as cetylpyridinium chloride in the presence of salts such as sodium chloride at a concentration of 0.2 to 0.6 M until no precipitate is formed any more and then collecting the precipitate.

If required, the precipitate is washed with a solution of salts such as 0.2 to 0.6 M of sodium chloride and the cetylpyridinium chloride contained in the precipitate is washed away with a saturated alcoholic solution of sodium chloride to thereby give a sulfated-fucose-containing polysaccharide mixture. To eliminate coloring matters from the sulfated-fucose-containing polysaccharide mixture thus obtained, the precipitate may be dissolved and then treated with an anion exchange resin or a polysaccharide resin or subjected to ultrafiltration. When the precipitate is desalted and freeze-dried, a dry preparation can be obtained.

The present inventors have found out that the sulfated-fucose-containing polysaccharide-F and the sulfated-fucose-containing polysaccharide-U of the present invention show completely different behaviors on an acidic polysaccharide agglutinating agent in the presence of one or more salts at a concentration of 0.6 to 3 M.

For example, the sulfated-fucose-containing polysaccharide-U of the present invention can be separated from an aqueous solution of a sulfated-fucose-containing polysaccharide mixture by using the method of the present invention.

First, one or more salts are added to the aqueous solution of the sulfated-fucose-containing polysaccharide mixture in such a manner as to give a total salt concentration of 0.6 to 2 M. As the salts to be added, use can be made of, for example, sodium chloride and calcium chloride without restriction.

Usually, the sulfated-fucose-containing polysaccharide-F of the present invention can be separated from the sulfated-fucose-containing polysaccharide-U of the present invention at a salt concentration of about 1.5 M (see, the illustration of FIG. 1 as will be given hereinbelow). For example, the salt concentration of the above-mentioned salt(s) is adjusted to 1.5 M and then an acidic polysaccharide agglutinating agent such as cetylpyridinium chloride is added until no precipitate is formed any more. Thus the sulfated-fucose-containing polysaccharide-F is precipitated. By removing the precipitate, the solution of the sulfated-fucose-containing polysaccharide-U of the present invention can be obtained. This solution is concentrated, if necessary, and then the sulfated-fucose-containing polysaccharide-U contained therein is precipitated by adding, for example, 4 times as much ethanol thereto. Next, the cetylpyridinium chloride in the precipitate is washed away with a saturated alcoholic solution of sodium chloride to thereby give the sulfated-fucose-containing polysaccharide-U of the present invention. The sulfated-fucose-containing polysaccharide-U thus obtained may be dissolved and then subjected to ultrafiltration to thereby remove coloring matters therefrom. By desalting and freeze-drying the sulfated-fucose-containing polysaccharide-U, a dry preparation can be obtained. It is also possible to add preservatives and the like during the process.

When it is needed to efficiently produce the sulfated-fucose-containing polysaccharide-F of the present invention alone, the salt concentration in the step of the agglutination with, for example, cetylpyridinium chloride is regulated not to 0.2 to 0.6 M but to, for example, 2 M. Thus the obtained precipitate contains exclusively the sulfated-fucose-containing polysaccharide-F of the present invention.

The present inventors have also found out that when sulfated-fucose-containing polysaccharides are purified with the use of an anion exchange resin in the presence of a divalent cation, the amount of the sulfated-fucose-containing polysaccharides adsorbed onto the resin per unit area can be increased and thus the sulfated-fucose-containing polysaccharides can be separated more efficiently. To produce the sulfated-fucose-containing polysaccharide-U of the present invention by using the method of the present invention, therefore, a chemical serving as a divalent cation source is added preferably at a concentration of 1 mM or more to the sulfated-fucose-containing polysaccharide mixture. Next, the anion exchange resin is equilibrated with a solution containing the divalent cation preferably at a concentration of 1 mM or more and the above-mentioned sulfated-fucose-containing polysaccharide mixture is adsorbed thereby. After thoroughly washing the anion exchange resin with the solution employed in the equilibration, the sulfated-fucose-containing polysaccharides are developed by linear gradient elution with, for example, sodium chloride. In the practice of this method, the divalent cation may be added so as to give a concentration of 1 mM or more. When the sulfated-fucose-containing polysaccharide-U of the present invention is to be adsorbed by the column, the concentration is preferably regulated to less than 0.5 M. As the chemical serving as the divalent cation source to be used in this method, calcium salts and barium salts exhibit particularly excellent effects. However, the present invention is not restricted thereto and use can be also made of magnesium sulfate, manganese chloride, etc. therefor.

When a sulfated-fucose-containing polysaccharide mixture is produced from brown algae by the conventional method, the obtained mixture is contaminated with highly reactive coloring matters which contaminate resins or resin containers being in contact therewith or inhibit enzymatic reactions or the growth of cells, as described above. It is found out that these coloring matters can be easily eliminated through binding or adsorption by a polysaccharide substance or a substance carrying an anion exchange group. That is to say, these highly reactive coloring matters can be easily eliminated by adding, to the solution containing the sulfated-fucose-containing polysaccharides, polysaccharide resins such as Cellulofine GCL-2000 (mfd. by Seikagaku Kogyo), Sephacryl S-500, Sephadex G-200 and Sepharose CL-2B (each mfd. by Pharmacia) or substances carrying an anion exchange group such as DEAE-Cellulofine A-800 (mfd. by Seikagaku Kogyo), DEAE-Sepharose FF, DEAE-Sephadex A-50, QAE-Sephadex A-50, DEAE-Sephacel (each manufactured by Pharmacia), TSK-Gel DEAE-Toyopearl 650, TSK-Gel DEAE Toyopearl 550 (each mfd. by Tosoh Corporation), Amberlite anion exchange resin (mfd. by Organo) and chitopearl anion exchange resin (mfd. by Fuji Spinning Co., Ltd.), stirring and then removing, or passing the solution containing the sulfated-fucose-containing polysaccharides through a column packed with these substances. However, an anion exchange resin also binds to the sulfated-fucose-containing polysaccharides. Thus it is preferable to control the salt concentration to about 2 M in the step of the adsorption of the coloring matters.

The sulfated-fucose-containing polysaccharide-U of the present invention can be prepared by, for example, the method described in Example 6. Next, the physicochemical properties of this sulfated-fucose-containing polysaccharide-U will be illustrated, though the sulfated-fucose-containing polysaccharide-U of the present invention is not restricted thereto.

FIG. 1 shows the precipitation ratio of this sulfated-fucose-containing polysaccharide-U of the present invention and that of the sulfated-fucose-containing polysaccharide-F of the present invention obtained in Example 8 at various sodium chloride concentrations in the presence of cetylpyridinium chloride in excess.

In FIG. 1, the ordinate refers to the precipitation ratio (%) while the abscissa refers to the concentration (M) of sodium chloride. The solid line and open circle stand for the precipitation ratio of the sulfated-fucose-containing polysaccharide-U of the present invention at various sodium chloride concentrations, while the dotted line and open triangle stand for the precipitation ratio of the sulfatedfucose-containing polysaccharide-F of the present invention at various sodium chloride concentrations (M).

The precipitation ratios are determined at a solution temperature of 37° C. in the following manner.

The sulfated-fucose-containing polysaccharide-U and the sulfated-fucose-containing polysaccharide-F of the present invention are each dissolved in water and 4 M of sodium chloride at a concentration of 2%. Then these solutions are mixed at various ratios to thereby give 125 μl portions of sulfated-fucose-containing polysaccharide-U and sulfated-fucose-containing polysaccharide-F solutions having various sodium chloride concentrations. Next, cetylpyridinium chloride was dissolved in water and 4 M of sodium chloride at a concentration of 2.5% and the obtained solutions are mixed at various ratios to thereby give 1.25% solutions of cetylpyridinium chloride with various sodium chloride concentrations.

3.2 times by volume as much the 1.25% solution of cetylpyridinium chloride is needed to completely precipitate the sulfated-fucose-containing polysaccharide-U and sulfated-fucose-containing polysaccharide-F of the present invention each dissolved in water at a concentration of 2%. To 125 μl portions of 2% solutions of the sulfated-fucose-containing polysaccharide-U and the sulfated-fucose-containing polysaccharide-F with various sodium chloride concentrations were added 400 μl portions of cetylpyridinium chloride solutions with various sodium chloride concentrations. After thoroughly stirring and allowing to stand for 30 minutes, each mixture is centrifuged and the saccharide content of the supernatant is determined by the phenol-sulfuric acid method [Analytical Chemistry, 28, 350 (1956)] followed by the calculation of the precipitation ratio of each sulfated-fucose-containing polysaccharide at each sodium chloride concentration.

Figure 2:
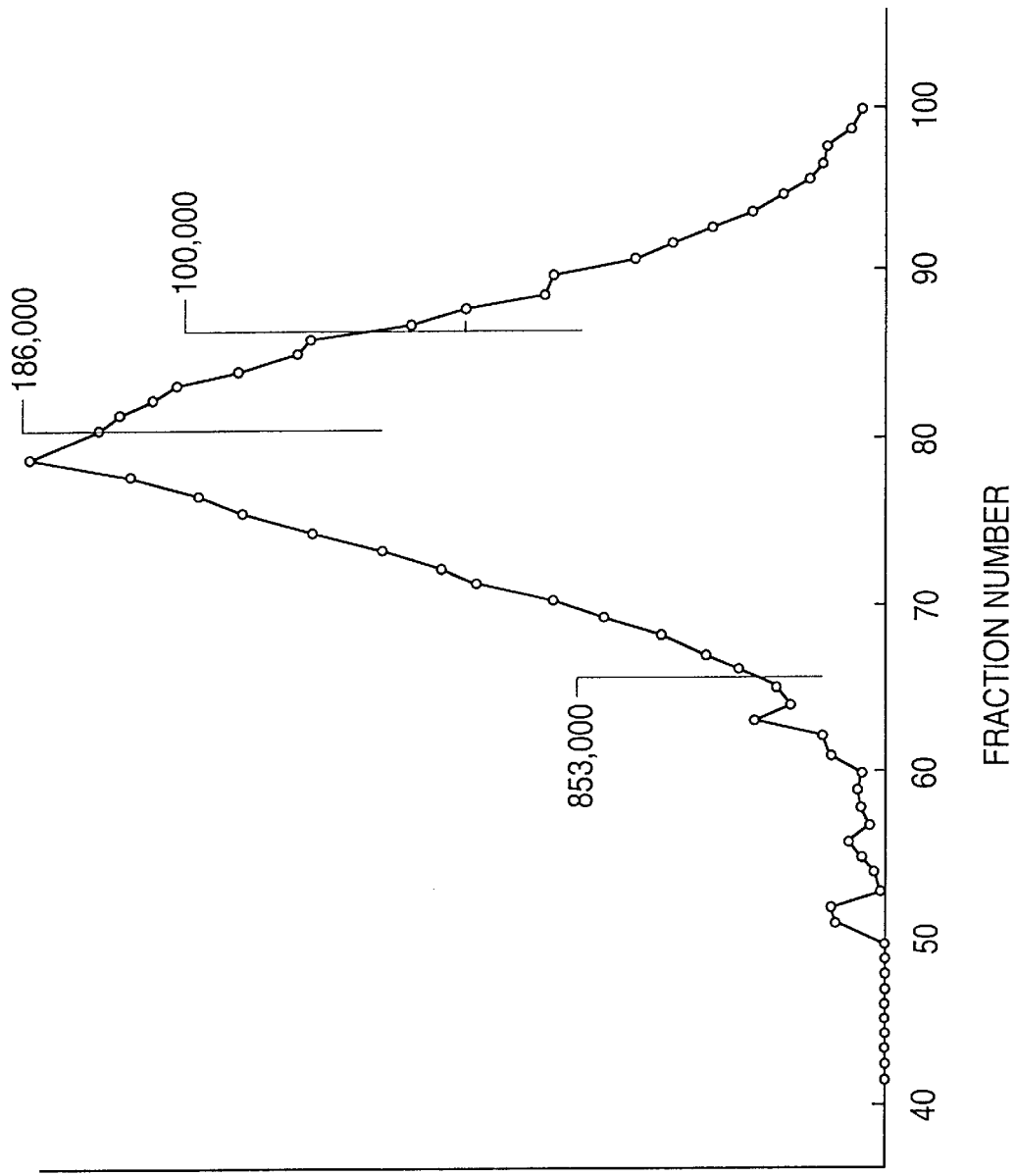
FIG. 2 shows the molecular weight distribution of the sulfated-fucose-containing polysaccharide-U determined by the gel filtration method with the use of Sephacryl S-500.

The molecular weight of the sulfated-fucose-containing polysaccharide-U of the present invention thus obtained is determined by the gel filtration method with the use of Sephacryl S-500. As a result, it shows a molecular weight distribution around about 190,000 (FIG. 2). In FIG. 2, the ordinate refers to the saccharide content of the sample determined by the phenol-sulfuric acid method which is expressed in the absorbance at 480 nm while the abscissa refers to the fraction number.

The gel filtration is effected under the following conditions:

| | |
|---|---|
| column size | 3.08 × 162.5 cm; |
| solvent | 10 mM sodium phosphate buffer (pH 6.0) containing 0.2M of sodium chloride and 10% of ethanol; |
| flow rate | 1.5 ml/min; |
| sample concentration | 0.25%; |
| sample volume | 20 ml; and |
| molecular weight standard | Shodex STANDARD P-82 (mfd. by Showa Denko, K. K.). |

Next, the components of the sulfated-fucose-containing polysaccharide-U of the present invention thus obtained are analyzed.

First, the fucose content is determined in accordance with the method described in Journal of Biological Chemistry, 175, 595 (1948).

Next, the dry preparation of the sulfated-fucose-containing polysaccharide-U thus obtained is dissolved in 1 N hydrochloric acid to give a concentration of 0.5% and treated at 110° C. for 2 hours to thereby hydrolyze into constituting monosaccharides. Subsequently, the reducing ends of the monosaccharides obtained by the hydrolysis are pyridyl-(2)-aminated (PA) by using GlycoTAG and Glyco-TAG Reagent Kit (each mfd. by Takara Shuzo Co., Ltd.) and the composition ratio of the constituting monosaccharides is analyzed by HPLC. The HPLC is effected under the following conditions:

| | |
|---|---|
| apparatus | Model L-6200 (mfd. by Hitachi, Ltd.); |
| column | PALPAK Type A (4.6 mm × 150 mm, mfd. by Takara Shuzo, Co., Ltd.); |
| eluent | 700 mM borate buffer (pH 9.0) acetonitrile = 9:1 |
| detection | Fluorometric Detector F-1150 (mfd. by Hitachi, Ltd.), excitation wavelength: 310 nm, fluorescent wavelength: 380 nm; |
| flow rate | 0.3 ml/min; and |
| column temperature | 65° C. |

Next, the content of uronic acid is determined in accordance with the method described in Analytical Biochemistry, 4, 330 (1962).

Subsequently, the content of sulfuric acid is determined in accordance with the method described in Biochemical Journal, 84, 106 (1962).

As a result, it is found out that the constituting saccharides of the sulfated-fucose-containing polysaccharide-U obtained above are fucose, mannose, galactose, glucose, rhamnose, xylose and uronic acid and no other neutral saccharide is substantially contained therein. The composition ratio by mol of the major components is as follows; fucose:mannose:galactose:uronic acid:sulfate group=about 10:7:4:5:20.

Figure 3:
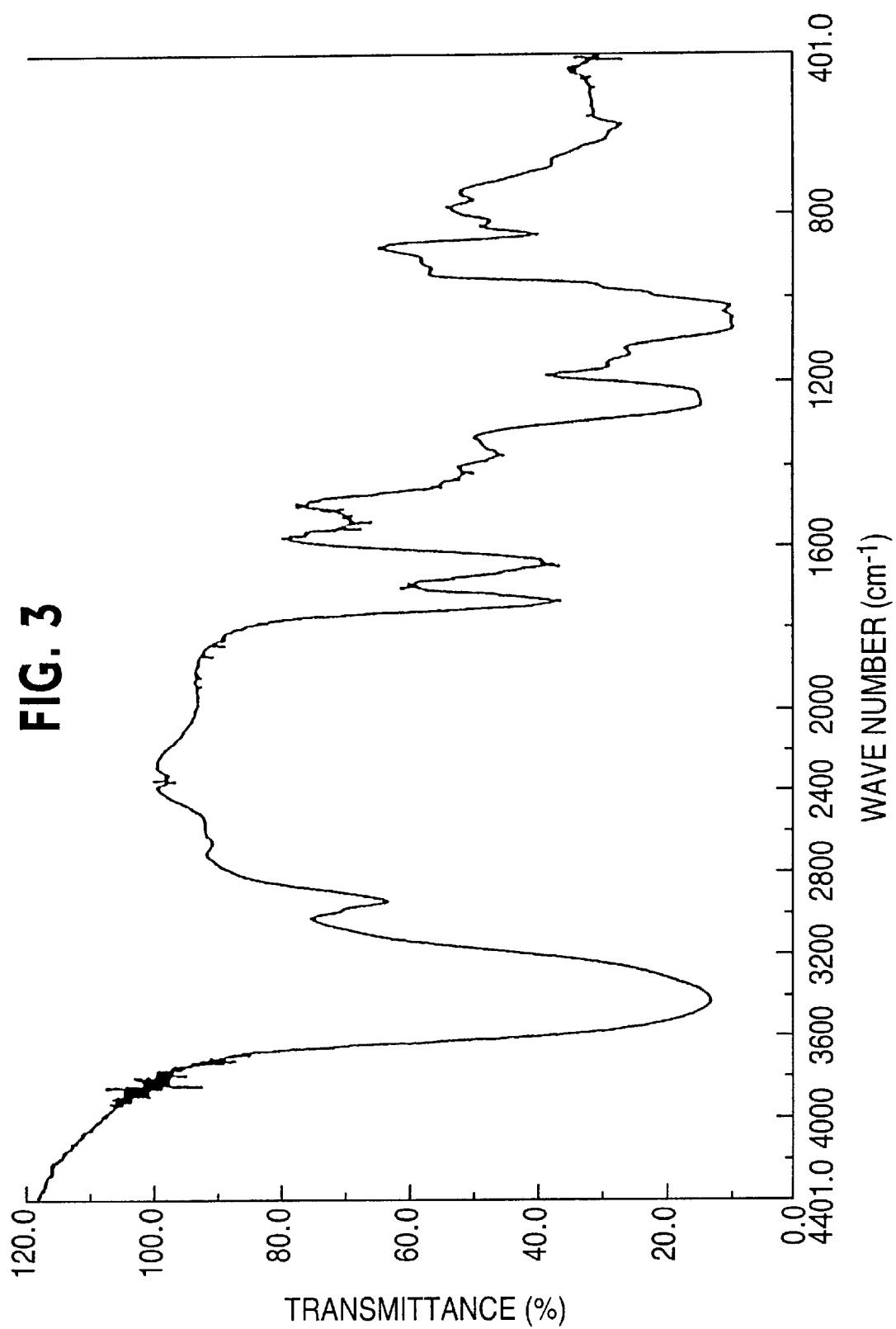
FIG. 3 is the IR spectrum of the sulfated-fucose-containing polysaccharide-U.

Then the IR spectrum of the sulfated-fucose-containing polysaccharide-U calcium salt is measured with a Fourier transform infrared spectrometer JIR-DIAMOND 20 (mfd. by JEOL Ltd.). Thus the spectrum as shown in FIG. 3 is obtained. In FIG. 3, the ordinate refers to the transmittance (%) while the abscissa refers to the wave number ($cm^{-1}$).

Next, the NMR spectrum of calcium salt of the sulfated-fucose-containing polysaccharide-U of the present invention is measured with a nuclear magnetic resonance spectrometer Model JNM-α500 (500 MHz; mfd. by JEOL Ltd.). Thus the spectrum as shown in FIG. 4 is obtained.

Figure 4:
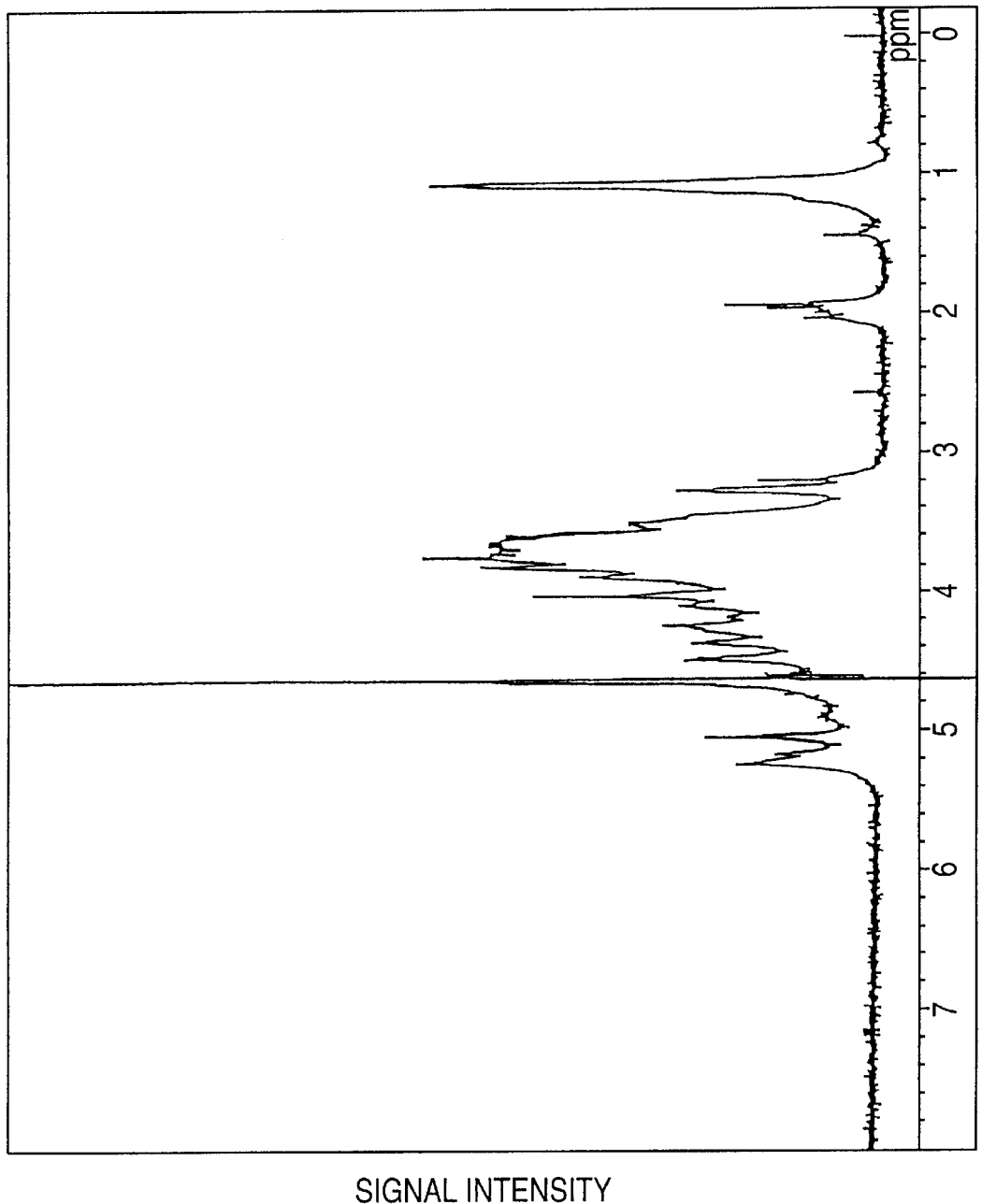
FIG. 4 is the $^1$H-NMR spectrum of the sulfated-fucose-containing polysaccharide-U.

In FIG. 4, the ordinate refers to the signal intensity while the abscissa refers to the chemical shift (ppm). The chemical shifts in $^1$H-NMR are expressed by taking the chemical shift of HOD as 4.65 ppm.

$^1$H-NMR ($D_2O$): δ 5.27 (H at the 1-position of mannose), 5.07 (H at the 1-position of fucose), 4.49 (H at the 3-position of fucose), 4.37 (H at the 1-position of glucuronic acid), 4.04 ((H at the 4-position of fucose), 3.82 (H at the 2-position of fucose), 3.54 (H at the 3-position of glucuronic acid), 3.28 (H at the 2-position of glucuronic acid), 1.09 (H in $CH_3$ at the 5-position of fucose).

When measured with a high-speed, high-sensitivity polarimeter SEPA-300 (mfd. by Horiba Seisakusho), the freeze-dried product of the sulfated-fucose-containing polysaccharide-U of the present invention has a specific rotation of −53.6°.

The present inventors have identified the structure of the thus obtained sulfated-fucose-containing polysaccharide-U of the present invention in the following manner.

Degradation of sulfated-fucose-containing polysaccharide-U with degrading enzyme capable of degrading sulfated-fucose-containing polysaccharide-U and purification of the degradation product:

The purified sulfated-fucose-containing polysaccharide-U is treated with an endofucoidanase as will be described hereinafter and the degradation products are purified.

Namely, 16 ml of a 1% solution of the sulfated-fucose-containing polysaccharide-U, 12 ml of a 50 mM phosphate buffer (pH 8.0), 4 ml of a 4 M solution of sodium chloride and 8 ml of a 32 mU/ml solution of the endofucoidanase are mixed together and reacted at 25° C. for 48 hours. It is confirmed that the absorbance of the reaction mixture at 230 nm is elevated as the reaction proceeds, thus proving that the degradation of the sulfated-fucose-containing polysaccharide-U with this enzyme is in progress. After desalting with a Micro Acilyzer G3 (mfd. by Asahi Chemical Industry Co., Ltd.), the reaction mixture is separated into three fractions (a), (b) and (c) and purified with a DEAE-Sepharose FF.

The above-mentioned endofucoidanase is prepared in the following manner.

The strain to be used in the production of this enzyme may be an arbitrary one, so long as it is capable of producing the endofucoidanase. As a particular example thereof, citation can be made of Flavobacterium sp. SA-0082 (FERM BP-5402).

This strain, which was isolated by the present inventors from seawater in Aomori, has the following mycological properties.

| 1. Flavobacterium sp. SA-0082 strain | |
|---|---|
| a. Morphological properties | |
| (1) Short rod; | |
| width | 0.8–1.0 μm |
| length | 1.0–1.2 μm |
| (2) Spore | none |
| (3) Gram-staining | − |
| b. Physiological properties | |
| (1) Growth temperature range: | capable of growing at 37° C. or less, appropriate growth temperature ranging from 15 to 28° C. |
| (2) Attitude to oxygen | aerobic |
| (3) Catalase | + |
| (4) Oxidase | + |
| (5) Urease | weakly + |
| (6) Acid formation | |
| D-glucose | + |
| lactose | + |
| maltose | + |
| D-mannitol | + |
| sucrose | − |
| trehalose | − |
| (7) Hydrolysis | |
| starch | − |
| gelatin | + |
| casein | − |
| esculin | + |
| (8) Reduction of nitrate | − |
| (9) Indole formation | − |
| (10) Hydrogen sulfide formation | − |
| (11) Solidification of milk | − |
| (12) Sodium requirement | + |
| (13) Salt requirement | |

-continued

| | |
|---|---|
| Growth in NaCl-free medium | − |
| Growth in 1% NaCl medium | − |
| Growth in seawater medium | + |
| (14) Quinone | menaquinone 6 |
| (15) GC content in intracellular DNA | 32% |
| (16) OF-test | O |
| (17) Colony color | yellow |
| (18) Motility | none |
| (19) Gliding | none. |

It is presumable that this strain is a bacterium analogous to *Flavobacterium aquatile* and *Flavobacterium meningosepticum* described in Bergey's Manual of Systematic Bacteriology, 1 (1984) and Bergey's Manual of Determinative Bacteriology, 9 (1994). However, this strain differs from the former in being incapable of forming any acid via the metabolism of sucrose, incapable of decomposing casein, capable of decomposing esculin, capable of liquefying gelatin and being positive to urease, and from the latter in being incapable of decomposing casein and slowly growing at 37° C. Accordingly, this strain has been identified as a bacterium belonging to the genus Flavobacterium and named Flavobacterium sp. SA-0082.

The above strain is indicated as Flavobacterium sp. SA-0082 and has been deposited at National Institute of Bioscience and Human-Technology, Agency of Industrial Science and Technology (1-3, Higashi 1-chome, Tsukuba-shi, Ibaraki-ken 305, JAPAN) under the accession number FERM P-14872 since Mar. 29, 1995 and deposited at National Institute of Bioscience and Human-Technology as described above under the accession number FERM BP-5402 (transfer to international deposition being requested on Feb. 15, 1996).

The nutrients to be added to the medium for incubating this strain may be arbitrary ones so long as the strain employed can utilize them so as to produce the endofucoidanase. Appropriate examples of the carbon source include fucoidan, marine alga powder, alginic acid, fucose, glucose, mannitol, glycerol, saccharose, maltose, lactose and starch, while appropriate examples of the nitrogen source include yeast extract, peptone, casamino acids, corn steep liquor, meat extract, defatted soybean, ammonium sulfate and ammonium chloride. The medium may further contain inorganic matters and metal salts such as sodium salts, phosphates, potassium salts, magnesium salts and zinc salts.

The yield of the endofucoidanase produced by incubating the strain varies depending on the incubation conditions. In general, it is preferable that the incubation temperature ranges from 15 to 30° C. and the pH value of the medium ranges from 5 to 9. The yield of the endofucoidanase attains the maximum by incubating the strain under aeration and agitation for 5 to 72 hours. As a matter of course, the incubation conditions are appropriately selected depending on the strain employed, the medium composition, etc. so as to achieve the maximum yield.

The endofucoidanase is contained in both of the cells and the culture supernatant.

The above-mentioned Flavobacterium sp. SA-0082 is incubated in an appropriate medium and the cells are harvested and disrupted by a means commonly employed for disrupting cells such as ultrasonication. Thus a cell-free extract can be obtained.

Subsequently, the extract is purified by a purification procedure commonly employed in the art to thereby give a purified enzyme preparation. For example, the purification may be effected by salting out, ion exchange chromatography, hydrophobic bond column chromatography, gel filtration or the like to thereby give the purified endofucoidanase free from any other fucoidanase.

The culture supernatant obtained by eliminating the cells from the above-mentioned culture medium also contains a large amount of this enzyme (extracellular enzyme) which can be purified by the same means as those employed for purifying the intracellular enzyme.

Now an example of the purification of the endofucoidanase will be given.

Flavobacterium sp. SA-0082 (FERM BP-5402) is inoculated into 600 ml of a medium comprising an artificial seawater (pH 7.5, mfd. by Jamarin Laboratory) containing 0.25% of glucose, 1.0% of peptone and 0.05% of yeast extract which has been pipetted into a 2-l Erlenmeyer flask and sterilized at 120° C. for 20 minutes. Then the strain is incubated therein at 24° C. for 24 hours to thereby give a seed culture. Into a 30-l jar fermenter is fed 20 l of a medium comprising an artificial seawater (pH 7.5, mfd. by Jamarin Laboratory) containing 0.25% of glucose, 1.0% of peptone, 0.05% of yeast extract and 0.01% of a defoaming agent (KM70 mfd. by Shin-Etsu Chemical Co., Ltd.) and sterilized at 120° C. for 20 minutes. After cooling, the medium is inoculated with 600 ml of the above-mentioned seed culture, which is then incubated therein at 24° C. for 24 hours under aerating at a rate of 10 l/min and agitating at 125 rpm. After the completion of the incubation, the culture medium is centrifuged to thereby collect the cells.

These cells are suspended in a 20 mM acetate-phosphate buffer (pH 7.5) containing 200 mM of sodium chloride, disrupted by ultrasonication and centrifuged to thereby give a cell extract. The endofucoidanase in this cell extract shows an activity of 5 mU/ml of the medium.

To this extract is added ammonium sulfate so as to establish 90% saturation finally. After dissolving by stirring, the mixture is centrifuged and the precipitate is suspended in the same buffer as the above-mentioned one in which the cells are suspended. Then the suspension is thoroughly dialyzed against a 20 mM acetate-phosphate buffer (pH 7.5) containing 50 mM of sodium chloride. After eliminating the precipitate formed by the dialysis by centrifugation, it is adsorbed by a DEAE-Sepharose FF column which has been equilibrated with a 20 mM acetate-phosphate buffer (pH 7.5) containing 50 mM of sodium chloride. Then the adsorbed matter is well washed with the same buffer and developed by linear gradient elution with sodium chloride of 50 mM to 600 mM. The active fractions are combined and sodium chloride is added thereto so as to give a final concentration of 4 M. Next, it is adsorbed by a Phenyl Sepharose CL-4B column which has been equilibrated with a 20 mM phosphate buffer (pH 8.0) containing 4 M of sodium chloride. Then the adsorbed matter is well washed with the same buffer and developed by linear gradient elution with sodium chloride of 4 M to 1 M. The active fractions are combined and concentrated with an ultrafilter. Next, it is subjected to gel filtration with the use of Sephacryl S-300 which has been equilibrated with a 10 mM phosphate buffer containing 50 mM of sodium chloride. The active fractions are combined. The molecular weight of the enzyme determined from the retention time in Sephacryl S-300 is about 460,000. Next, the active fraction is dialyzed against a 10 mM phosphate buffer (pH 7) containing 250 mM of sodium chloride. The enzyme solution is adsorbed by a Mono Q HR5/5 column which has been equilibrated with a 10 mM phosphate buffer (pH 7) containing 250 mM of sodium chloride. The adsorbed matter is well washed with the same buffer and developed by linear gradient elution with sodium chloride of 250 mM to 450 mM. The active fractions are combined to thereby give the purified enzyme. Table 1 summarizes the above-mentioned purification steps.

TABLE 1

| Step | Total protein (mg) | Total activity (mU) | Specific activity (mU/mg) | Yield (%) |
|---|---|---|---|---|
| cell extract | 61,900 | 101,000 | 1.63 | 100 |
| ammonium sulfate-salting out | 33,800 | 88,600 | 2.62 | 87.7 |
| DEAE-Sepharose FF | 2,190 | 40,400 | 18.4 | 40.0 |
| Phenyl Sepharose CL-4B | 48.2 | 29,000 | 601 | 28.7 |
| Sephacryl S-300 | 7.24 | 19,600 | 2,710 | 19.4 |
| Mono Q | 0.824 | 15,000 | 18,200 | 14.9 |

The activity of this enzyme is determined in the following manner.

50 μl of a 2.5% solution of fucoidan originating in Kjellmaniella crassifolia, 10 μl of this enzyme and 60 μl of a 83 mM phosphate buffer (pH 7.5) containing 667 mM of sodium chloride are mixed together and reacted at 37° C. for 3 hours. Then 105 μl of the reaction mixture is mixed with 2 ml of water under stirring and the absorbance (AT) is measured at 230 nm. As controls, use is made of a reaction mixture prepared by the same method but substituting the enzyme by the above-mentioned buffer alone employed for dissolving the enzyme and another reaction mixture prepared by the same method but substituting the fucoidan solution by water alone and the absorbances (AB1 and AB2) thereof are also measured.

The amount of the enzyme by which 1 μmol of the glycoside bonds between mannose and uronic acid can be exclusively cleaved in one minute is taken as one U. The bonds thus cleaved are determined by taking the millimolar molecular extinction coefficient of the unsaturated uronic acid formed in the elimination reaction as 5.5. The activity of the enzyme is determined in accordance with the following equation:

$$\text{Activity (U/ml)} = (AT - AB1 - AB2) \times 2.105 \times 120 / (5.5 \times 105 \times 0.01 \times 180);$$

| | |
|---|---|
| 2.105 | volume (ml) of the sample the absorbance of which is to be measured; |
| 120 | volume (μl) of the enzyme reaction mixture; |
| 5.5 | millimolar molecular extinction coefficient (/mM) of unsaturated uronic acid at 230 nm; |
| 105 | volume (μl) of the reaction mixture employed for dilution; |
| 0.01 | volume (ml) of the enzyme; and |
| 180 | reaction time (min). |

The protein is determined by measuring the absorbance of the enzyme solution at 280 nm and calculated by taking the absorbance of the 1 mg/ml protein solution as 1.0.

The fucoidan originating in Kjellmaniella crassifolia employed as the substrate is prepared in the following manner.

Dry Kjellmaniella crassifolia is ground with a free mill Model M-2 (mfd. by Nara Kikai Seisakusho) and treated in 10 times as much 85% methanol at 70° C. for 2 hours. Then it is filtered and the residue is further treated in 10 times as much methanol at 70° C. for 2 hours. After filtering, 20 times as much water is added to the residue. Then the mixture is treated at 100° C. for 3 hours and filtered to thereby give an extract. The salt concentration of the extract is adjusted to the same level as that of a 400 mM solution of sodium chloride. Then cetylpyridinium chloride is added thereto until no precipitate is formed any more. After centrifuging, the precipitate is thoroughly washed with ethanol to thereby completely eliminate the cetylpyridinium chloride. Next, it is subjected to desalting and the removal of low-molecular weight substances by using an ultrafilter (exclusion molecular weight of ultrafiltration membrane: 100,000, mfd. by Amicon). The precipitate thus formed is eliminated by centrifugation. The supernatant is freeze-dried to thereby give purified *Kjellmaniella crassifolia* fucoidan.

Analysis on the Structure of Enzyme Reaction Product:

The above-mentioned endofucoidanase is an enzyme which exclusively degrades the α 1→4 bond between D-mannose and D-glucuronic acid in the sulfated-fucose-containing polysaccharide-U. When the sulfated-fucose-containing polysaccharide-U obtained above is treated with this enzyme, oligosaccharides having the structures represented by the following formulae (I), (II) and (III) are formed:

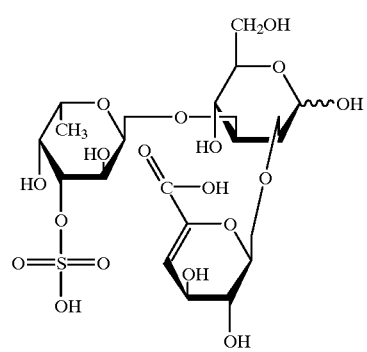
(I)

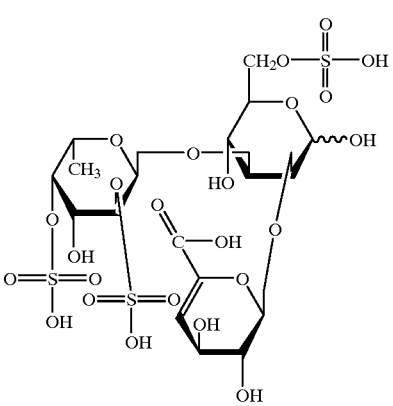
(II)

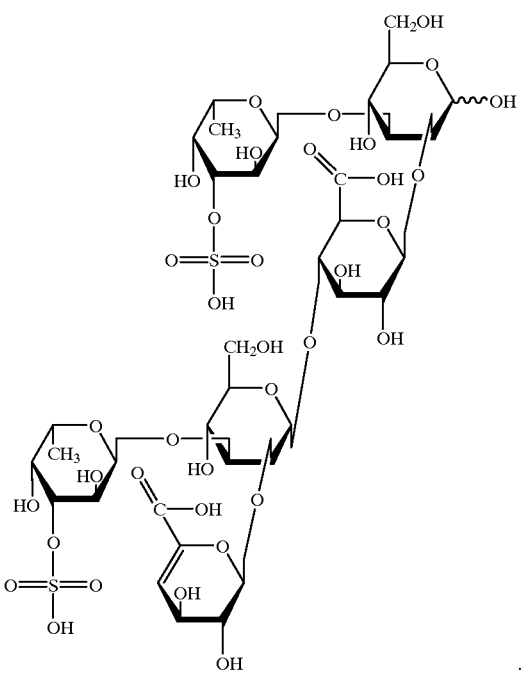
(III)

Now, detailed description will be given.

A portion of each of the above-mentioned three fractions (a), (b) and (c) separated and purified by DEAE-Sepharose FF is pyridyl-(2)-aminated (PA) at the reducing end by using GlycoTAG and GlycoTAG Reagent Kit to thereby give PA saccharides (PA-a), (PA-b) and (PA-c), which are then analyzed by HPLC.

The HPLC is effected under the following conditions:

(i) HPLC analysis by using molecular weight fractionation column:

| | |
|---|---|
| apparatus | Model L-6200 (mfd. by Hitachi, Ltd.); |
| column | SHODEX SB-803 (4.6 × 250 mm, mfd. by Showa Denko, K. K.); |
| eluent | 0.2M sodium chloride: dimethyl sulfoxide = 9:1; |
| detection | Fluorometric Detector F-1150 (mfd. by Hitachi, Ltd.), excitation wavelength: 320 nm, fluorescent wavelength: 400 nm; |
| flow rate | 1 ml/min; and |
| column temperature | 50° C. |

(ii) HPLC analysis with the use of reversed phase column:

| | |
|---|---|
| apparatus | Model L-6200 (mfd. by Hitachi, Ltd.); |
| column | L-column (4.6 × 250 mm, mfd. by Kagaku Yakuhin Kensa Kyokai); |
| eluent | 50 mM acetic acid-triethylamine (Ph 5.5); |
| detection | Fluorometric Detector F-1150 (mfd. by Hitachi, Ltd.), excitation wavelength: 320 nm, fluorescent wavelength: |

| | 400 nm; |
|---|---|
| flow rate | 1 ml/min; and |
| column temperature | 40° C. |

Figure 5:
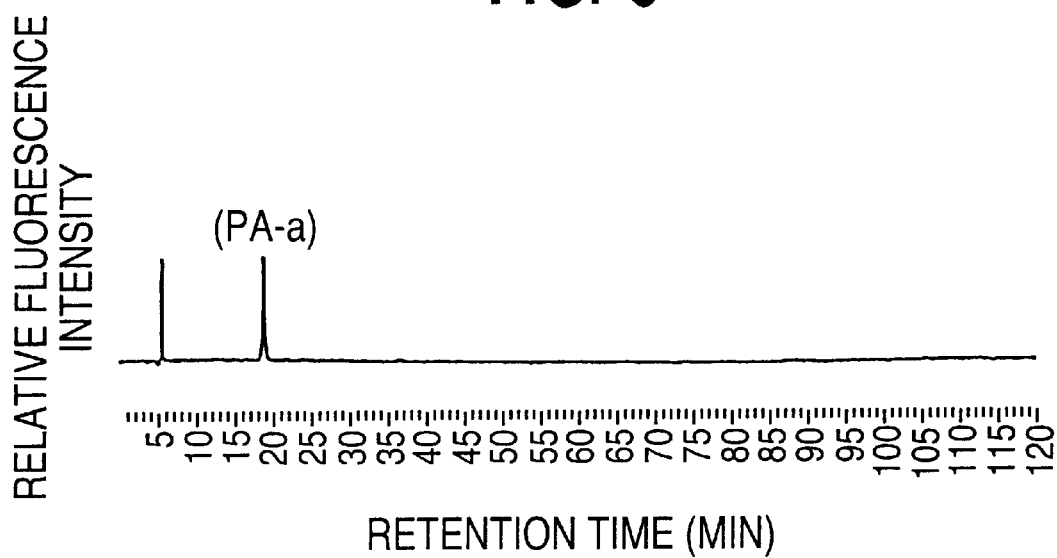
FIG. 5 shows the elution pattern of the saccharide compound (a) having been pyridyl-(2)-aminated (PA-a) which is eluted from an L-column.
Figure 6:
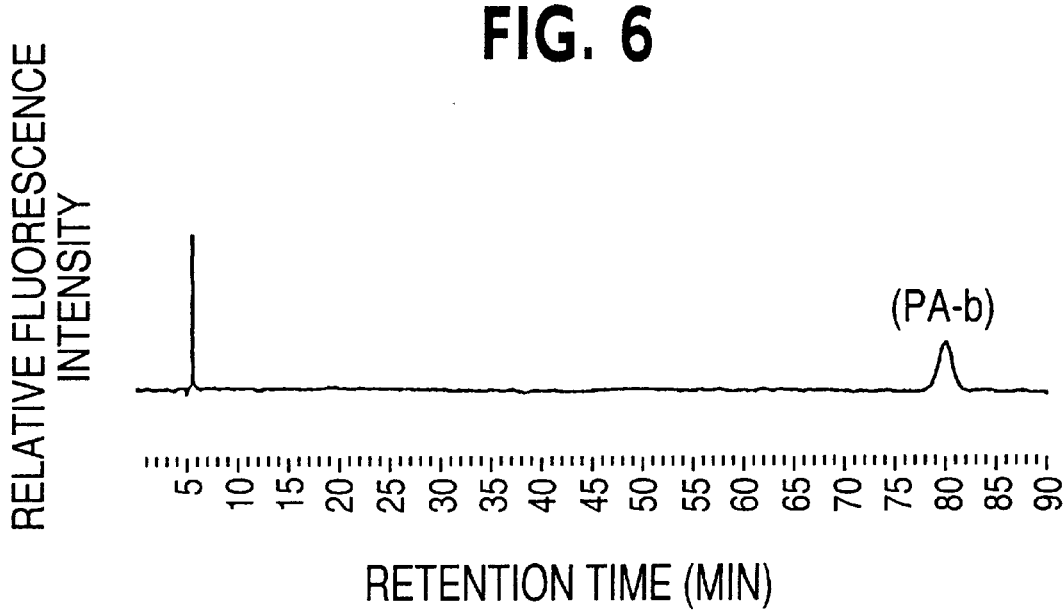
FIG. 6 shows the elution pattern of the saccharide compound (b) having been pyridyl-(2)-aminated (PA-b) which is eluted from an L-column.
Figure 7:
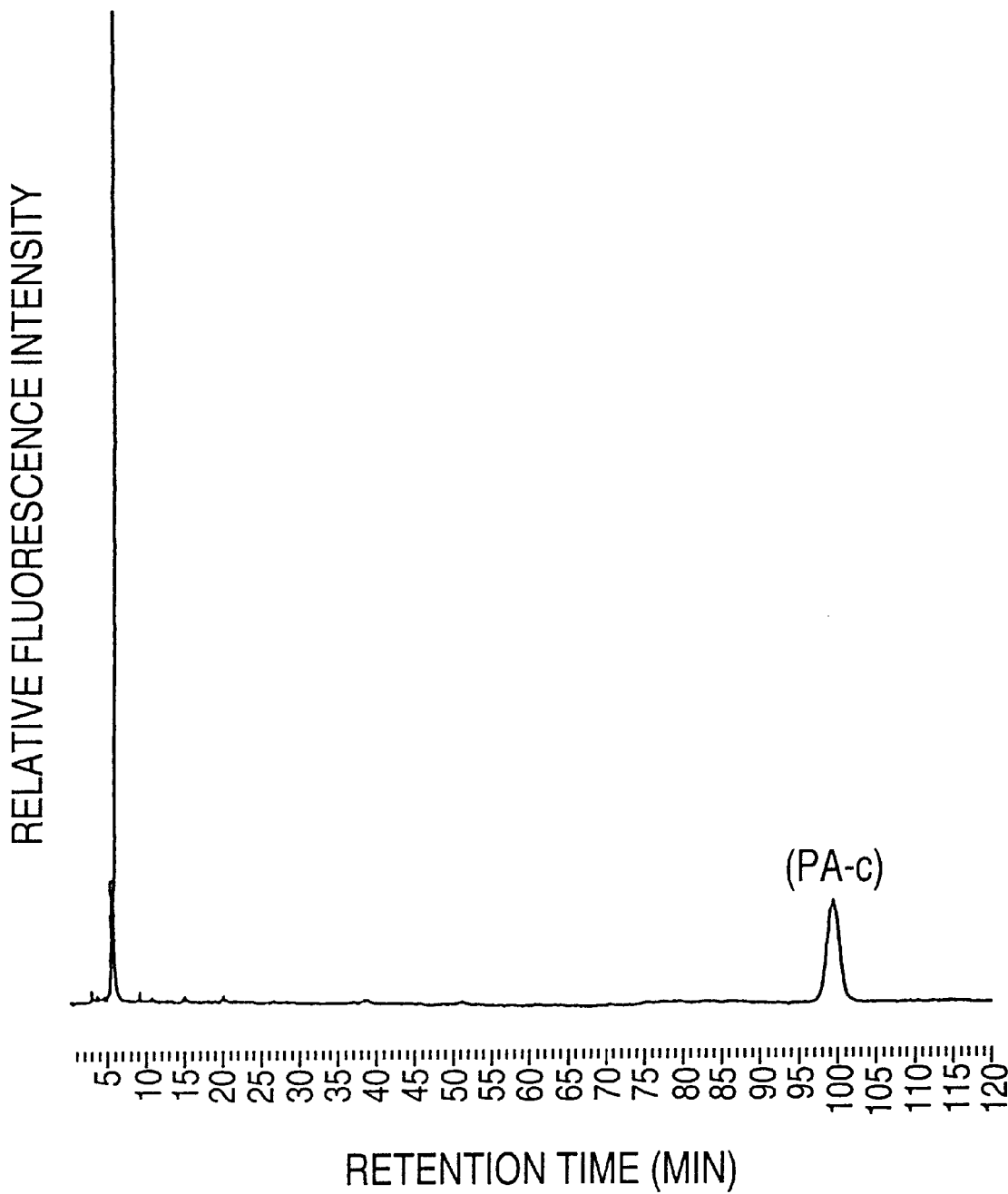
FIG. 7 shows the elution pattern of the saccharide compound (c) having been pyridyl-(2)-aminated (PA-c) which is eluted from an L-column.
Figure 8:
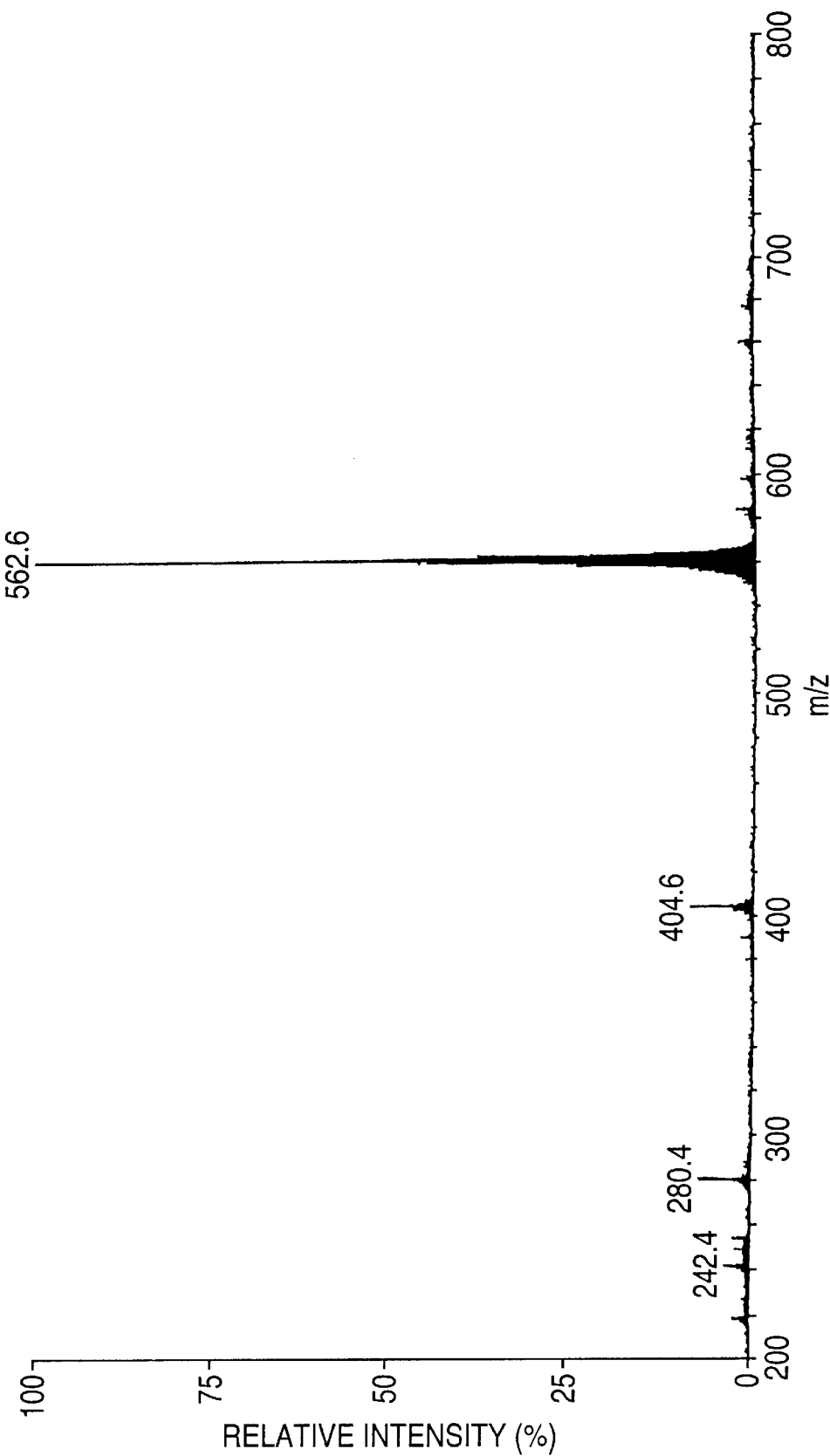
FIG. 8 is the mass spectrogram (negative measurement) of the saccharide compound (a).
Figure 9:
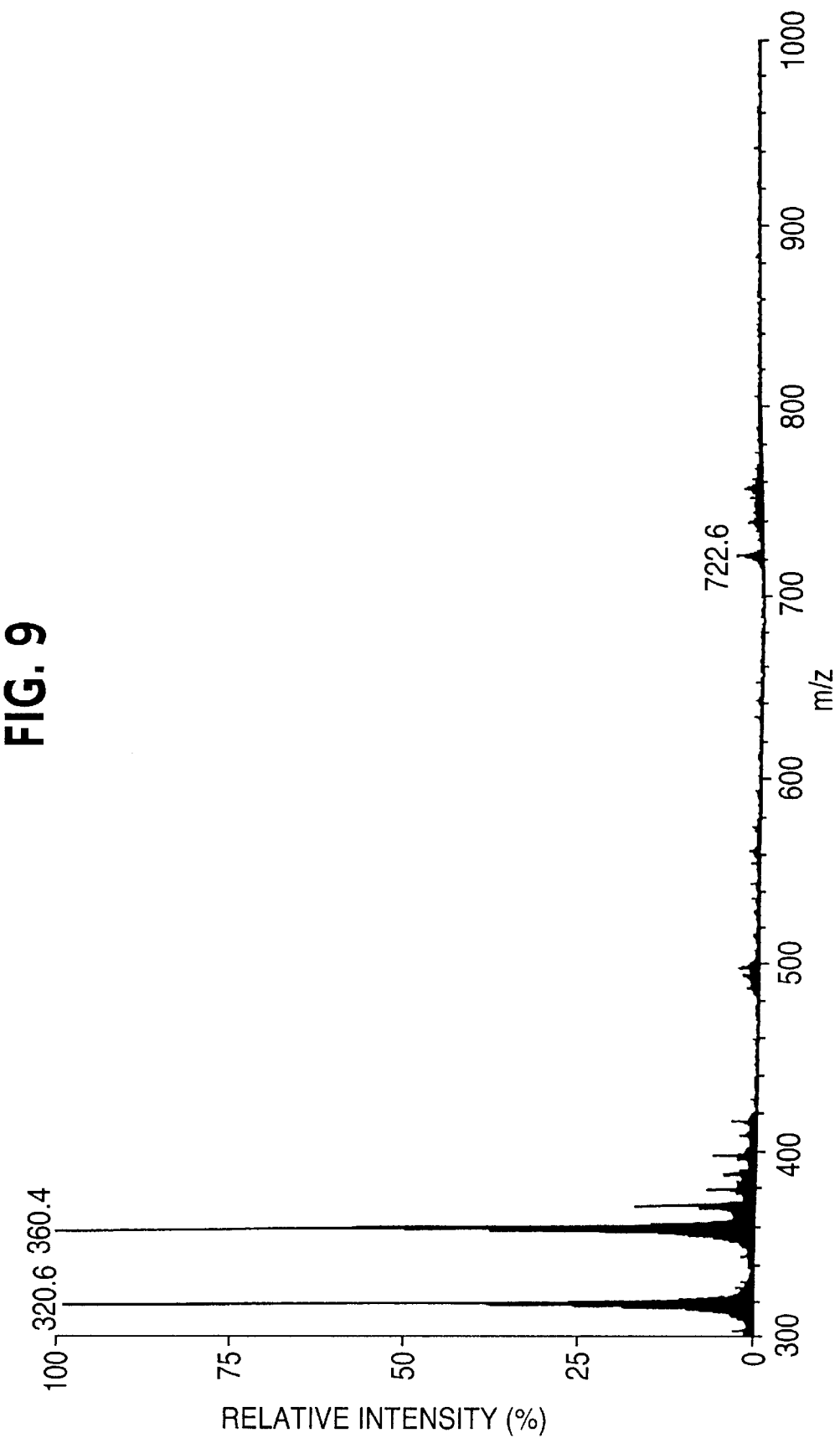
FIG. 9 is the mass spectrogram (negative measurement) of the saccharide compound (b).
Figure 10:
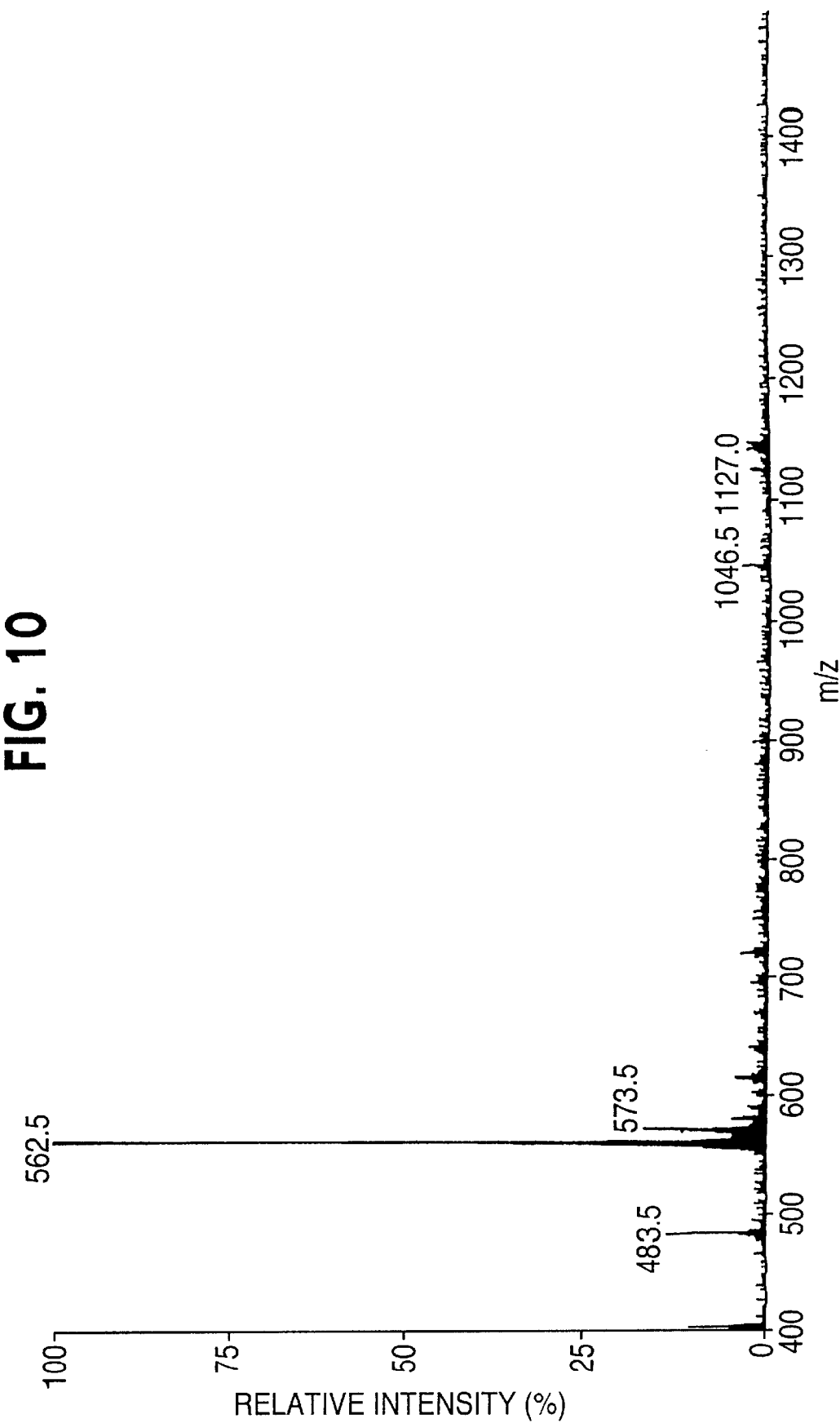
FIG. 10 is the mass spectrogram (negative measurement) of the saccharide compound (c).

FIGS. 5, 6 and 7 respectively show the HPLC elution patterns of the pyridyl-(2)-aminated saccharide compounds (PA-a), (PA-b) and (PA-c). In each figure, the ordinate refers to the relative fluorescence intensity while the abscissa refers to the retention time (min).

Next, the physical properties of the compounds (a), (b) and (c), i.e., those represented by the formulae (I), (II) and (II) will be illustrated.

Figure 11:
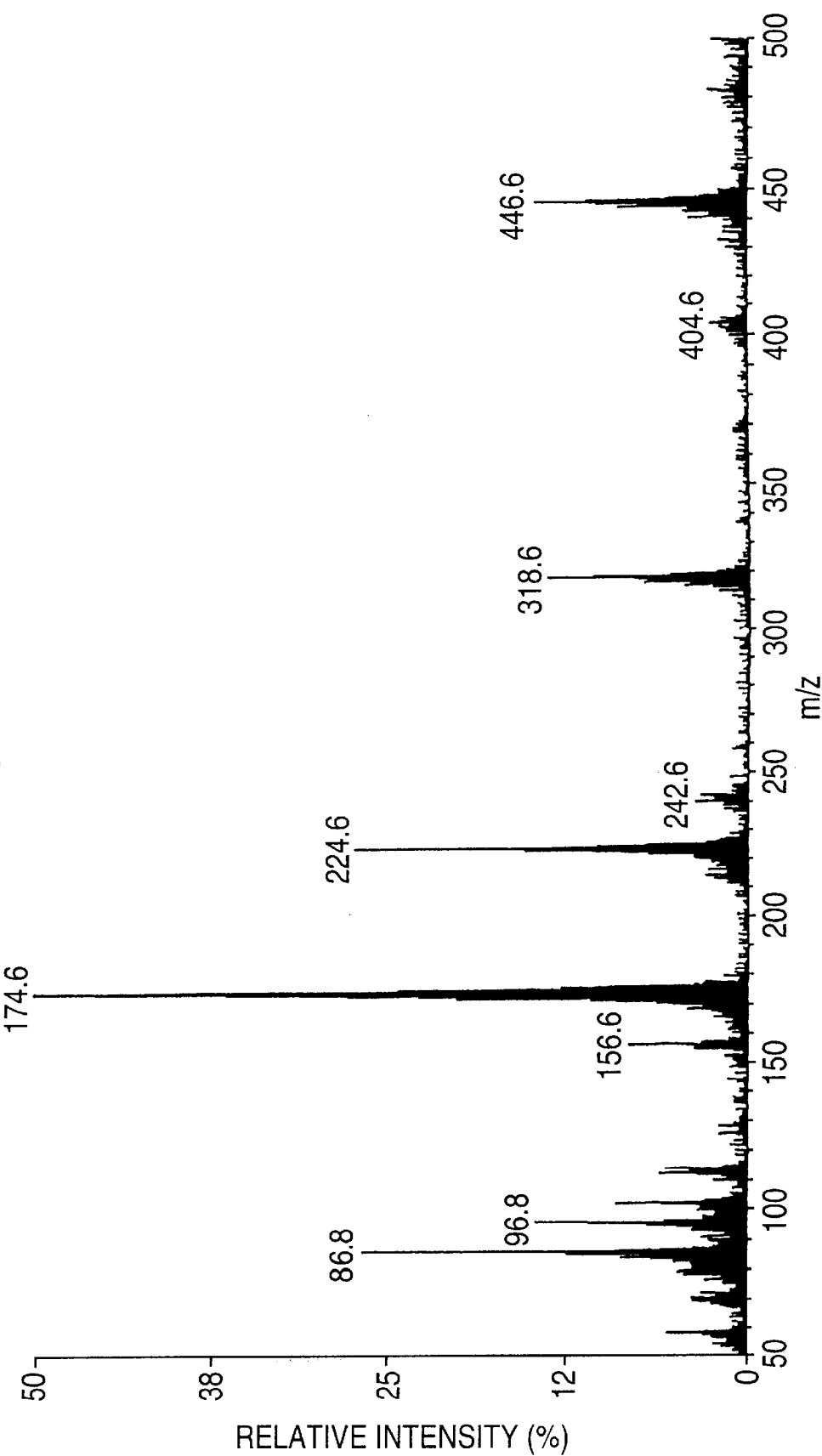
FIG. 11 is the mass-mass spectrogram (negative measurement) of the saccharide compound (a).
Figure 12:
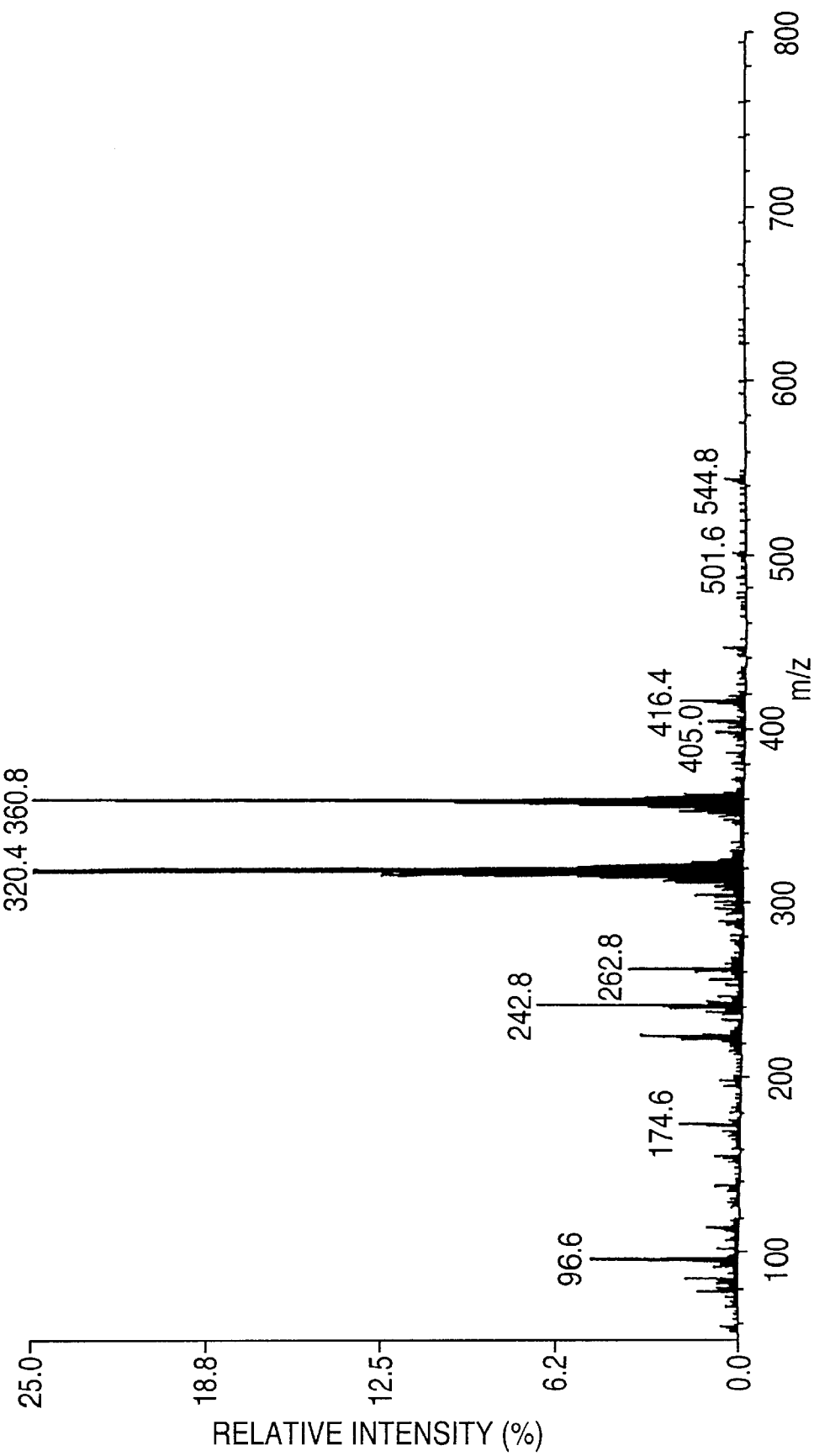
FIG. 12 is the mass-mass spectrogram (negative measurement) of the saccharide compound (b).
Figure 13:
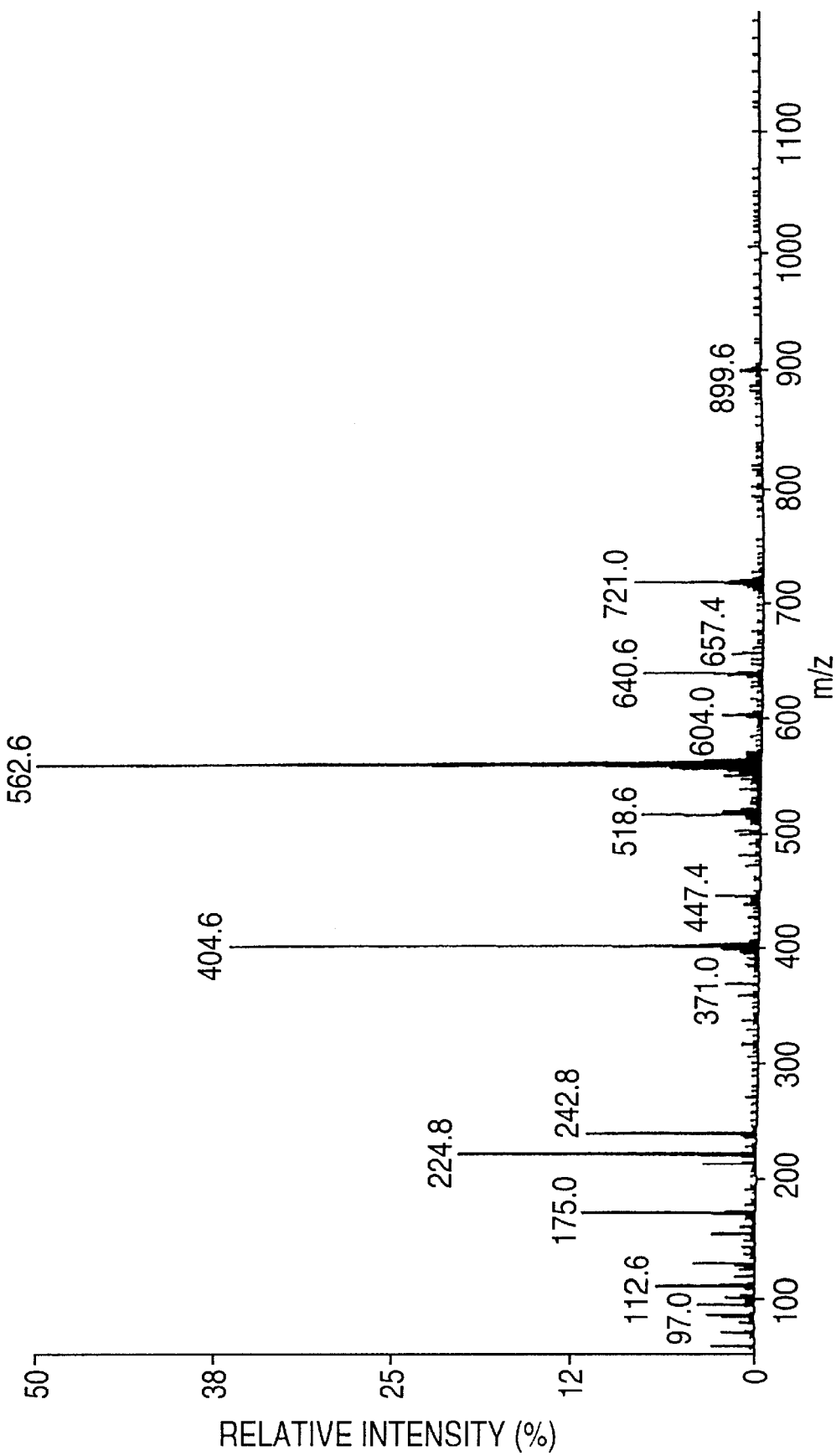
FIG. 13 is the mass-mass spectrogram (negative measurement) of the saccharide compound (c).

FIGS. (8), (9) and (10) respectively show the mass spectra of the compounds (a), (b) and (c), while FIGS. 11, 12 and 13 respectively show the mass-mass spectra of the compounds (a), (b) and (c). In each figure, the ordinate refers to the relative intensity (%) while the abscissa refers to the m/z value.

Figure 14:
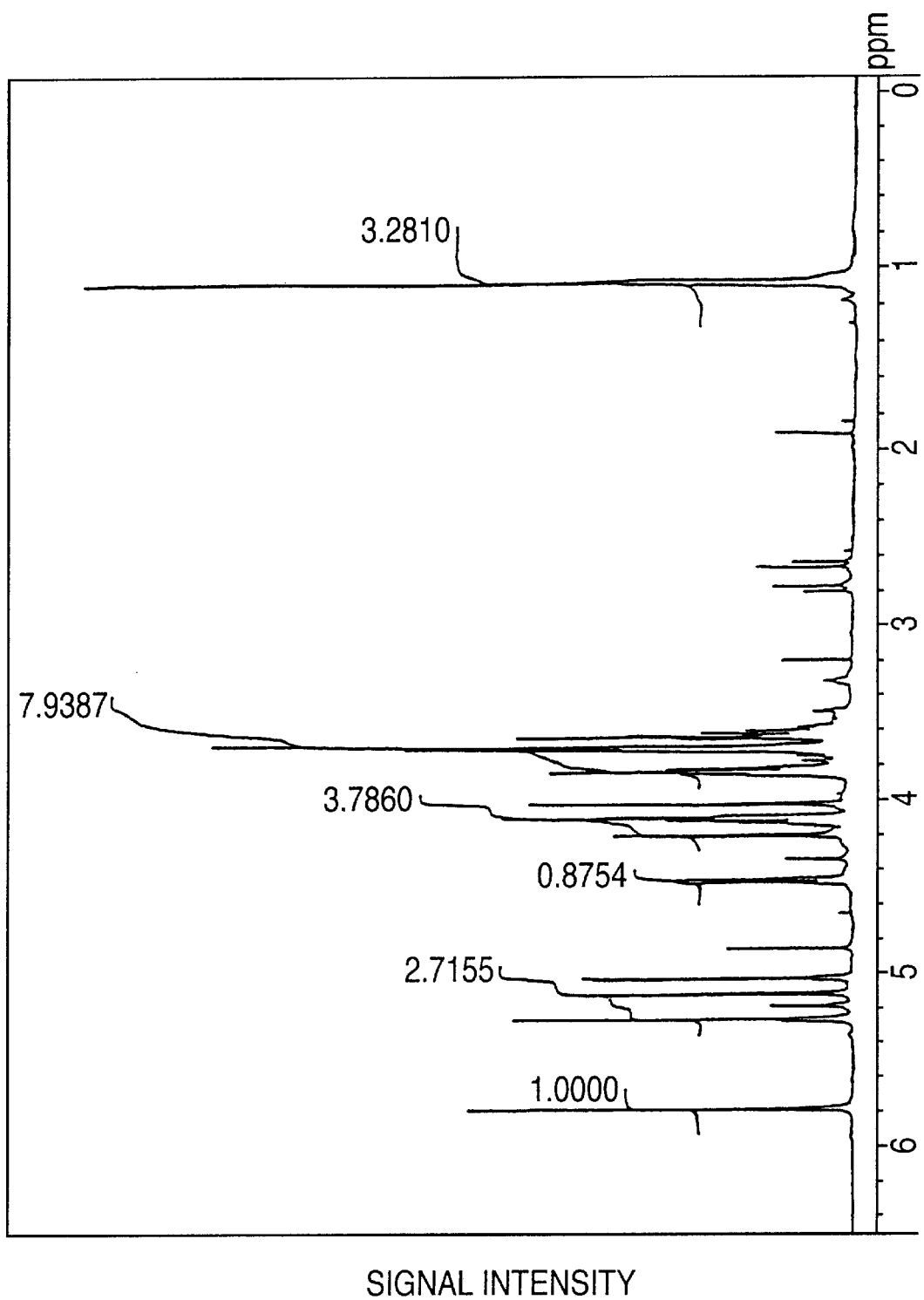
FIG. 14 is the $^1$H-NMR spectrum of the saccharide compound (a).
Figure 15:
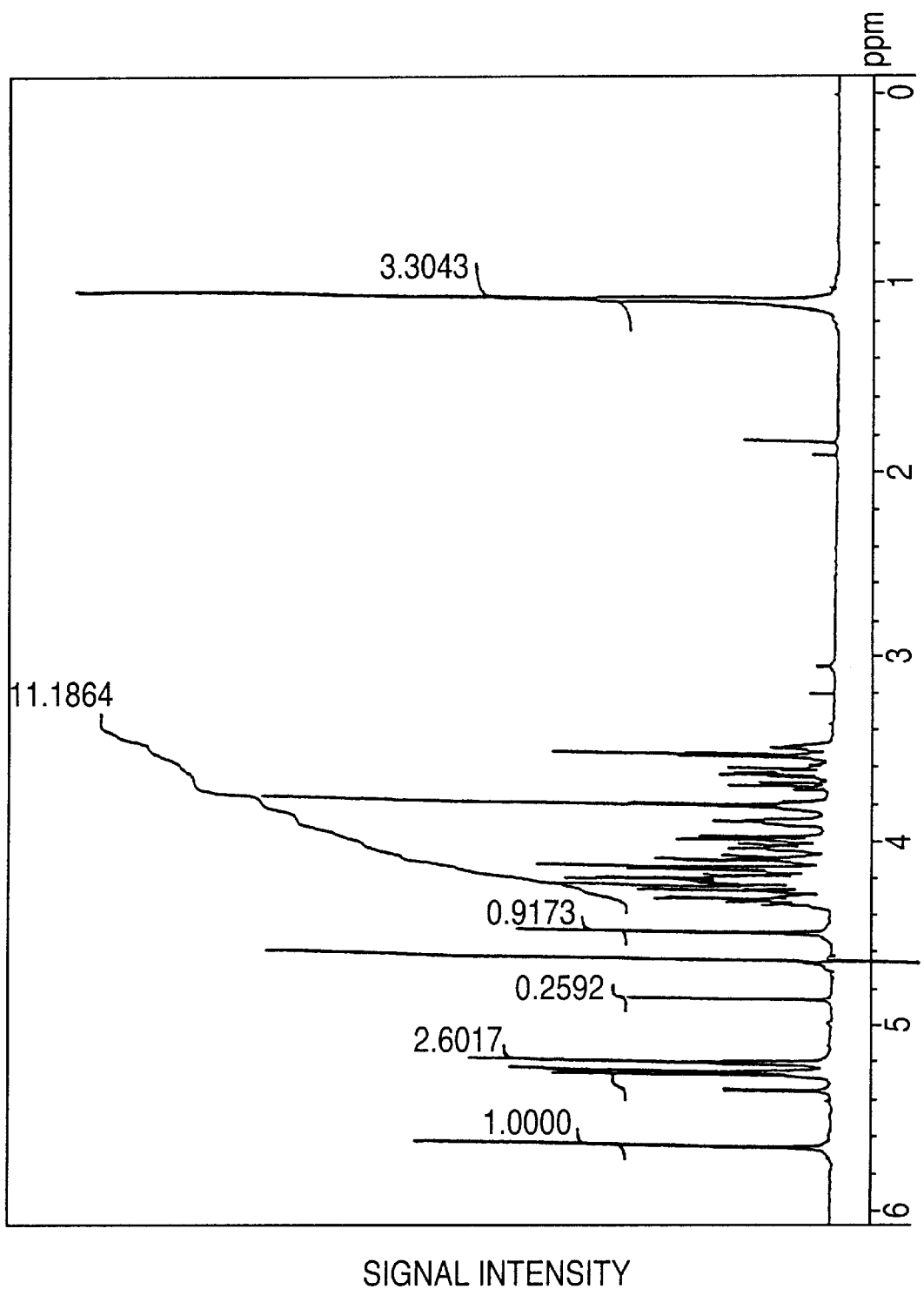
FIG. 15 is the $^1$H-NMR spectrum of the saccharide compound (b).
Figure 16:
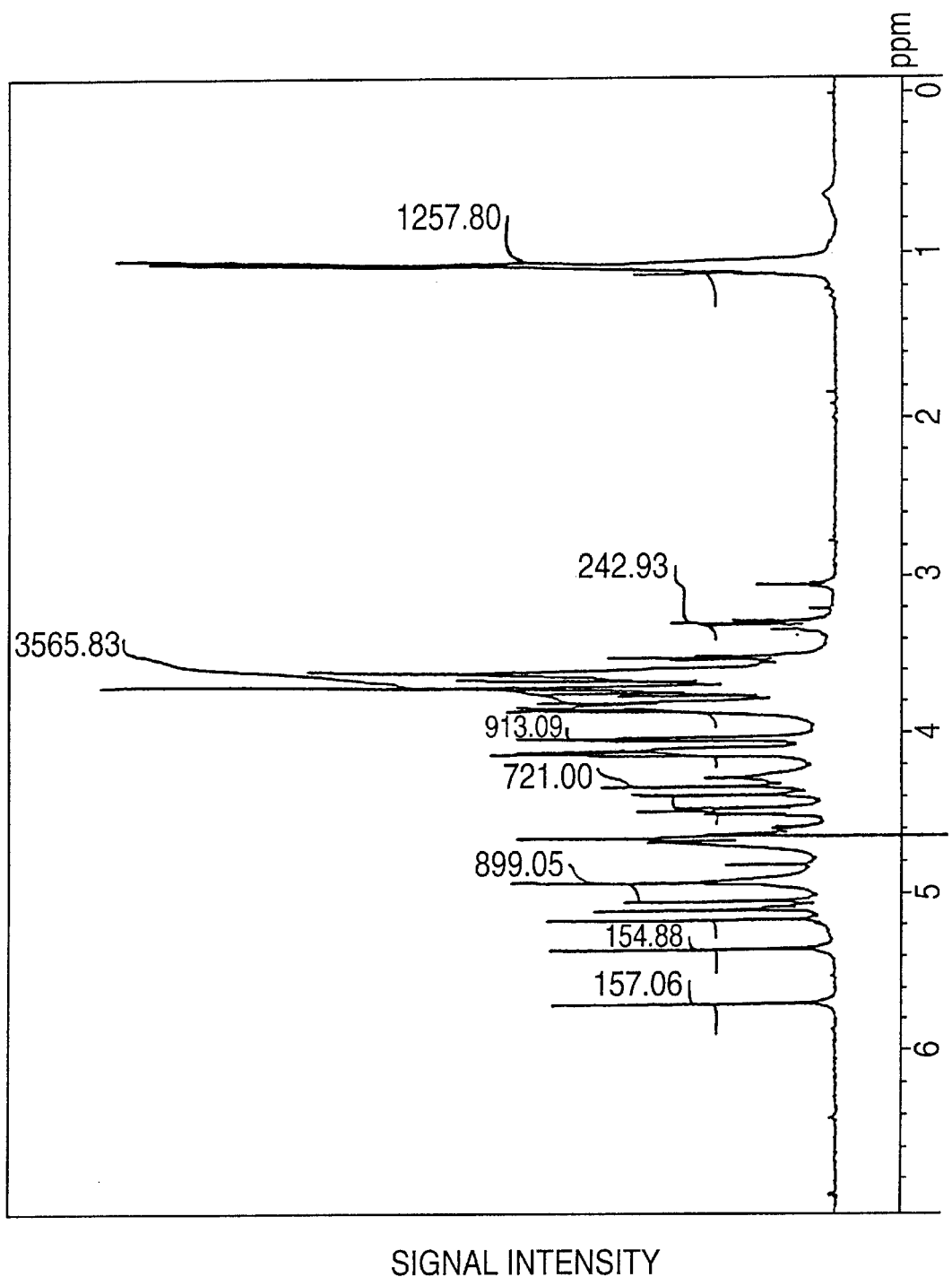
FIG. 16 is the $^1$H-NMR spectrum of the saccharide compound (c).

Moreover, FIGS. 14, 15 and 16 respectively show the $^1$H-NMR spectra of the compounds (a), (b) and (c). In each figure, the ordinate refers to the signal intensity while the abscissa refers to the chemical shift (ppm).

The chemical shifts in $^1$H-NMR are expressed by taking the chemical shift of HOD as 4.65 ppm.

Physical properties of the compound (a):

Molecular weight: 564. MS m/z: 563 [M-H$^+$]$^-$. MS/MS m/z: 97 [HSO$_4$]$^-$, 157 [unsaturated D-glucuronic acid-H$_2$O—H$^+$]$^-$, 175 [unsaturated D-glucuronic acid-H$^+$]$^-$, 225 [L-fucose sulfate-H$_2$O—H$^+$]$^-$, 243 [L-fucose sulfate-H$^+$]$^-$, 319 [unsaturated D-glucuronic acid bonded to D-mannose-H$_2$O—H$^+$]$^-$, 405 [M-unsaturated D-glucuronic acid-H$^+$]$^-$, 483 [M-SO$_3$—H$^+$]$^-$.

$^1$H-NMR (D$_2$O); δ 5.78(1H, d, J=3.7 Hz, 4"-H), 5.26(1H, d, J=1.2 Hz, 1-H), 5.12(1H, d, J=4.0 Hz, 1'-H), 5.03(1H, d, J=6.1 Hz, 1"-H), 4.47(1H, d-d, J=3.4, 10.4 Hz, 3'-H), 4.21 (1H, br-s, 2-H), 4.12(1H, m, 5'-H), 4.10(1H, d-d, J=3.7, 5.8 Hz, 3"-H), 4.03(1H, d, J=3.4 Hz, 4'-H), 3.86(1H, m, 3-H), 3.83(1H, d-d, J=4.0, 10.4 Hz, 2'-H), 3.72(1H, m, 4-H), 3.72(1H, m, 5-H), 3.70(H$_2$ of 2H, m, 5-CH$_2$), 3.65(1H, d-d, J=5.8, 6.1 Hz, 2"-H), 1.08(H$_3$ of 3H, d, J=6.7 Hz, 5'-CH$_3$).

Saccharide Composition:

L-fucose:unsaturated D-glucuronic acid:D-mannose= 1:1:1 (each one molecule).

Sulfate:

one molecule (at the 3-position of L-fucose).

The peaks in $^1$H-NMR are assignable respectively to the positions shown by the numerical values in the following formula (IV):

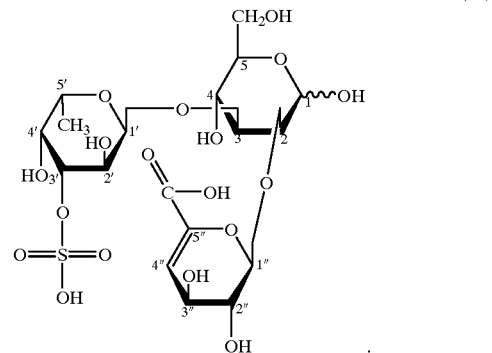

(IV)

Physical properties of the compound (b):

Molecular weight: 724. MS m/z: 723 [M-H$^+$]$^-$, 361 [M-2H$^+$]$^{2-}$. MS/MS m/z: 97 [HSO$_4$]$^-$, 175 [unsaturated D-glucuronic acid-H$^+$]$^-$, 243 [L-fucose sulfate-H$^+$]$^-$, 321 [M-SO$_3$-2H$^+$]$^{2-}$, 405 [M-unsaturated D-glucuronic acid-2SO$_3$-H$^+$]$^-$, 417 [M-L-fucose-2SO$_3$-H$^+$]$^-$.

$^1$H-NMR (D$_2$O); δ 5.66(1H, d, J=3.4 Hz, 4"-H), 5.27(1H, d, J=7.3 Hz, 1"-H), 5.22(1H, d, J=1.8 Hz, '-H), 5.21(1H, d, J=3.7 Hz, 1'-H), 4.50(1H, d, J=3.1 Hz, 4'-H), 4.32(1H, q, J=6.7 Hz, 5'-H), 4.27(1H, d-d, J=3.7, 10.4 Hz, 2'-H), 4.21 (1H, d-d, J=3.4, 6.7 Hz, 3"-H), 4.18(H of 1H, d-d, J=1.8, 11.0 Hz, 5-CH), 4.15(1H, br-s, 2-H), 4.10(H of 1H, d-d, J=5.8, 11.0 Hz, 5-CH), 3.99(1H, d-d, J=3.1, 10.4 Hz, 3'-H), 3.90(1H, m, 5-H), 3.82(1H, m, 3-H), 3.82(1H, m, 4-H), 3.54(1H, br-t, J=7.3 Hz, 2"-H), 1.11(H$_3$ of 3H, d, J=6.7 Hz, 5'-CH$_3$).

Saccharide Composition:

L-fucose:unsaturated D-glucuronic acid:D-mannose= 1:1:1 (each one molecule).

Sulfate:

three molecules (at the 2- and 4-positions of L-fucose and the 6-position of D-mannose).

The peaks in $^1$H-NMR are assignable respectively to the positions shown by the numerical values in the following formula (V):

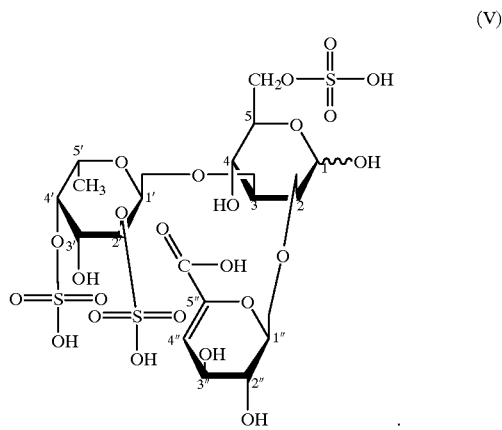

(V)

Physical properties of the compound (c):

Molecular weight: 1128. MS m/z: 1127 [M-H$^+$]$^-$. MS/MS m/z: 97 [HSO$_4$]$^-$, 175 [unsaturated D-glucuronic acid-H$^+$]$^-$, 225 [L-fucose sulfate-H$_2$O-H$^+$]$^-$, 243 [L-fucose sulfate-H$^+$]$^-$, 371 [M-unsaturated D-glucuronic acid-L-fucose-SO$_3$-2H$^+$]$^{2-}$, 405 [sulfated L-fucose bonded to D-mannose-H$^+$]$^-$, 721 [M-D-mannose-L-fucose-SO$_3$-H$_2$O-H$^+$]$^-$.

$^1$H-NMR (D$_2$O); δ 5.69(1H, d, J=3.7 Hz, (4)"-H), 5.34 (1H, s, (1)-H), 5.16(1H, s, 1-H), 5.10(1H, d, J=4.0 Hz, (1)'-H), 5.50(1H, d, J=3.7 Hz, 1'-H), 4.93(1H, d, J=6.4 Hz, (1)"-H), 4.50(1H, d-d, J=3.4, 10.7 Hz, 3'-H), 4.47(1H, d-d, J=3.4, 10.4 Hz, (3)'-H), 4.39(1H, d, J=7.9 Hz, 1"-H), 4.33 (1H, br-s, (2)-H), 4.14(1H, m, 2-H), 4.12(1H, m, (3)"-H), 4.12(1H, m, 5'-H), 4.12(1H, m, (5)'-H), 4.04(1H, m, 4'-H), 4.03(1H, m, (4)'-H), 3.85(1H, m, 2'-H), 3.85(1H, m, (2)'-H), 3.82(1H, m, 3-H), 3.82(1H, m, (3)-H), 3.73(1H, m, 4-H), 3.73(1H, m, 5-H), 3.73(1H, m, (4)-H), 3.70(H$_2$ of 2H, m, 5-CH$_2$), 3.70(H$_2$ of 2H, m, (5)-CH$_2$), 3.67(1H, m, 5"-H), 3.62(1H, m, 4"-H), 3.62(1H, m, (2)"-H), 3.62(1H, m, (5)-H), 3.51(1H, t, J=8.9 Hz, 3"-H), 3.28(1H, t, J=7.9 Hz, 2"-H), 1.09(H$_3$ of 3H, d, J=6.7 Hz, (5)'-CH$_3$), 1.07(H$_3$ of 1H, d, J=6.7 Hz, 5'-CH$_3$).

Saccharide composition:

L-fucose:unsaturated D-glucuronic acid:D-glucuronic acid:D-mannose=2:1:1:2 (two L-fucose molecules, two D-mannose molecules, one unsaturated D-glucuronic acid molecule and one D-glucuronic acid molecule).

Sulfate:

two molecules (at the 3-position of each L-fucose).

The peaks in $^1$H-NMR are assignable respectively to the positions shown by the numerical values in the following formula (V):

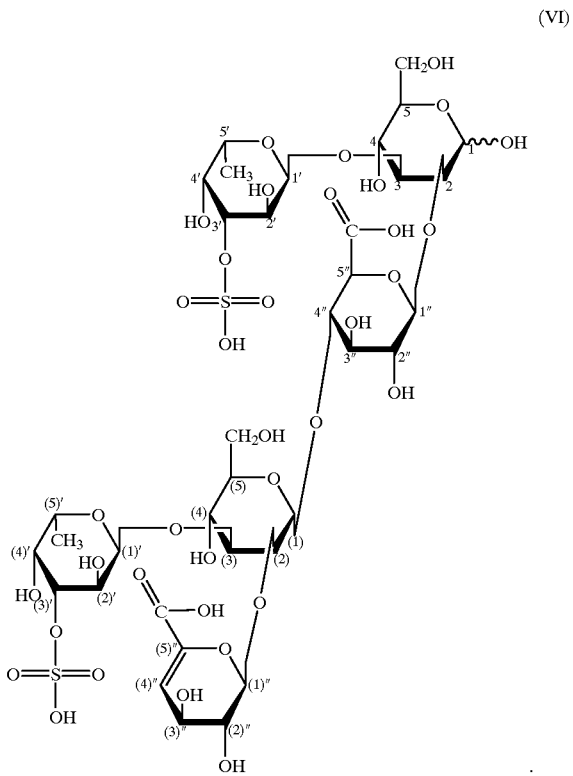

(VI)

When the sulfated-fucose-containing polysaccharide-U thus obtained is treated with the above-mentioned endofucoidanase, elimination occurs as the reaction proceeds and thus the absorbance at 230 nm is increased. All of the main reaction products carry unsaturated hexuronate groups, which suggests that the obtained sulfated-fucose-containing polysaccharide-U has a sugar chain composed of hexuronic acid and mannose alternately bonded to each other. Because of containing fucose as the main constituting saccharide, the obtained sulfated-fucose-containing polysaccharide-U is liable to be degraded with acids, compared with common polysaccharides. On the other hand, it is known that the bonds of hexuronic acids and mannose are relatively highly tolerant to acids. The present inventors have attempted to identify the hexuronic acid in the sugar chain which is composed of hexuronic acid and mannose alternately bonded to each other and contained in the sulfated-fucose-containing polysaccharide mixture originating in *Kjellmaniella crassifolia* in the following manner with reference to the method described in Carbohydrate Research, 125, 283–290 (1984). First, the sulfated-fucose-containing polysaccharide mixture is dissolved in 0.3 M oxalic acid and treated at 100° C. for 3 hours. Then it is subjected to molecular weight fractionation and fractions of molecular weight of 3,000 or more are combined. Then it is further treated with an anion exchange resin and the adsorbed matters are collected. The substance thus obtained is freeze-dried and hydrolyzed with 4 N hydrochloric acid. After adjusting the pH value to 8, it is pyridyl-(2)-aminated and uronic acid is analyzed by HPLC. The HPLC is effected under the following conditions:

| | |
|---|---|
| apparatus | Model L-6200 (mfd. by Hitachi, Ltd.); |
| column | PALPAK Type N (4.6 mm × 250 mm, mfd. by Takara Shuzo, Co., Ltd.); |
| eluent | 200 mM acetic acid triethylamine buffer (pH 7.3): acetonitrile = 25:75; |
| detection | Fluorometric Detector F-1150 (mfd. by Hitachi, Ltd.), excitation wavelength: 320 nm, fluorescent wavelength: 400 nm; |
| flow rate | 0.8 ml/min; |
| column temperature | 40° C. |

As the standards for PA hexuronic acids, use is made of those prepared by pyridyl-(2)-aminated glucuronic acid manufactured by Sigma Chemical Co., galacturonic acid manufactured by Wako Pure Chemical Industries, Ltd., induronic acid obtained by hydrolyzing 4-methylumbelliferyl-α-L-iduronide manufactured by Sigma Chemical Co., and mannuronic acid and guluronic acid obtained by hydrolyzing alginic acid (mfd. by Wako Pure Chemical Industries, Ltd.) followed by the separation with an anion exchange resin with reference to the method described in Acta Chemica Scandinavica, 15, 1397–1398 (1961).

As a result, it is found out that glucuronic acid alone is contained as the hexuronic acid in the sugar chain in the above-mentioned sulfated-fucose-containing polysaccharide mixture.

Further, the glucuronic acid in the hydrolyzate of the above-mentioned sugar chain is separated from D-mannose by using an anion exchange resin and freeze-dried. Then the specific rotation thereof is measured. It is thus clarified that the glucuronic acid is a dextrorotatory one, i.e., D-glucuronic acid.

Further, the sulfated-fucose-containing polysaccharide mixture originating in *Kjellmaniella crassifolia* is treated with the above-mentioned endofucoidanase and then hydrolyzed with the use of oxalic acid similar to the above case. However, no polymer having D-glucuronic acid and D-mannose alternately bonded to each other is found out. Based on these results, it is clarified that the above-mentioned endofucoidanase cleaves via the elimination reaction sulfated-fucose-containing polysaccharides having a skeleton structure composed of D-glucuronic acid and D-mannose alternately bonded to each other.

Further, the polymer obtained by the degradation with oxalic acid is subjected to NMR analysis to thereby examine the anomeric configuration of the binding sites of D-glucuronic acid and D-mannose and the glycoside bond.

The NMR analytical data of the polymer are as follows. The chemical shifts in $^1$H-NMR are expressed by taking the chemical shift of the methyl group in triethylamine as 1.13 ppm, while those in $^{13}$C-NMR are expressed by taking the chemical shift of the methyl group in triethylamine as 9.32 ppm.

$^1$H-NMR (D$_2$O); δ 5.25(1H, br-s, 1-H), 4.32(1H, d, J=7.6 Hz, 1'-H), 4.00(1H, br-s, 2-H), 3.71(1H, m, 5'-H), 3.69(H of 1H, m, 5-CH), 3.68(1H, m, 3-H), 3.63(H of 1H, m, 5-CH), 3.63(1H, m, 4'-H), 3.57(1H, m, 4-H), 3.54(1H, m, 3'-H), 3.53(1H, m, 5-H), 3.25(1H, t, J=8.5 Hz, 2'-H).

$^{13}$C-NMR (D$_2$O); δ 175.3 (C of 5'-COOH), 102.5(1'-C), 99.6(1-C), 78.5(2-C), 77.9(4'-C), 77.0(3'-C), 76.7(5'-C), 73.9(5-C), 73.7(2'-C), 70.6(3-C), 67.4(4-C), 61.0(C of 5-CH$_2$OH).

The peaks are assignable respectively to the positions shown by the numerical values in the following formula (VII):

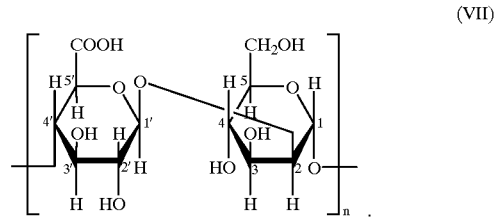

(VII)

Regarding the configuration at the 1-position of the D-glucuronic acid, it is identified as βD-glucuronic acid because of its vicinal binding constant of 7.6 Hz.

Regarding the configuration at the 1-position of the D-mannose, it is identified as α-D-mannose because of its chemical shift of 5.25 ppm.

The binding manners of the constituting saccharides are analyzed by the HMBC method, i.e., the $^1$H-heteronculear bond detection method. The DQF-COSY and HOHAHA methods are employed in the assignment in $^1$H-NMR while the HSQC method is employed in the assignment in $^{13}$C-NMR.

In the HMBC spectrum, crossed peaks are observed between 1-H and 4'-C with between 4'-H and 1-C, and between 1'-H and 2-C with between 2-H and 1'-C. These facts indicate that D-glucose is bonded to the 2-position of D-mannose via a β-bond while D-mannose is bonded to the 4-position of D-glucuronic acid via an α-bond.

By taking the above-mentioned results together into consideration, it is revealed that the compound (a) has a structure wherein unsaturated D-glucuronic acid and L-fucose having a sulfate group bonded thereto are bonded to D-mannose which is the reducing end; the compound (b) has a structure wherein unsaturated D-glucuronic acid and L-fucose having two sulfate groups bonded thereto are bonded to D-mannose which is the reducing end and has a sulfate group bonded thereto; and the compound (c) has a structure wherein D-glucuronic acid and L-fucose having a sulfate group bonded thereto are bonded to D-mannose which is the reducing end, and to this D-glucuronic acid is bonded D-mannose and, in turn, to this D-mannose are further bonded unsaturated D-glucuronic acid and L-fucose having a sulfate group bonded thereto.

As discussed above, the obtained sulfated-fucose-containing polysaccharide-U has a structure wherein D-glucuronic acid and D-mannose are alternately bonded to each other and L-fucose is bonded to at least one D-mannose.

Also, it has a partial structure represented by the following general formula (VIII) wherein at least one of alcoholic hydroxyl groups has been sulfated and n stands for an integer of 1 or more:

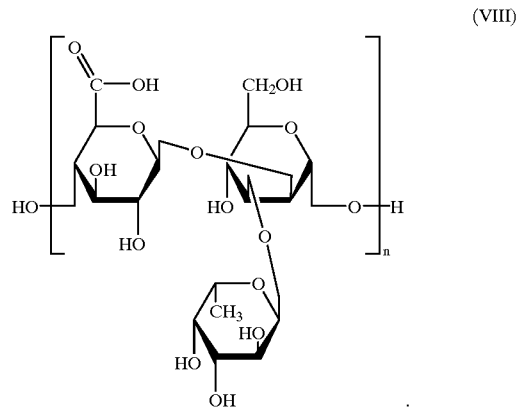

(VIII)

The present invention provides the sulfated-fucose-containing polysaccharide-U which has been separated from the sulfated-fucose-containing polysaccharide-F of the present invention and purified. The sulfated-fucose-containing polysaccharide-U of the present invention contains uronic acid as its constituting saccharide and is degraded by the fucoidanase produced by Flavobacterium sp. SA-0082 (FERM BP-5402) to thereby give at least one compound selected from those represented by the above formulae (I), (II) and (III). The sulfated-fucose-containing polysaccharide-U of the present invention is not restricted in the molecular weight, molecular weight distribution or saccharide composition. Namely, sulfated-fucose-containing polysaccharide-U having arbitrary molecular weight and molecular weight distribution may be prepared and sulfated-fucose-containing polysaccharides having definitely clarified physicochemical properties can be provided.

The sulfated-fucose-containing polysaccharide-U of the present invention has no such potent anticoagulant effect as the one shown by the sulfated-fucose-containing polysaccharide-F. Thus sulfated-fucose-containing polysaccharides substantially showing no anticoagulant activity can be provided. The sulfated-fucose-containing polysaccharide-U of the present invention is usable, as purified sulfated-fucose-containing polysaccharides, in anti-cancer agents, antimetastatic agents, carcinostatic agents and the like. Also, it is useful as an antigen against an anti-sulfated-fucose-containing polysaccharide antibody. It is also possible to produce oligosaccharides such as those having the structures of the above formulae (I), (II) and (III) from the sulfated-fucose-containing polysaccharide-U. Namely, it is useful in the production of these novel compounds.

Next, the sulfated-fucose-containing polysaccharide-F of the present invention and a method for producing the same will be described.

The sulfated-fucose-containing polysaccharide-F of the present invention may be produced by using the method of the present invention in the following manner. A sulfated-fucose-containing polysaccharide mixture is treated with a degrading enzyme capable of degrading the sulfated-fucose-containing polysaccharide-U. After the completion of the enzymatic reaction, the sulfated-fucose-containing polysaccharide-U thus degraded is eliminated by ultrafiltration, etc. As the above-mentioned degrading enzyme, any enzyme may be used so long as it can selectively degrade the sulfated-fucose-containing polysaccharide-U. As a particular example thereof, citation can be made of the above-mentioned endofucoidanase produced by Flavobacterium sp. SA-0082 (FERM BP-5402).

In the treatment with this enzyme, the substrate concentration, temperature, pH value, etc. may be appropriately selected so that the enzymatic reaction can proceed advantageously. It is usually desirable that the substrate concentration ranges from about 0.1 to 10%, the temperature ranges from about 20 to 40° C. and the pH value ranges from about 6 to 9.

It is also possible that a microorganism capable of producing a degrading enzyme having the ability to degrade the sulfated-fucose-containing polysaccharide-U is incubated in a medium to which a sulfated-fucose-containing polysaccharide mixture has been added and then the sulfated-fucose-containing polysaccharide-F is purified from the medium. The microorganism to be used therefor may be an arbitrary one, so long as it is capable of producing a degrading enzyme having the ability to degrade the sulfated-fucose-containing polysaccharide-U. As a particular example thereof, citation can be made of Flavobacterium sp. SA-0082 (FERM BP-5402) as described above and *Fucoidanobacter marinus* SI-0098 (FERM BP-5403).

The nutrients to be added to the medium may be arbitrary ones so long as the strain employed can utilize them so as to produce the degrading enzyme. Appropriate examples of the carbon source include fucoidan, marine alga powder, alginic acid, fucose, glucose, mannitol, glycerol, saccharose, maltose, lactose and starch, while appropriate examples of the nitrogen source include yeast extract, peptone, casamino acids, corn steep liquor, meat extract, defatted soybean, ammonium sulfate and ammonium chloride. The medium may further contain inorganic matters and metal salts such as sodium salts, phosphates, potassium salts, magnesium salts and zinc salts.

Needless to say, the incubation conditions should be selected depending on the strain employed, the medium composition, etc. so that the activity of degrading the sulfated-fucose-containing polysaccharide-U can attain the maximum level. Generally speaking, the incubation may be effected at a temperature of from 15 to 30° C. and at a pH value of the medium of 5 to 9 under aeration/agitation for 5 to 72 hours. After the completion of the incubation, the components in the medium other than the sulfated-fucose-containing polysaccharide-F, namely, the sulfated-fucose-containing polysaccharide-U thus degraded, etc. may be eliminated by, for example, ultrafiltration.

This strain *Fucoidanobacter marinus* SI-0098, which was isolated by the present inventors from seawater in Aomori, has the following mycological properties.

1. *Fucoidanobacter marinus* SI-0098 strain
a. Morphological properties (1) Diplococcus (short rod);

| | |
|---|---|
| width | 0.5–0.7 m |
| length | 0.5–0.7 m |
| (2) Spore | none |
| (3) Gram-staining | − |
| b. Physiological properties | |
| (1) Growth temperature range: | capable of growing at 37° C., appropriate growth temperature ranging from 15 to 28° C. |
| (2) Attitude to oxygen | aerobic |
| (3) Catalase | + |
| (4) Oxidase | − |
| (5) Urease | − |
| (6) Hydrolysis | |
| starch | + |
| gelatin | − |
| casein | − |
| esculin | + |
| (7) Reduction of nitrate | − |
| (8) Indole formation | − |
| (9) Hydrogen sulfide formation | + |
| (10) Solidification of milk | − |
| (11) Sodium requirement | + |
| (12) Salt requirement | |
| Growth in NaCl-free medium | − |
| Growth in 1% NaCl medium | − |
| Growth in seawater medium | + |
| (13) Quinone | menaquinone 7 |
| (14) GC content in intracellular DNA | 61% |
| (15) Diaminopimelic acid in cell wall | − |
| (16) Glycolyl test | − |
| (17) Presence of hydroxy fatty acid | + |
| (18) OF-test | O |
| (19) Colony color | forming no characteristic colony pigment |
| (20) Motility | yes |
| (21) Gliding | none |
| (22) Flagellum | polar monotrichate. |

According to the classification described in Bergey's Manual of Determinative Bacteriology, 9 (1994), this strain falls in the group 4 (Gram-negative aerobic bacilli and cocci). However, this strain largely differs from the bacteria belonging to the group 4 in having menaquinone 7 in the electron transport chain and containing 61% of GC. Fundamentally, gram-negative bacteria have ubiquinone in the electron transport chain while gram-positive bacteria have menaquinone.

Although gram-negative bacteria belonging to the genera Flavobacterium and Cytophaga exceptionally have menaquinone in the electron transport chain, they are largely different in GC content from the above-mentioned strain, such that *Cytophaga arvensicola* which is a soil bacterium contains from 43 to 46% of GC and *Cytophaga diffluens, C. fermentans, C. marina* and *C. uliginosa* which are marine bacteria each contains 42% of GC. When this strain is compared in the homology in 16SrDNA sequence with strains which have been identified, even the most homologous one (*Verrucomicrobium spinosum*) shows a homology of 76.6% therewith. It is widely known that two bacteria with a homology of 90% or less with each other are different in genus. Accordingly, the present inventors have decided that this strain is a novel bacterium belonging to none of the existing genera and named it *Fucoidanobacter marinus* SI-0098.

The above strain is indicated as *Fucoidanobacter marinus* SI-0098 and has been deposited at National Institute of Bioscience and Human-Technology, Agency of Industrial Science and Technology (1-3, Higashi 1-chome, Tsukuba-shi, Ibaraki-ken 305, JAPAN) under the accession number FERM P-14873 since Mar. 29, 1995 and deposited at National Institute of Bioscience and Human-Technology as described above under the accession number FERM BP-5403 (transfer to international deposition being requested on Feb. 15, 1996).

As described above, the present inventors have found out that the sulfated-fucose-containing polysaccharide-F and the sulfated-fucose-containing polysaccharide-U of the present invention show completely different behaviors from each other on an acidic polysaccharide agglutinating agent in the presence of one or more salts at a concentration of 0.6 to 3 M.

For example, the sulfated-fucose-containing polysaccharide-F of the present invention can be separated from an aqueous solution of a sulfated-fucose-containing polysaccharide mixtures by using the method of the present invention.

First, one or more salts are added to the aqueous solution of the sulfated-fucose-containing polysaccharide mixture in such a manner as to give a total salt concentration of 0.6 to 3 M. As the salts to be added, use can be made of, for example, sodium chloride and calcium chloride without restriction. After thus adjusting the salt concentration, an acidic polysaccharide coagulating agent such as cetylpyridinium chloride is added until no precipitate is formed any more. Then the precipitates are collected to thereby give the sulfated-fucose-containing polysaccharide-F of the present invention.

However, care must be taken in the point that the sulfated-fucose-containing polysaccharide-F of the present invention can hardly form any precipitate with cetylpyridinium chloride when the above-mentioned salt concentration exceeds 2 M. Usually, the sulfated-fucose-containing polysaccharide-F of the present invention can be separated from the sulfated-fucose-containing polysaccharide-U at a salt concentration of about 1.5 M (see, the illustration of FIG. 1).

After washing the precipitate if necessary, the cetylpyridinium chloride in the precipitate is washed away with a sodium chloride-saturated alcohol to thereby give the sulfated-fucose-containing polysaccharide-F of the present invention. The precipitate may be dissolved and subjected to ultrafiltration to thereby eliminate coloring matters from the sulfated-fucose-containing polysaccharide-F of the present invention thus obtained. It is also possible to desalt and freeze-dry the precipitate so as to give a dry preparation. Further, a preservative or the like may be added during the process.

The present inventors have also found out that when sulfated-fucose-containing polysaccharides are purified with the use of an anion exchange resin as described above, the coexistence of a divalent cation causes an increase in the amount of the sulfated-fucose-containing polysaccharides adsorbed onto the resin per unit area and thus the sulfated-fucose-containing polysaccharides can be separated more efficiently. To produce the sulfated-fucose-containing polysaccharide-F of the present invention by using the method of the present invention, therefore, a chemical serving as a divalent cation source is added preferably at a concentration of 1 mM or more to the sulfated-fucose-containing polysaccharide mixture. Next, the anion exchange resin is equilibrated with a solution containing the divalent cation preferably at a concentration of 1 mM or more and the above-mentioned sulfated-fucose-containing polysaccharide mixture is adsorbed thereby. After thoroughly washing the anion exchange resin with the solution employed in the equilibration, the sulfated-fucose-containing polysaccharide-F is developed by linear gradient elution with, for example, sodium chloride. In the practice of this method, the divalent cation may be added so as to give a concentration of 1 mM or more. As the chemical serving as the divalent cation source to be used in this method, calcium salts and barium salts exhibit particularly excellent effects. However, the present invention is not restricted thereto and use can be also made of magnesium sulfate, manganese chloride, etc. therefor.

The sulfated-fucose-containing polysaccharide-F of the present invention can be obtained by, for example, the method described in Example 8. Next, the physicochemical properties of this sulfated-fucose-containing polysaccharide-F will be illustrated, though the sulfated-fucose-containing polysaccharide-F of the present invention is not restricted thereto.

Figure 17:
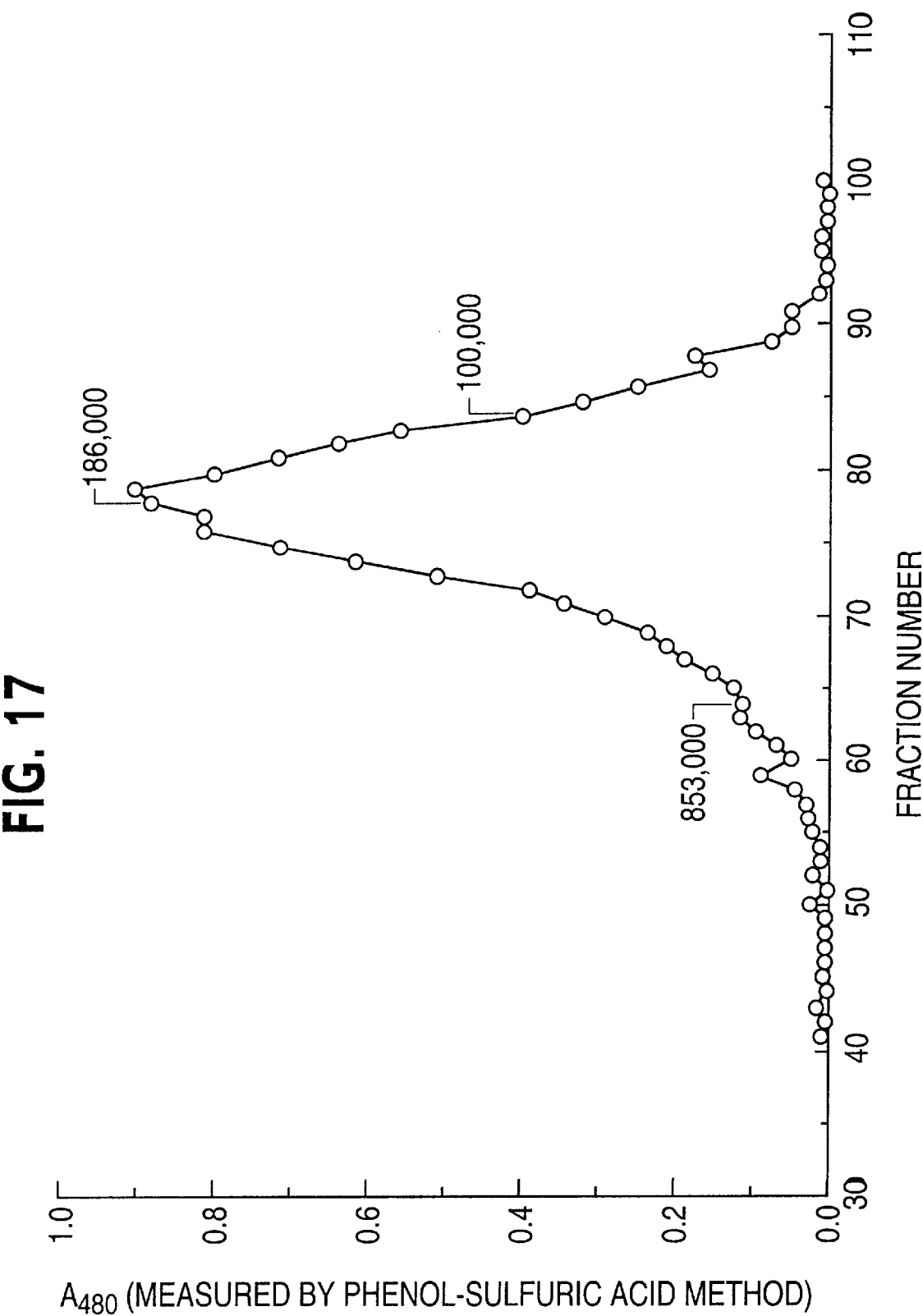
FIG. 17 shows the molecular weight distribution of the sulfated-fucose-containing polysaccharide-F determined by the gel filtration method with the use of Sephacryl S-500.

The molecular weight of the sulfated-fucose-containing polysaccharide-F thus obtained is determined by the gel filtration method with the use of Sephacryl S-500. As a result, it shows a molecular weight distribution around around 190,000 (FIG. 17). In FIG. 17, the ordinate refers to the saccharide content in the sample determined by the phenol-sulfuric acid method which is expressed in the absorbance at 480 nm while the abscissa refers to the fraction number.

The gel filtration is effected under the following conditions:

| | |
|---|---|
| column size: | 3.08 × 162.5 cm; |
| solvent: | 10 mM sodium phosphate buffer (pH 6.0) containing 0.2M of sodium chloride and 10% of ethanol; |
| flow rate: | 1.5 ml/min; |
| sample concentration: | 0.25%; |
| sample volume: | 20 ml; |
| molecular weight standard: | Shodex STANDARD P-82 (mfd. by Showa Denko, K.K.). |

Next, the components of the sulfated-fucose-containing polysaccharide-F of the present invention thus obtained are analyzed.

First, the fucose content is determined in accordance with the method described in Journal of Biological Chemistry, 175, 595 (1948).

Next, the dry preparation of the sulfated-fucose-containing polysaccharide-F thus obtained is dissolved in 1 N hydrochloric acid to give a concentration of 0.5% and treated at 110° C. for 2 hours to thereby hydrolyze it into constituting monosaccharides. Subsequently, the reducing ends of the monosaccharides obtained by the hydrolysis are pyridyl-(2)-aminated (PA) by using GlycoTAG and Glyco-TAG Reagent Kit and the composition ratio of the constituting monosaccharides is analyzed by HPLC. The HPLC is effected under the following conditions:

| | |
|---|---|
| apparatus | Model L-6200 (mfd. by Hitachi, Ltd.); |
| column | PALPAK Type A (4.6 mm × 150 mm); |
| eluent | 700 mM borate buffer |

-continued

| | |
|---|---|
| | (pH 9.0): |
| | acetonitrile = 9:1 |
| detection | Fluorometric Detector F-1150 |
| | (mfd. by Hitachi, Ltd.), |
| | excitation wavelength: |
| | 310 nm, fluorescent |
| | wavelength: 380 nm; |
| flow rate | 0.3 ml/min; |
| column temperature | 65° C. |

Next, the content of uronic acid is determined in accordance with the method described in Analytical Biochemistry, 4, 330 (1962)

Subsequently, the content of sulfuric acid is determined in accordance with the method described in Biochemical Journal, 84, 106 (1962).

As a result, it is found out that the constituting saccharides of the sulfated-fucose-containing polysaccharide-F obtained above are fucose and galactose at a molar ratio of about 10:1. Neither uronic acid nor any other neutral saccharide is substantially contained therein. The molar ratio of fucose to sulfate is about 1:2.

Next, 16 ml of a 1% solution of fucoidan-F, 12 ml of a 50 mM phosphate buffer (pH 8.0), 4 ml of 4 M sodium chloride and 8 ml of a 32 mU/ml solution of the above-mentioned endofucoidanase originating in Flavobacterium sp. SA-0082 (FERM BP-5402) are mixed together and reacted at 25° C. for 48 hours. As a result, no degradation product is formed and the substrate is not degraded.

Figure 18:
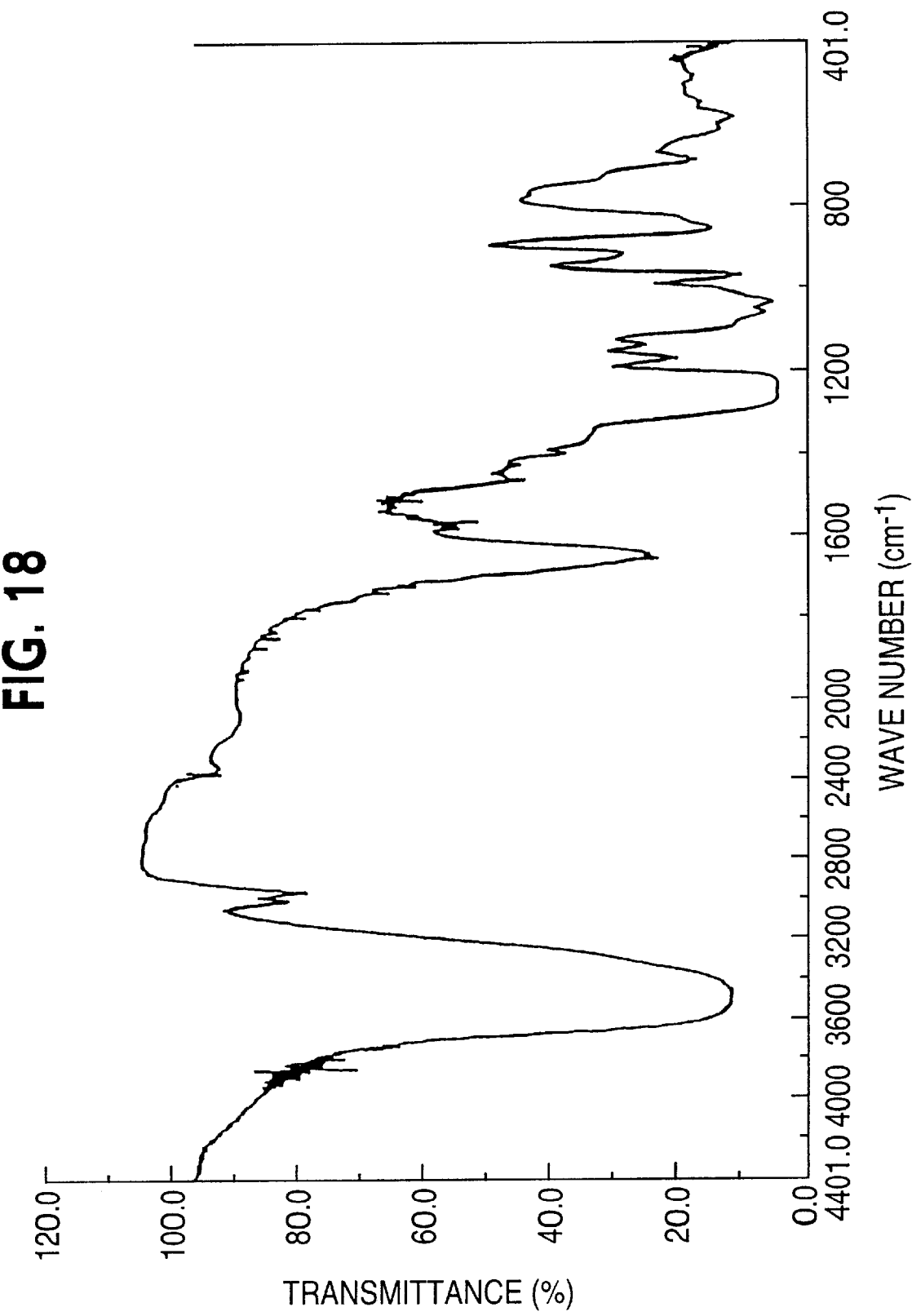
FIG. 18 is the IR spectrum of the sulfated-fucose-containing polysaccharide-F.

Then the IR spectrum of the sulfated-fucose-containing polysaccharide-F calcium salt is measured with a Fourier transform infrared spectrometer JIR-DIAMOND 20 (mfd. by JEOL Ltd.). Thus the spectrum as shown in FIG. 18 is obtained. In FIG. 18, the ordinate refers to the transmittance (%) while the abscissa refers to the wave number ($cm^{-1}$).

Next, the NMR spectrum of sodium salt of the sulfated-fucose-containing polysaccharide-F of the present invention is measured with a nuclear magnetic resonance spectrometer Model JNM-α500 (500 MHz; mfd. by JEOL Ltd.). Thus the spectrum as shown in FIG. 19 is obtained.

Figure 19:
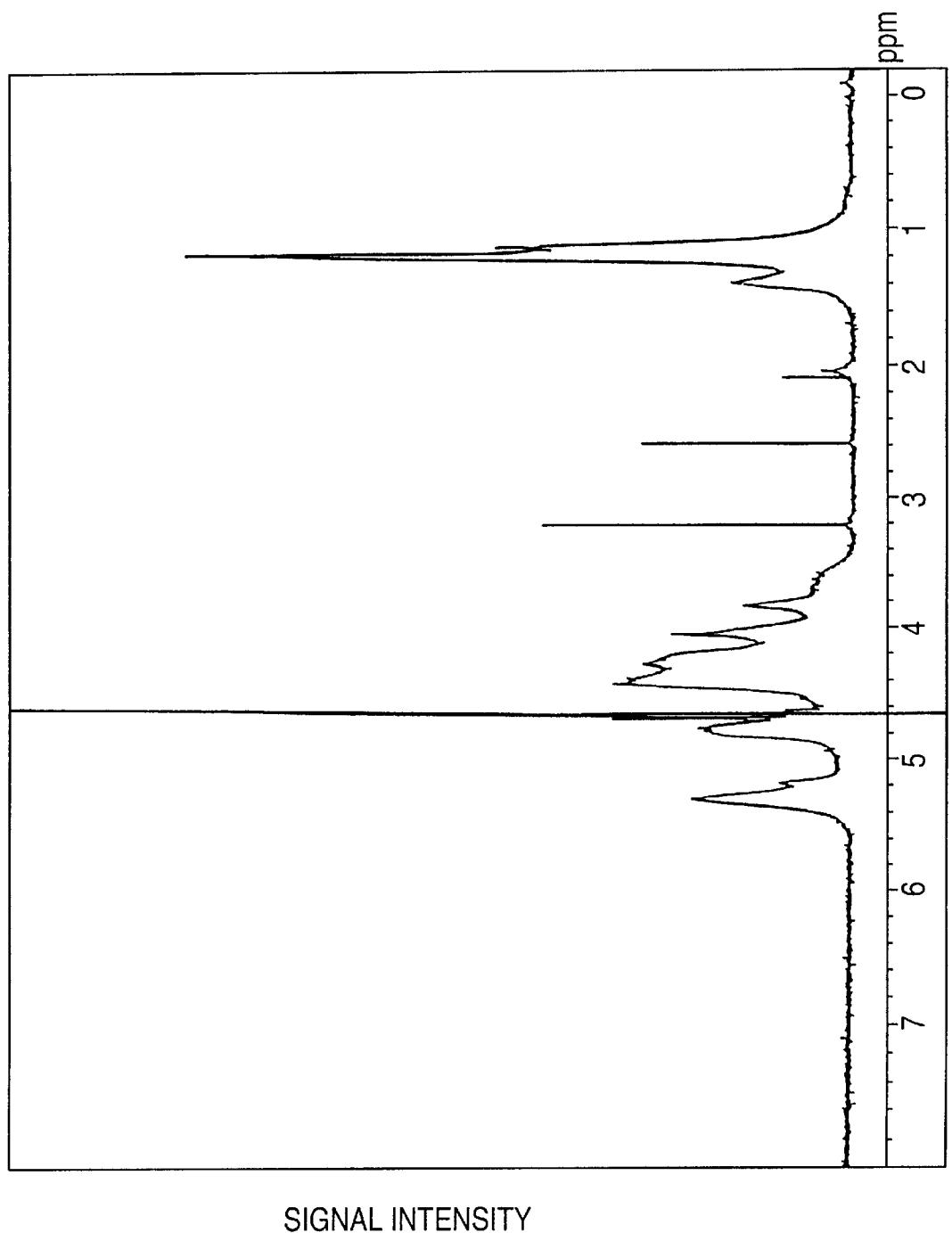
FIG. 19 is the $^1$H-NMR spectrum of the sulfated-fucose-containing polysaccharide-F.

In FIG. 19, the ordinate refers to the signal intensity while the abscissa refers to the chemical shift (ppm). The chemical shifts in $^1$H-NMR are expressed by taking the chemical shift of HOD as 4.65 ppm.

$^1$H-NMR ($D_2O$): 5.30 (H at the 1-position of fucose), 1.19 (H in $CH_3$ at the 5-position of fucose).

When measured with a high-speed, high-sensitivity polarimeter SEPA-300 (mfd. by Horiba Seisakusho), the freeze-dried product of the sulfated-fucose-containing polysaccharide-F has a specific rotation of –135°.

The present invention provides the sulfated-fucose-containing polysaccharide-F which has been separated from the sulfated-fucose-containing polysaccharide-U of the present invention and purified. The sulfated-fucose-containing polysaccharide-F of the present invention substantially contains no uronic acid as the constituting saccharide and is not degraded by the fucoidanase produced by Flavobacterium sp. SA-0082 (FERM BP-5402). The sulfated-fucose-containing polysaccharide-F of the present invention is not restricted in the molecular weight, molecular weight distribution or saccharide composition. Namely, sulfated-fucose-containing polysaccharide-F having arbitrary molecular weight and molecular weight distribution may be prepared and sulfated-fucose-containing polysaccharides having definitely clarified physicochemical properties such as the saccharide composition and reducing end and an extremely high degree of sulfation can be provided.

Because of having been separated from the sulfated-fucose-containing polysaccharide-U which substantially has no anticoagulant activity, the sulfated-fucose-containing polysaccharide-F of the present invention has a potent anticoagulant activity. Thus the sulfated-fucose-containing polysaccharide-F and/or degradation products thereof are usable in anticoagulant agents as purified sulfated-fucose-containing polysaccharides and also useful as an antigen against an anti-sulfated-fucose-containing polysaccharide antibody.

When the sulfated-fucose-containing polysaccharides or degradation products thereof according to the present invention are added at a concentration of 1 μg/ml or more to a culture medium of cancer cells, the cancer cells undergo apoptosis one to several days after the addition. That is to say, the sulfated-fucose-containing polysaccharides and degradation products thereof have a potent effect of inducing apoptosis. On normal cells, these substances exert neither any effect of inducing apoptosis nor toxicity. In particular, sulfated-fucose-containing polysaccharides originating in edible brown algae and sea cucumber and degradation products thereof are highly safe.

To prepare the apoptosis inducer of the present invention, the sulfated-fucose-containing polysaccharides and/or degradation products thereof are employed as the active ingredient and combined with publicly known pharmaceutical carriers. In general, the sulfated-fucose-containing polysaccharides and/or degradation products thereof are blended with pharmaceutically acceptable liquid or solid carriers. After optionally adding solvents, dispersing agents, emulsifiers, buffers, stabilizers, fillers, binders, disintegrators, lubricants and the like thereto, the blend is processed into solid preparations such as tablets, granules, powders, dusts, capsules or the like or liquid preparations such as solutions, suspensions, emulsion or the like. Alternatively, it may be processed into a dry preparation which can be liquefied by adding an appropriate carrier thereto before using.

The apoptosis inducer of the present invention can be administered either orally or parenterally by, for example, injection or intravenous drip infusion.

The pharmaceutical carriers may be appropriately selected depending on the administration route and dosage form as described above. In the case of oral drugs, use can be made of, for example, starch, lactose, sucrose, mannitol, carboxymethylcellulose, corn starch and inorganic salts. To prepare oral drugs, it is also possible to add binders, disintegrators, surfactants, lubricants, fluidity improvers, corrigents, coloring agents, perfumes and the like. Particular examples of these additives are as follows.

Binder: starch, dextrin, powdered acacia, gelatin, hydroxypropylstarch, methylcellulose, carboxymethylcellulose sodium, hydroxypropylcellulose, crystalline cellulose, ethylcellulose, poly(vinylpyrrolidone) and macrogol.

Disintegrator: starch, hydroxypropylstarch, carboxymethylcellulose sodium, carboxymethylcellulose calcium, carboxymehtylcellulose and low-substitution hydroxypropylcellulose.

Surfactant: sodium lauryl sulfate, soybean lecithin, sucrose fatty acid esters and polysorbate 80.

Lubricant: talc, waxes, hydrogenated vegetable oils, sucrose fatty acid esters, magnesium stearate, calcium stearate, aluminum stearate and polyethylene glycol.

Fluidity improvers: light anhydrous silicic acid, dry aluminum hydroxide gel, synthetic aluminum silicate and magnesium silicate.

Examples of liquid preparations for oral administration include suspensions, emulsions, syrups and elixirs each optionally containing corrigents and coloring agents.

On the other hand, parenteral preparations may be obtained by dissolving or suspending the sulfated-fucose-containing polysaccharides and/or degradation products thereof, which are the active ingredient of the present invention, in diluents such as distilled water for injection, physiological saline solution, an aqueous solution of glucose, vegetable oils for injection, sesame oil, peanut oil, soybean oil, corn oil, propylene glycol, polyethylene glycol or the like in a conventional manner and adding, if necessary, bactericides, stabilizers, tonicity agents, soothing agents, etc. thereto.

The apoptosis inducer of the present invention is administered via an appropriate administration route suitable for the dosage form. The administration method is not particularly restricted too. Namely, internal use, external use or injection may be selected therefor. Injections may be administered, for example, intravenously, intramuscularly, subcutaneously or intradermally. Preparations for external use include suppositories.

The dose of the apoptosis inducer of the present invention is not particularly specified but may be appropriately determined depending on the dosage form, administration method, purpose of the use, and the age, body weight, conditions, etc. of the patient. In general, the dose may be determined so that from 1 to 1,000 mg/day, preferably form 10 to 200 mg/day, of the active ingredient is given to an adult. As a matter of course, the dose varies depending on various factors. Thus, it is sufficient to employ a dose lower than the above-mentioned level in some cases and a dose exceeding the above level is needed in other cases.

An anticancer drug can be produced by using the sulfated-fucose-containing polysaccharide-U, the sulfated-fucose-containing polysaccharide-F and/or the degradation products thereof according to the present invention, which have anticancer effects, as the active ingredient, combining the same with publicly known pharmaceutical carriers and then processing the blend into a drug preparation. The anticancer drug may be produced in accordance with the method described above. In general, the sulfated-fucose-containing polysaccharides and/or degradation products thereof of the present invention are blended with pharmaceutically acceptable liquid or solid carriers. After optionally adding solvents, dispersing agents, emulsifiers, buffers, stabilizers, fillers, binders, disintegrators, lubricants and the like thereto, the blend is processed into solid preparations such as tablets, granules, powders, dusts, capsules or the like or liquid preparations such as solutions, suspensions, emulsion or the like. Alternatively, it may be processed into a dry preparation which can be liquefied by adding an appropriate carrier thereto before using.

The anticancer drug of the present invention can be administered either orally or parenterally by, for example, injection or intravenous drip infusion.

The pharmaceutical carriers may be appropriately selected depending on the administration route and dosage form in accordance with the case of the above-mentioned apoptosis inducer.

The anticancer drug is administered via an appropriate administration route suitable for the dosage form. The administration method is not particularly restricted too. Namely, internal use, external use or injection may be selected therefor. Injections may be administered, for example, intravenously, intramuscularly, subcutaneously or intradermally. Preparations for external use include suppositories.

The dose of the anticancer drug of the present invention is not particularly specified but may be appropriately determined depending on the dosage form, administration method, purpose of the use, and the age, body weight, conditions, etc. of the patient. In general, the dose may be determined so that from 1 to 1,000 mg/day, preferably form 10 to 200 mg/day, of the active ingredient is given to an adult. As a matter of course, the dose varies depending on various factors. Thus, it is sufficient to employ a dose lower than the above-mentioned level in some cases and a dose exceeding the above level is needed in other cases. The drug of the present invention may be orally administered as such. Alternatively, it may be added to arbitrary foods or drinks for daily intake.

A carcinostatic drug can be produced by using the sulfated-fucose-containing polysaccharides and/or the degradation products thereof according to the present invention, which have carcinostatic effects, as the active ingredient, combining the same with publicly known pharmaceutical carriers and then processing the blend into a drug preparation. The carcinostatic drug may be produced in accordance with the method described above. In general, the sulfated-fucose-containing polysaccharides and/or degradation products thereof of the present invention are blended with pharmaceutically acceptable liquid or solid carriers. After optionally adding solvents, dispersing agents, emulsifiers, buffers, stabilizers, fillers, binders, disintegrators, lubricants and the like thereto, the blend is processed into solid preparations such as tablets, granules, powders, dusts, capsules or the like or liquid preparations such as solutions, suspensions, emulsion or the like. Alternatively, it may be processed into a dry preparation which can be liquefied by adding an appropriate carrier thereto before using.

The carcinostatic drug can be administered either orally or parenterally by, for example, injection or intravenous drip infusion.

The pharmaceutical carriers may be appropriately selected depending on the administration route and dosage form in accordance with the case of the above-mentioned apoptosis inducer.

The carcinostatic drug is administered via an appropriate administration route suitable for the dosage form. The administration method is not particularly restricted too. Namely, internal use, external use or injection may be selected therefor. Injections may be administered, for example, intravenously, intramuscularly, subcutaneously or intradermally. Preparations for external use include suppositories.

The dose of the carcinostatic drug is not particularly specified but may be appropriately determined depending on the dosage form, administration method, purpose of the use and the age, body weight, conditions, etc. of the patient. In general, the dose may be determined so that from 1 to 1,000 mg/day, preferably form 10 to 200 mg/day, of the active ingredient is given to an adult. As a matter of course, the dose varies depending on various factors. Thus, it is sufficient to employ a dose lower than the above-mentioned level in some cases and a dose exceeding the above level is needed in other cases. The drug of the present invention may be orally administered as such. Alternatively, it may be added to arbitrary foods or drinks for daily intake.

The sulfated-fucose-containing polysaccharides and degradation products thereof according to the present invention are substances with natural origins and show no toxicity when orally administered to mice.

The drugs of the present invention are expected to be usable as remedies for infectious diseases, immune depression, hyperimmunity, cancer, viral diseases and the like. Also, they are usable as preventives for cancer to maintain healthy conditions. The method for inducing apoptosis of the present invention is useful in, for example, studying biological defence mechanisms, immune functions and the relations to cancer and viral diseases or developing apoptosis inducers. In particular, the sulfated-fucose-containing polysaccharides and degradation products thereof according to the present invention prepared from edible brown algae or sea cucumber, which have been taken as foods for a long time, are highly safe in oral administration.

Because of being sulfated polysaccharides with very high molecular weights, the sulfated-fucose-containing polysaccharides are not usable as such as drugs but to be degraded to a certain extent so as to improve the antigenicity, homogeneity, anticoagulant activity, etc. thereof. The present invention provides an enzyme capable of selectively degrading the sulfated-fucose-containing polysaccharide-F alone and degradation products of the sulfated-fucose-containing polysaccharide-F obtained by treating the sulfated-fucose-containing polysaccharide-F with the enzyme.

The strain to be used in the present invention may be any Alteromonas, so long as it can produce the endo-sulfated-fucose-containing polysaccharide degrading enzyme. As a particular example of the strain capable of producing the endo-sulfated-fucose-containing polysaccharide degrading enzyme, citation can be made of Alteromonas sp. SA-1009. The degradation products of the sulfated-fucose-containing polysaccharide-F of the present invention can be obtained by treating the sulfated-fucose-containing polysaccharide-F with the endo-sulfated-fucose-containing polysaccharide degrading enzyme originating in this strain.

This strain, which was newly isolated by the present inventors from seawater in Aomori, has the following mycological properties.

| a. Morphological properties | |
|---|---|
| (1) Rod; | |
| width | about 1 μm |
| length | about 2 μm |
| (2) Spore | none |
| (3) Gram-staining | − |
| b. Physiological properties | |
| (1) Growth temperature range: | appropriate growth temperature ranging from 15 to 30° C., being unable to grow at 4° C. or 40° C. |
| (2) Attitude to oxygen | aerobic |
| (3) Catalase | + |
| (4) Oxidase | + |
| (5) Lipase | + |
| (6) Metabolism | |
| glucose | + |
| mannose | − |
| sucrose | + |
| lactose | − |
| cellobiose | + |
| melibiose | − |
| mannitol | + |
| glycerol | + |
| methanol | − |
| DL-malic acid | − |
| succinic acid | − |
| fumaric acid | − |
| citric acid | − |
| salicin | − |

| -continued | |
|---|---|
| (7) Hydrolysis | |
| starch | − |
| gelatin | − |
| (8) Reduction of nitrate | − |
| (9) Denitrification | − |
| (10) Decomposition of alginic acid | + |
| (11) Utilization of β-hydroxybutyric acid | − |
| (12) Accumulation of polyhydroxybutyric acid | − |
| (13) Sodium requirement | + |
| (14) Salt requirement | |
| Growth in NaCl-free medium | − |
| Growth in 1% NaCl medium | − |
| Growth in seawater medium | + |
| (15) Quinone | ubiquinone 8 |
| (16) GC content in intracellular DNA | 36% |
| (17) OF-test | O |
| (18) Colony color | forming no characteristic pigment |
| (19) Luminosity | − |
| (20) Motility | + |
| (21) Flagellum | polar monotrichate. |

According to the classification described in Bergey's Manual of Systematic Bacteriology, 1, 343–352 (1984) and Bergey's Manual of Determinative Bacteriology, 9 75, 132–133 (1994), this strain is identified as a bacterium belonging to the genus Alteromonas. However, the physiological properties of this strain agree with none of the bacteria described therein. Also it shows a low GC content. Thus, it is named Alteromonas sp. SN-1009.

The above strain is indicated as Alteromonas sp. SN-1009 and has been deposited at National Institute of Bioscience and Human-Technology, Agency of Industrial Science and Technology (1-3, Higashi 1-chome, Tsukuba-shi, Ibaraki-ken 305, JAPAN) under the accession number FERM P-15436 since Feb. 13, 1996 and deposited at National Institute of Bioscience and Human-Technology as described above under the accession number FERM BP-5747 (transfer to international deposition being requested on Nov. 15, 1996).

The nutrients to be added to the medium for incubating the strain employed in the present invention may be arbitrary ones so long as the strain can utilize them so as to produce the endo-sulfated-fucose-containing polysaccharide degrading enzyme of the present invention. Appropriate examples of the carbon source include sulfated-fucose-containing polysaccharides, marine alga powder, alginic acid, fucose, galactose, glucose, mannitol, glycerol, saccharose and maltose, while appropriate examples of the nitrogen source include yeast extract, peptone, casamino acids, corn steep liquor, meat extract, defatted soybean, ammonium sulfate and ammonium chloride. The medium may further contain inorganic m matters and metal salts such as sodium salts, phosphates, potassium salts, magnesium salts and zinc salts.

Also, this strain grows very well in seawater or artificial seawater containing the above nutrients.

In the incubation of the strain producing the endo-sulfated-fucose-containing polysaccharide degrading enzyme of the present invention, the yield varies depending on the incubation conditions. Generally speaking, the maximum yield of the endo-sulfated-fucose-containing polysaccharide degrading enzyme can be achieved by incubating the strain at a temperature of from 15 to 30° C. and at a pH value of the medium of 6 to 9 under aeration/agitation for 5 to 72 hours.

Needless to say, the incubation conditions should be selected depending on the strain employed, the medium composition, etc. so that the yield of the endo-sulfated-fucose-containing polysaccharide degrading enzyme of the present invention can attain the maximum level.

The endo-sulfated-fucose-containing polysaccharide degrading enzyme of the present invention is contained in both of the cells and the culture supernatant.

The above-mentioned Alteromonas sp. SN-1009 is incubated in an appropriate medium and the cells are harvested and disrupted by a means commonly employed for disrupting cells such as ultrasonication. Thus a cell-free extract can be obtained.

Subsequently, the extract is purified by a purification procedure commonly employed in the art to thereby give a purified enzyme preparation. For example, the purification may be effected by salting out, ion exchange chromatography, hydrophobic bond column chromatography, gel filtration or the like to thereby give the purified endo-sulfated-fucose-containing polysaccharide degrading enzyme of the present invention free from any other fucoidanase.

The culture supernatant obtained by eliminating the cells from the above-mentioned culture medium also contains a large amount of this enzyme which can be purified by the same means as those employed for purifying the intracellular enzyme.

The chemical and physicochemical properties of the endo-sulfated-fucose-containing polysaccharide degrading enzyme of the present invention are as follows:

(i) function: acting on sulfated-fucose-containing polysaccharides having the following physicochemical properties, i.e., the sulfated-fucose-containing polysaccharide-F and degrading the sulfated-fucose-containing polysaccharide-F:

(a) constituting saccharide: substantially being free from uronic acid; and (b) substantially incapable of being degraded by the fucoidanase produced by Flavobacterium sp. SA-0082 (FERM BP-5402);
    but not acting on sulfated-fucose-containing polysaccharides having the following physicochemical properties, i.e., the sulfated-fucose-containing polysaccharide-U:

(c) constituting saccharide: containing uronic acid; and (d) being degraded by the fucoidanase produced by Flavobacterium sp. SA-0082 (FERM BP-5402) to thereby form at least one of the compounds selected from those represented by the following formulae (I), (II) and (III):

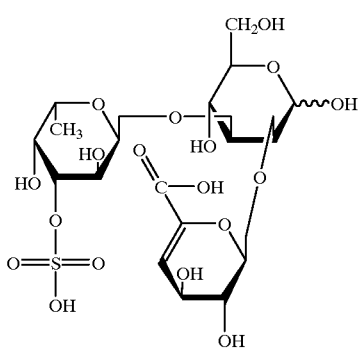
(I)

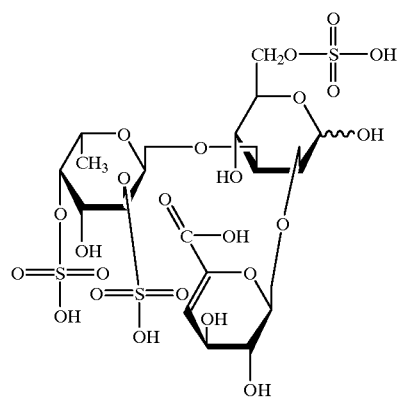
(II)

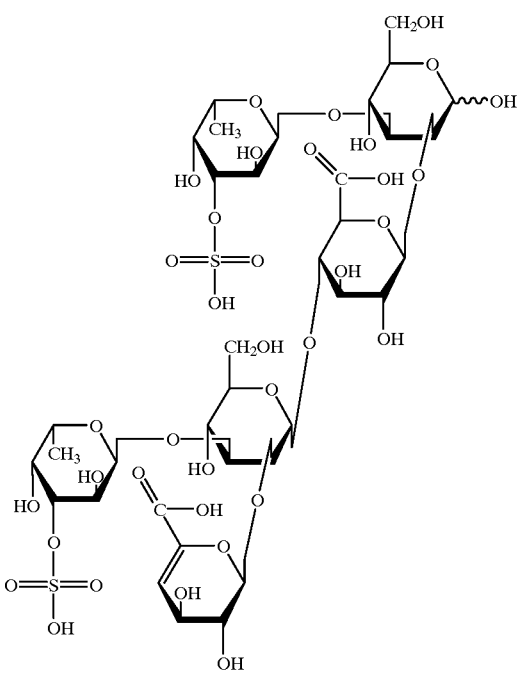
(III)

Figure 20:
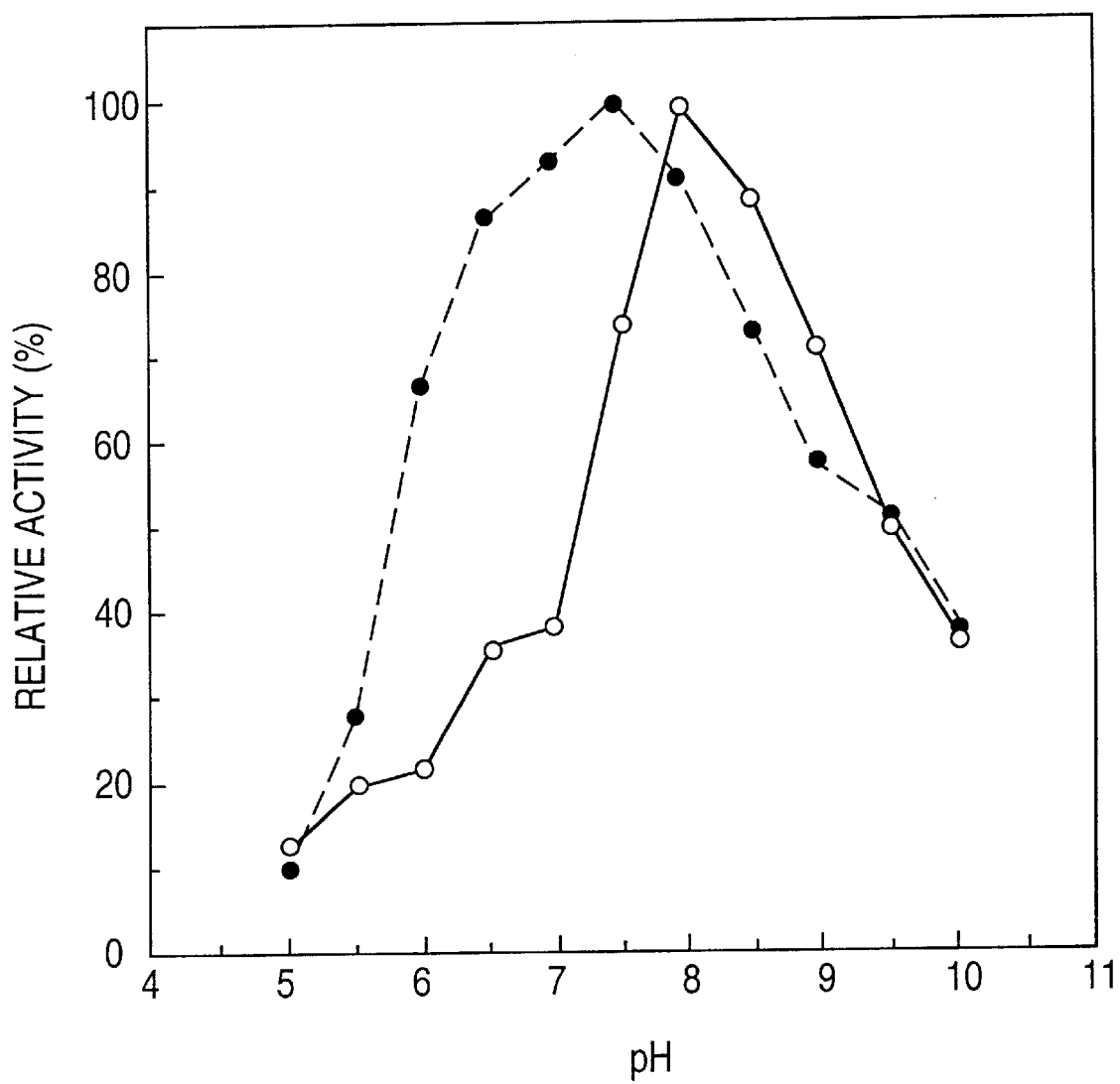
FIG. 20 is a graph which shows the relationship between the relative activity of the endo-sulfated-fucose-containing polysaccharide degrading enzyme obtained by the present invention and the pH value.

(ii) optimum pH value: being from about pH 7 to 8 (FIG. 20).

FIG. 20 is a graph which shows the relationship between the relative activity of this enzyme and the pH value wherein the ordinate refers to the relative activity (%) while the abscissa refers to the pH value. The solid line is obtained by using the sulfated-fucose-containing polysaccharide-F with PA-reducing end (PA-FF) as the substrate while the dotted line is obtained by using the sulfated-fucose-containing polysaccharide-F as will be described in (V)-(2) hereinafter as the substrate.

(iii) optimum temperature: being about 30 to 35° C. (FIG. 21).

Figure 21:
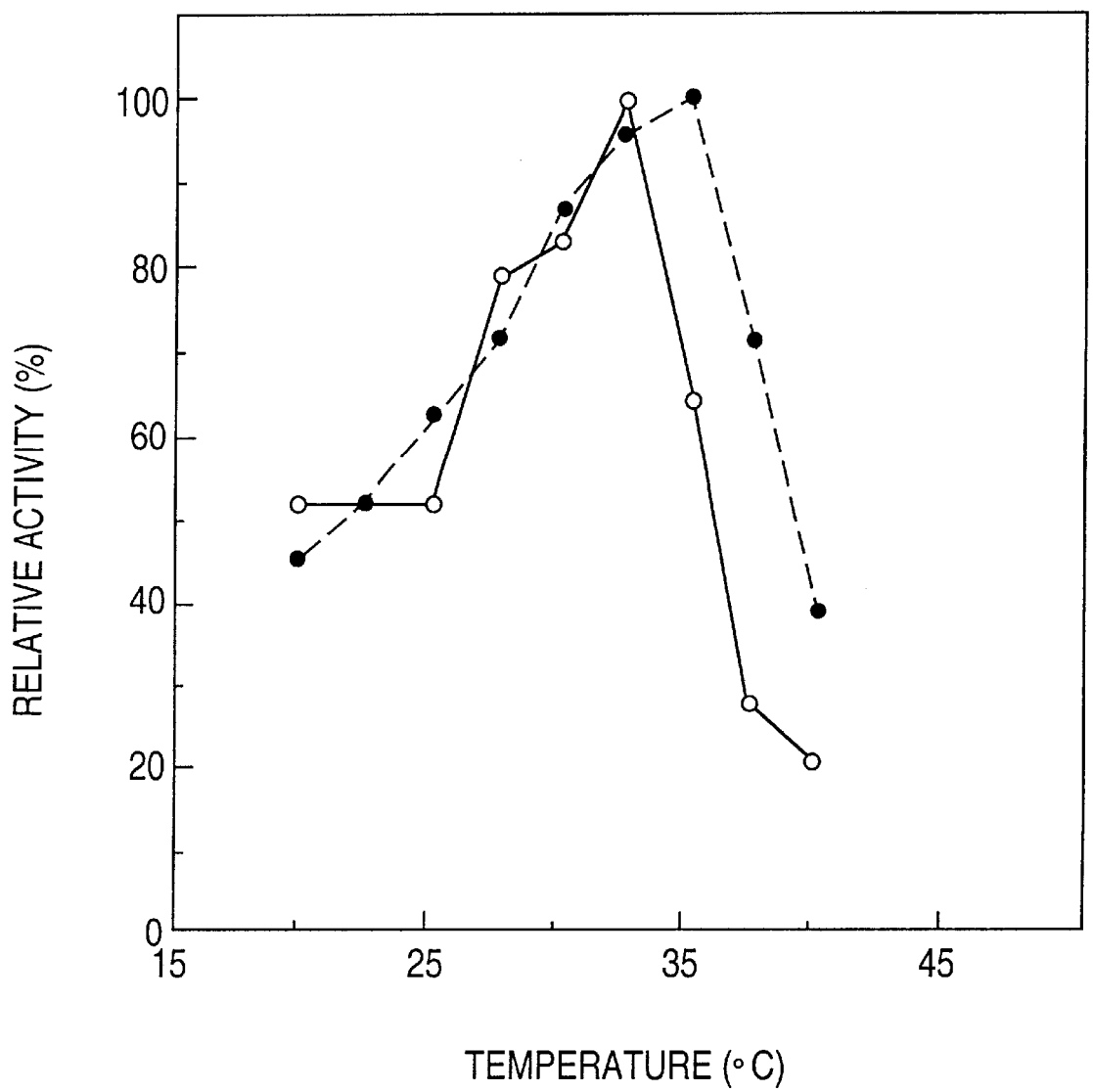
FIG. 21 is a graph which shows the relationship between the relative activity of the endo-sulfated-fucose-containing polysaccharide degrading enzyme obtained by the present invention and the temperature.

FIG. 21 is a graph which shows the relationship between the relative activity of this enzyme and the temperature wherein the ordinate refers to the relative activity (%) while the abscissa refers to the temperature (° C.). The solid line is obtained by using the sulfated-fucose-containing polysaccharide-F with PA-reducing end (PA-FF) as the substrate while the dotted line is obtained by using the sulfated-fucose-containing polysaccharide-F as will be described in (V)-(2) hereinafter as the substrate.

(iv) molecular weight: the molecular weight of this enzyme determined by gel filtration with the use of Sephacryl S-200 (mfd. by Pharmacia) is about 100,000;

(v) method for measuring enzymatic activity:

The activity of the endo-sulfated-fucose-containing polysaccharide degrading enzyme of the present invention is measured in the following manner.

First, the sulfated-fucose-containing polysaccharide-F and PA-FF serving as the substrate of the endo-sulfated-fucose-containing polysaccharide degrading enzyme of the present invention are prepared in the following steps (1) to (3).

(1) Preparation of *Kjellmaniella crassifolia* Sulfated-Fucose-Containing Polysaccharide Mixture:

2 kg of dry *Kjellmaniella crassifolia* is ground with a free mill Model M-2 (mfd. by Nara Kikai Seisakusho) and treated in 4.5 times as much 80% ethanol at 80° C. for 2 hours. Then it is filtered and the residue is further subjected to the above procedures, i.e., the extraction with 80% ethanol and filtration thrice to thereby give 1,870 g of the residue after ethanol-washing. To this residue is added 36 l of water and the mixture is treated at 100° C. for 2 hours and then filtered to thereby give an extract. The salt concentration of the extract is adjusted to the same level as that of a 400 mM solution of sodium chloride. Then 5% of cetylpyridinium chloride is added thereto until no precipitate is formed any more. After centrifuging, the precipitate is repeatedly washed with 80% ethanol to thereby completely eliminate the cetylpyridinium chloride therefrom. Next, it is dissolved in 3 l of a 2 M solution of sodium chloride. After removing the insoluble matters by centrifugation, 100 ml of DEAE-Cellulofine A-800 equilibrated with 2 M sodium chloride is suspended therein. The suspension is stirred and then filtered to thereby remove the resin. The filtrate is fed into a 100 ml DEAE-Cellulofine A-800 column equilibrated with 2 M sodium chloride and the fraction passing therethrough is desalted and low-molecular weight matters are removed therefrom by using an ultrafiltration membrane (exclusion molecular weight of membrane: 100,000). The precipitate thus formed is eliminated by centrifugation. The supernatant is freeze-dried to thereby give 82.2 g of a purified *Kjellmaniella crassifolia* sulfated-fucose-containing polysaccharide mixture.

(2) Preparation of Sulfated-Fucose-Containing Polysaccharide-F:

6 g of the above-mentioned sulfated-fucose-containing polysaccharide mixture originating in *Kjellmaniella crassifolia* is dissolved in 600 ml of 20 mM of sodium acetate (pH 6.0) containing 0.2 M of calcium chloride. Then the solution is fed into a 3600 ml DEAE-Sepharose FF column preliminarily equilibrated with 20 mM of sodium acetate (pH 6.0) containing 0.2 M of calcium chloride. Then the column is thoroughly washed with 20 mM of sodium acetate (pH 6.0) containing 0.2 M of calcium chloride and developed by linear gradient elution with sodium chloride of 0 to 2 M.

The sulfated-fucose-containing polysaccharide-F fractions eluted at sodium chloride concentrations of 0.75 M and above are collected and desalted by using an ultrafilter provided with an ultrafiltration membrane of exclusion molecular weight of 100,000. After freeze-drying, 3.3 g of a freeze-dried preparation of the sulfated-fucose-containing polysaccharide-F is obtained.

(3) Preparation of PA-FF:

12 mg of the above-mentioned freeze-dried preparation of the sulfated-fucose-containing polysaccharide-F is dissolved in 480 μl of water and 12 μl portions of the obtained solution are pipetted into 36 tubes. After freeze-drying, the reducing end is pyridyl-(2)-aminated (PA) by using GlycoTAG and GlycoTAG Reagent Kit to thereby give PA-FF. The PA-FF thus obtained is dissolved in a 10 mM solution of ammonium acetate containing 15 ml of 10% methanol and subjected to gel filtration with the use of a Cellulofine GCL-300 column (40×900 mm). The high-molecular weight fractions are collected and desalted by thoroughly dialyzing with the use of a dialysis membrane of 3500 in pore size. Subsequently, it is concentrated to 5 ml with an evaporator to thereby give PA-FF to be used as the substrate of the endo-sulfated-fucose-containing polysaccharide-F degrading enzyme of the present invention.

The quantity of PA-FF thus obtained is estimated as about 40 nmol through the comparison with the fluorescence intensity of marketed pyridyl-(2)-aminated fucose (mfd. by Takara Shuzo Co., Ltd.; excitation wavelength: 320 nm, fluorescent wavelength: 400 nm).

By using the sulfated-fucose-containing polysaccharide-F obtained by the above steps (1) and (2), the activity of the endo-sulfated-fucose-containing polysaccharide degrading enzyme of the present invention is determined in the following manner.

Namely, 12 μl of a 2.5% solution of the sulfated-fucose-containing polysaccharide-F, 6 μl of a 1 M solution of calcium chloride, 12 μl of a 1 M solution of sodium chloride, 72 μl of a buffer (pH 7.5) containing 50 mM of acetic acid, imidazole and Tris hydrochloride and 18 μl of the endo-sulfated-fucose-containing polysaccharide-F degrading enzyme of the present invention are mixed together and reacted at 30° C. for 3 hours. Then the reaction mixture is treated at 100° C. for 10 minutes and centrifuged. Then the degree of degradation is measured by analyzing a 100 μl portion of the reaction mixture by HPLC.

As controls, use is made of a reaction mixture prepared by the same method but substituting the endo-sulfated-fucose-containing polysaccharide degrading enzyme of the present invention by the buffer employed for dissolving the endo-sulfated-fucose-containing polysaccharide degrading enzyme of the present invention therein and another reaction mixture prepared by the same method but substituting the sulfated-fucose-containing polysaccharide-F solution by water alone. These controls are also analyzed by HPLC.

The amount of the enzyme by which the fucosyl bonds in 1 μmol of the sulfated-fucose-containing polysaccharide-F can be cleaved in one minute is taken as one U. The fucosyl bonds thus cleaved are calculated in accordance with the following equation:

| | |
|---|---|
| Activity (U/ml) = $\{(12 \times 2.5)/(100 \times \text{MF})\} \times \{(\text{MF/M}) - 1\} \times \{0.12/(180 \times 0.01)\}$ $(12 \times 2.5)/100$ | sulfated-fucose-containing polysaccharide-F (mg) added to reaction system; |
| MF | average molecular weight of substrate (sulfated-fucose-containing polysaccharide-F); |
| M | average molecular weight of reaction product; |
| (MF/M) − 1 | number of cleavages by enzyme in one molecule of sulfated-fucose-containing polysaccharide-F; |
| 180 | reaction time (min); |
| 0.01 | volume (ml) of enzyme solution; and |
| 0.12 | volume (ml) of whole reaction mixture. |

The HPLC is effected under the following conditions:

| apparatus | Model L-6200 (mfd. by Hitachi, Ltd.); |
|---|---|
| column | OHpack KB-804 (8 mm × 300 mm, mfd. by Showa Denko K. K.); |
| eluent | 25 mM imidazole buffer (pH 8) containing 5 mM of sodium azide, 25 mM of calcium chloride and 50 mM of sodium chloride; |
| detection | differential refractometric detector (Shodex RI-71, mfd. by Showa Denko K. K.); |
| flow rate | 1 ml/min; |
| column temperature | 25° C. |

To measure the average molecular weight of the reaction product, marketed pullulan with a known molecular weight (STANDARD P-82, mfd. by Showa Denko K.K.) is analyzed by HPLC under the same conditions as those described above. Then a curve showing the relationship between the molecular weight of the pullulan and the retention time on the OHpak KB-804 is prepared and employed as the standard curve for determining the molecular weight of the above-mentioned enzymatic reaction product.

By using the PA-FF obtained by the above steps (1) to (3), the activity of the endo-sulfated-fucose-containing polysaccharide degrading enzyme of the present invention is determined in the following manner.

Namely, 2 μl of an 8 pmol/μl solution of the PA-FF, 5 μl of a 1 M solution of calcium chloride, 10 μl of a 1 M solution of sodium chloride, 23 μl of water, 50 μl of a buffer (pH 8.2) containing 50 mM of acetic acid, imidazole and Tris hydrochloride and 10 μl of the endo-sulfated-fucose-containing polysaccharide degrading enzyme of the present invention are mixed together and reacted at 30° C. for 3 hours. Then the reaction mixture is treated at 100° C. for 10 minutes and centrifuged. Then the degree of degradation is measured by HPLC using 80 μl of the sample thus prepared.

As controls, use is made of a reaction mixture prepared by the same method but substituting the endo-sulfated-fucose-containing polysaccharide degrading enzyme of the present invention by the buffer employed for dissolving the endo-sulfated-fucose-containing polysaccharide degrading enzyme of the present invention therein and another reaction mixture prepared by the same method but substituting the PA-FF solution by water alone. These controls are also analyzed by HPLC.

The amount of the enzyme by which the fucosyl bonds in 1 μmol of the sulfated-fucose-containing polysaccharide can be cleaved in one minute is taken as one U. The fucosyl bonds thus cleaved are calculated in accordance with the following equation:

| $16 \times 10^{-6}$: | amount (μmol) of PA-FF added to reaction system; |
|---|---|
| MF: | average molecular weight of substrate (sulfated-fucose-containing polysaccharide-F); |
| M: | average molecular weight of reaction product; |
| (MF/M) − 1: | number of cleavages by enzyme in one molecule of sulfated-fucose-containing polysaccharide-F; |
| 180: | reaction time (min); and |
| 0.01: | volume (ml) of enzyme solution. |

Activity (U/ml) = $16 \times 10^{-6} \times \{(MF/M) - 1\} \times \{1/(180 \times 0.01)\}$ The HPLC is effected under the following conditions:

| apparatus: | Model L-6200 (mfd. by Hitachi, Ltd.); |
|---|---|
| column: | OHpak SN-803 (8 mm × 300 mm, mfd. by Showa Denko K.K.); |
| eluent: | 200 mM sodium chloride solution containing 5 mM of sodium azide and 10% of dimethyl sulfoxide; |
| detection: | Fluorometric Detector F-1150 (mfd. by Hitachi, Ltd.), excitation wavelength: 320 nm, fluorescent wavelength: 400 nm; |
| flow rate: | 1 ml/min; and |
| column temperature: | 50° C. |

To measure the average molecular weight of the reaction product, the reducing end of marketed pullulan with a known molecular weight (STANDARD P-82, mfd. by Showa Denko K.K.) is pyridyl-(2)-aminated (PA) by using GlycoTAG and GlycoTAG Reagent Kit to thereby give PA-pullulans of various molecular weights. These PA-pullulans with various molecular weights are then analyzed by HPLC under the same conditions as those described above. Then a curve showing the relationship between the molecular weight of the pllulan and the retention time on the OHpak SB-803 is prepared and employed as the standard curve for determining the molecular weight of the above-mentioned enzymatic reaction product.

The protein is determined by measuring the absorbance of the enzyme solution at 280 nm. Calculation is made by taking the absorbance of a 1 mg/ml protein solution as 1.0.

The present inventors have clarified the action mechanism of the endo-sulfated-fucose-containing polysaccharide degrading enzyme of the present invention in the following manner.

(1) Degradation of Sulfated-Fucose-Containing Polysaccharide-F by Endo-Sulfated-Fucose-Containing Polysaccharide Degrading Enzyme and Preparation of Degradation Product:

Purified sulfated-fucose-containing polysaccharide-F originating in *Kjellmaniella crassifolia* is treated with the endo-sulfated-fucose-containing polysaccharide degrading enzyme of the present invention to thereby prepare the degradation products thereof.

First, the sulfated-fucose-containing polysaccharide degrading enzyme is produced. Namely, Alteromonas sp. SN-1009 (FERM BP-5747) is inoculated into 600 ml of a medium comprising an artificial seawater (pH 8.2, mfd. by Jamarin Laboratory) containing 0.25% of glucose, 1.0% of peptone and 0.05% of yeast extract which has been pipetted into a 2-l Erlenmeyer flask and sterilized at 120° C. for 20 minutes. Then the strain is incubated therein at 25° C. for 26 hours to thereby give a seed culture. Into a 30-l jar fermenter is fed 20 l of a medium comprising an artificial seawater (pH 8.0) containing 1.0% of peptone, 0.02% of yeast extract, 0.2% of the above-mentioned sulfated-fucose-containing polysaccharide-F originating in *Kjellmaniella crassifolia* and 0.01% of a defoaming agent (KM70 mfd. by Shin-Etsu Chemical Co., Ltd.) and sterilized at 120° C. for 20 minutes. After cooling, the medium is inoculated with 600 ml of the above-mentioned seed culture, which is then incubated therein at 24° C. for 24 hours under aerating at a rate of 10 l/min and agitating at 250 rpm. After the completion of the incubation, the culture medium is centrifuged to thereby give the cells and the culture supernatant. The culture supernatant thus obtained is concentrated with an ultrafilter with a fractional molecular weight of 10,000 and salted out with the use of 85% ammonium sulfate. The precipitate thus formed is taken up by centrifugation and thoroughly dialyzed against a 20 mM Tris hydrochloride buffer (pH 8.2) containing artificial seawater diluted 10-fold. Thus 600 ml of a crude enzyme is obtained.

40 ml of the crude enzyme thus obtained, 44 ml of artificial seawater, 510 mg of the above-mentioned sulfated-fucose-containing polysaccharide-F and 36 ml of water are mixed together and the pH value of the mixture is adjusted to 8. After reacting at 25° C. for 48 hours, the reaction mixture is subjected to gel filtration by using Cellulofine GCL-300 and thus divided into four fractions which are referred to, in order of molecular weight, as F-Fd-1 (molecular weight: more than 25,000), F-Fd-2 (molecular weight: 12,000–25,000), F-Fd-3 (molecular weight: 6,500–12,000) and F-Fd-4 (molecular weight: 6,500 or less). These fractions are desalted and freeze-dried to thereby give 170, 270, 300 and 340 mg of the dry preparations respectively.

Figure 22:
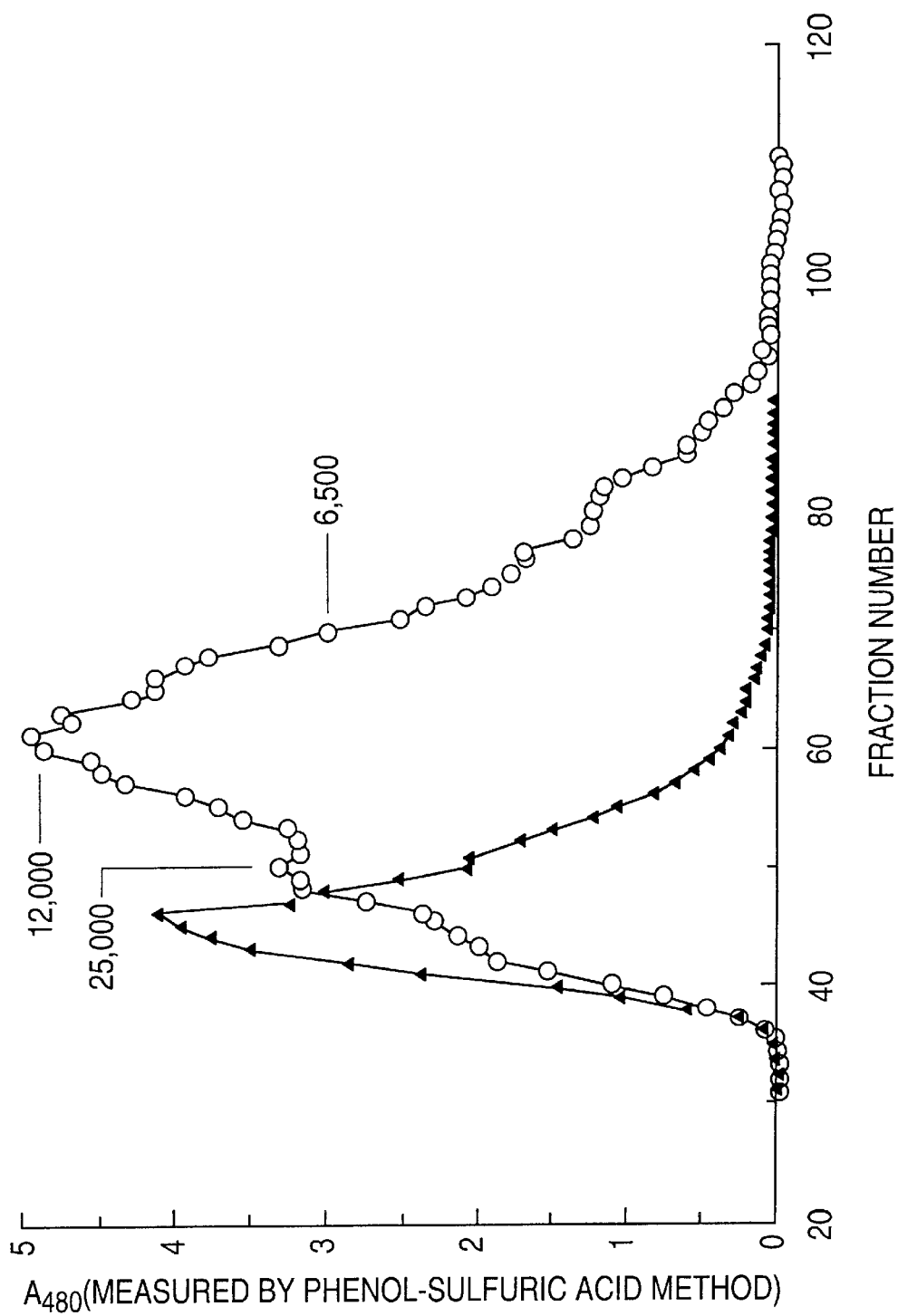
FIG. 22 shows the molecular weight distributions of the sulfated-fucose-containing polysaccharide-F determined by the gel filtration method with the use of Cellulofine GCL-300 before and after degrading with the endo-sulfated-fucose-containing polysaccharide degrading enzyme obtained by the present invention.

FIG. 22 shows the results of gel filtration with Cellulofine GCL-300 of the enzymatic digestion products of the sulfated-fucose-containing polysaccharide-F, i.e., the degradation products. In FIG. 22, the ordinate refers to the absorbance at 480 nm (color development determined by the phenol-sulfuric acid method) while the abscissa refers to the fraction number. Each fraction has 10 ml of the eluate. The column is 1,075 ml in volume and a 0.2 M solution of ammonium acetate containing 10% of ethanol is employed as the eluent.

In FIG. 22, the open circle shows the result of the gel filtration of the sulfated-fucose-containing polysaccharide-F which has been degraded with the enzyme, while the solid triangle stands for the results of the gel filtration of the sulfated-fucose-containing polysaccharide-F prior to the enzymatic degradation.

The above-mentioned results of the Cellulofine GCL-300 gel filtration indicate that the reaction product of the sulfated-fucose-containing polysaccharide degrading enzyme of the present invention shows a molecular weight distribution ranging from about 1,000 to 30,000.

(2) Analysis on Reducing-End Saccharide and Neutral Saccharide Composition in Enzymatic Reaction Product:

A portion of each of the above-mentioned F-Fd-1, F-Fd-2, F-Fd-3 and F-Fd-4 is sampled and the reducing end thereof is pyridyl-(2)-aminated (PA) by using GlycoTAG and GlycoTAG Reagent Kit. The (PA-F-Fd-1), (PA-F-Fd-2), (PA-F-Fd-3) and (PA-F-Fd-4) thus obtained are hydrolyzed by treating with 4 N hydrochloric acid at 100° C. for 3 hours and the reducing-end saccharides are examined by HPLC.

The HPLC is effected under the following conditions:

| apparatus | Model L-6200 (mfd. by Hitachi, Ltd.); |
|---|---|
| column | PALPAK Type A (4.6 mm × 150 mm) (mfd. by Takara Shuzo Co., Ltd.); |

-continued

| eluent | 700 mM borate buffer (pH 9.0): acetonitrile = 9:1; |
|---|---|
| detection | Fluorometric Detector F-1150 (mfd. by Hitachi, Ltd.), excitation wavelength: 310 nm, fluorescent wavelength: 380 nm; |
| flow rate | 0.3 ml/min; |
| column temperature | 65° C. |

As a result, it is found out that (PA-F-Fd-1), (PA-F-Fd-2), (PA-F-Fd-3) and (PA-F-Fd-4) all carry fucose as the reducing-end saccharide.

Further, the neutral saccharide compositions of F-Fd-1, F-Fd-2, F-Fd-3 and F-Fd-4 are determined in the following manner. The sulfated-fucose-containing polysaccharide-F employed as the substrate is hydrolyzed with sulfuric acid and the reducing ends of the constituting saccharides thereof are pyridyl-(2)-aminated (PA) by using GlycoTAG and GlycoTAG Reagent Kit and then analyzed by HPLC under the same conditions as those employed in the analysis of the above enzymatic reaction products. As a result, only fucose and galactose having L- and D-configurations respectively are detected. Thus only L-fucose and D-galactose are examined regarding the products.

Namely, the contents of D-galactose, which is one of the constituting saccharides, are determined in the following manner. By using F-Kit Lactose/Galactose (mfd. by Boehringer Mannheim-Yamanouchi), a reaction system by which D-galactose alone can be determined is constructed in accordance with the manufacturer's description. Separately, F-Fd-1, F-Fd-2, F-Fd-3 and F-Fd-4 are hydrolyzed with 4 N hydrochloric acid at 100° C. for 2 hours and, after neutralization, subjected to the determination in this reaction system.

On the other hand, the contents of L-fucose, which is another constituting saccharide, are determined in the following manner. In accordance with the method described in Clinical Chemistry, 36, 474–476 (1990), F-Fd-1, F-Fd-2, F-Fd-3 and F-Fd-4 are hydrolyzed with 4 N hydrochloric acid at 100° C. for 2 hours and, after neutralization, subjected to the determination in this reaction system.

As a result, it is found out that F-Fd-1, F-Fd-2, F-Fd-3 and F-Fd-4 show L-fucose to D-galactose ratios of 100:44, 100:27, 100:5 and 100:1, respectively.

These results may be summarized as follows. The endo-sulfated-fucose-containing polysaccharide degrading enzyme of the present invention acts on the sulfated-fucose-containing polysaccharide-F and hydrolyzes the fucosyl bonds, thus forming degradation products of about 1,000 to 30,000 in molecular weight. Among these degradation products, one having a higher molecular weight shows a larger galactose content. All of these degradation products have L-fucose as the reducing end.

Next, the substrate specificity of this enzyme is examined by treating the sulfated-fucose-containing polysaccharide-U with the sulfated-fucose-containing polysaccharide degrading enzyme of the present invention.

Namely, 12 μl of a 2.5% solution of the sulfated-fucose-containing polysaccharide-U, 6 μl of a 1 M solution of calcium chloride, 12 μl of a 1 M solution of sodium chloride, 72 μl of a 50 mM imidazole buffer (pH 7.5) and 18 μl of the endo-sulfated-fucose-containing polysaccharide degrading enzyme of the present invention (1.6 mU/ml) are mixed together and reacted at 30° C. for 3 hours. Then the reaction mixture is treated at 100° C. for 10 minutes and centrifuged. Then the degree of degradation is measured by analyzing a 100 μl portion of the reaction mixture by HPLC.

As a control, use is made of a reaction mixture prepared by the same method but substituting the endo-sulfated-fucose-containing polysaccharide degrading enzyme of the present invention by the buffer employed for dissolving the endo-sulfated-fucose-containing polysaccharide degrading enzyme of the present invention therein. This control is also analyzed by HPLC.

The HPLC is effected under the following conditions:

| | |
|---|---|
| apparatus | Model L-6200 (mfd. by Hitachi, Ltd.); |
| column | OHpak KB-804 (8 mm × 300 mm, mfd. by Showa Denko K. K.); |
| eluent | 25 mM imidazole buffer (pH 8) containing 5 mM of sodium azide, 25 mM of calcium chloride and 50 mM of sodium chloride; |
| detection | differential refractometric detector (Shodex RI-71, mfd. by Showa Denko K. K.); |
| flow rate | 1 ml/min; |
| column temperature | 25° C. |

As a result, the sulfated-fucose-containing polysaccharide-U is not degraded at all by the sulfated-fucose-containing polysaccharide degrading enzyme of the present invention.

As described above, the present invention relates to an enzyme composition containing the above sulfated-fucose-containing polysaccharide degrading enzyme of the present invention and a calcium source.

Examples of the calcium source usable in a solid composition include calcium salts such as calcium chloride, calcium carbonate, calcium acetate, calcium oxide, calcium hydroxide and hydrates thereof. In a liquid composition wherein the calcium source has been dissolved, suspended or emulsified in a solvent such as water or an alcohol, on the other hand, the calcium source may be either such a single compound as those cited above or one having been ionized by, for example, dissolution.

These calcium sources are effective in activating or stabilizing the enzyme.

Accordingly, the above-mentioned enzyme composition may further contain additives commonly employed in the art depending on the purpose, so long as the above-mentioned effects of the calcium source are not deteriorated thereby.

Degradation products of the sulfated-fucose-containing polysaccharide-F can be prepared by treating a material containing the sulfated-fucose-containing polysaccharide-F with the sulfated-fucose-containing polysaccharide degrading enzyme of the present invention. As the material containing the sulfated-fucose-containing polysaccharide-F, use can be made of, for example, a purified sulfated-fucose-containing polysaccharide-F product, the above-mentioned sulfated-fucose-containing polysaccharide mixture or an extract of brown algae with an aqueous solvent. The material containing the sulfated-fucose-containing polysaccharide-F may be dissolved in a conventional manner. Although the sulfated-fucose-containing polysaccharides may be dissolved in the solution at the highest concentration, the concentration is usually determined by taking the workability and enzyme titer into consideration.

The solvent for the sulfated-fucose-containing polysaccharide-F solution may be appropriately selected from among water, buffers and the like depending on the purpose. The pH value of the solution usually falls within the neutral region and the enzymatic reaction is generally effected at about 30° C. The molecular weights of the degradation products can be regulated by controlling the amount of the enzyme, reaction time, etc.

Next, the degradation products are subjected to molecular weight fractionation to thereby give the degradation products of the sulfated-fucose-containing polysaccharide-F with more uniform molecular weight distribution. The molecular weight fractionation may be carried out by using commonly employed procedures such as gel filtration or the use of a molecular weight fractionation membrane. The degradation products may be further subjected to purifying treatments with, for example, an ion exchange resin or activated carbon, if needed. It is also possible that the degradation products are desalted, sterilized and freeze-dried to thereby give a dry preparation of the degradation products of the present invention, if necessary.

EXAMPLES

To further illustrate the present invention in greater detail, and not by way of limitation, the following Examples will be given wherein percentage is given by weight.

Example 1

2 kg of thoroughly dried *Kjellmaniella crassifolia* was ground with a free mill (mfd. by Nara Kikai Seisakusho). The dry powder thus obtained was suspended in 9 l of 80% ethanol and treated at 80° C. for 2 hours. Then the mixture was filtered through a filter paper to thereby give the residue. This residue was repeatedly washed with ethanol and filtered thrice in the same manner as described above to thereby give the residue after ethanol-washing. This residue was suspended in 40 l of water, treated at 95° C. for 2 hours and filtered. The residue was washed with hot water to thereby give 36 l of an extract containing the sulfated-fucose-containing polysaccharides of *Kjellmaniella crassifolia*. 1.8 l of the extract thus obtained was freeze-dried to thereby give 15.4 g of a sulfated-fucose-containing polysaccharide preparation. To the residual extract was added sodium chloride to give a concentration of 0.4 M. Further, 5% cetylpyridinium chloride was added thereto until no precipitates were formed any more. Then the precipitates were collected by centrifugation and suspended in 3 l of a 0.4 M aqueous solution of sodium chloride followed by centrifugation and washing. After repeating this washing procedure thrice, 1 l of a 4 M aqueous solution of sodium chloride was added to the precipitate. After stirring well, ethanol was added thereto so as to give a concentration of 80%. Then the mixture was stirred and centrifuged to thereby give the precipitate. The precipitate was suspended in 80% ethanol and centrifuged. These procedures were repeated until the absorbance of the supernatant at 260 nm reached 0. The precipitate was dissolved in 3 l of a 2 M aqueous solution of sodium chloride. After removing the insoluble matters by centrifugation, 100 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 to thereby completely eliminate the coloring matters and sodium chloride. Next, the insoluble matters were eliminated by centrifugation followed by filtration and freeze-drying. The freeze-dried sulfated-fucose-containing polysaccharide mixture weighed 76 g.

Example 2

2 kg of thoroughly dried *Laminaria japonica* was ground with a free mill (mfd. by Nara Kikai Seisakusho). The dry powder thus obtained was suspended in 9 l of 80% ethanol and treated at 80° C. for 2 hours. Then the mixture was filtered through a filter paper to thereby give the residue. This residue was repeatedly washed with ethanol and filtered thrice in the same manner as described above to thereby give the residue after ethanol-washing. This residue was suspended in 40 l of water, treated at 95° C. for 2 hours and filtered. The residue was washed with hot water to thereby give 36 l of an extract containing the sulfated-fucose-containing polysaccharides of *Laminaria japonica*. To the extract was added sodium chloride to give a concentration of 0.4 M. Further, 5% cetylpyridinium chloride was added thereto until no precipitates were formed any more. Then the precipitates were collected by centrifugation and suspended in 3 l of a 0.3 M aqueous solution of sodium chloride followed by centrifugation and washing. After repeating this washing procedure thrice, 1 l of a 4 M aqueous solution of sodium chloride was added to the precipitate. After stirring well, ethanol was added thereto so as to give a concentration of 80%. Then the mixture was stirred and centrifuged to thereby give the precipitate. The precipitate was suspended in 80% ethanol and centrifuged. These procedures were repeated until the absorbance of the supernatant at 260 nm reached 0. The precipitate was dissolved in 3 l of a 2 M aqueous solution of sodium chloride. After removing the insoluble matters by centrifugation, 100 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 or less to thereby completely eliminate the coloring matters and sodium chloride. Next, the insoluble matters were eliminated by centrifugation and filtration followed by freeze-dryng. The freeze-dried sulfated-fucose-containing polysaccharide mixture weighed 52 g.

Example 3

Extraction of *Laminaria japonica* Sulfated-Fucose-Containing Polysaccharide Mixture:

2 kg of thoroughly dried *Laminaria japonica* was ground with a free mill (mfd. by Nara Kikai Seisakusho). The dry powder thus obtained was suspended in 9 l of 80% ethanol and treated at 80° C. for 2 hours. Then the mixture was filtered through a filter paper to thereby give the residue. This residue was repeatedly washed with ethanol and filtered thrice in the same manner as described above to thereby give the residue after ethanol-washing. This residue was suspended in 36 l of a 0.2 M solution of calcium acetate, treated at 95° C. for 2 hours and filtered. The residue was washed with 4 l of a 0.2 M solution of calcium acetate to thereby give 36 l of an extract containing the sulfated-fucose-containing polysaccharides of *Laminaria japonica*.

Example 4

Preparation of *Laminaria japonica* Sulfated-Fucose-Containing Polysaccharide Mixture To the filtrate obtained in Example 3 was added 5% cetylpyridinium chloride until no precipitates were formed any more. Then the precipitates were collected by centrifugation and suspended in 3 l of a 0.3 M aqueous solution of sodium chloride followed by centrifugation and washing. After repeating this washing procedure thrice, 1 l of a 4 M aqueous solution of sodium chloride was added to the precipitate. After stirring well, ethanol was added thereto so as to give a concentration of 80%. Then the mixture was stirred and centrifuged to thereby give the precipitate. The precipitate was suspended in 80% ethanol and centrifuged. These procedures were repeated until the absorbance of the supernatant at 260 nm reached 0. The precipitate was dissolved in 3 l of a 2 M aqueous solution of sodium chloride. After removing the insoluble matters by centrifugation, 100 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 or less to thereby completely eliminate the coloring matters and sodium chloride. Next, the insoluble matters were eliminated by centrifugation and filtration followed by freeze-drying. The freeze-dried sulfated-fucose-containing polysaccharide mixture weighed 52 g. This sulfated-fucose-containing polysaccharide mixture contained no coloring matter adsorbed by polysaccharide resins.

Example 5

Four portions of 1 g of the freeze-dried sulfated-fucose-containing polysaccharide mixture described in Example 4 were weighed out and dissolved respectively in water, 0.2 M sodium chloride, 0.2 M calcium chloride and 0.2 M magnesium chloride. Next, four DEAE-Sepharose FF columns of 500 ml in volume were prepared. Among these columns, two were equilibrated with 0.2 M sodium chloride, while the other two were equilibrated respectively with 0.2 M calcium chloride and 0.2 M magnesium chloride. One of the columns equilibrated with 0.2 M sodium chloride was washed with water in an amount 10 times as much as the column volume. Next, the sulfated-fucose-containing polysaccharide mixture samples dissolved in water, sodium chloride, calcium chloride and magnesium chloride were fed into the DEAE-Sepharose FF columns which had been equilibrated respectively with water, sodium chloride, calcium chloride and magnesium chloride. Then each column was thoroughly washed with the solution employed in the equilibration and developed by linear gradient elution with sodium chloride of 0 to 4 M. As a result, the whole sulfated-fucose-containing polysaccharide mixtures were adsorbed by the columns exclusively in the systems with the use of calcium chloride and magnesium chloride. On the other hand, the sulfated-fucose-containing polysaccharides were adsorbed only in a small amount corresponding to 0.4 g by the columns equilibrated with water and sodium chloride.

In each column, the sulfated-fucose-containing polysaccharide-F of the present invention was substantially separated from the sulfated-fucose-containing polysaccharide-U.

Example 6

2 kg of thoroughly dried *Kjellmaniella crassifolia* was ground with a free mill (mfd. by Nara Kikai Seisakusho). The dry powder thus obtained was suspended in 9 l of 80% ethanol and treated at 80° C. for 2 hours. Then the mixture was filtered through a filter paper to thereby give the residue.

This residue was repeatedly washed with ethanol and filtered thrice in the same manner as described above to thereby give the residue after ethanol-washing. This residue was suspended in 36 l of a 0.2 M solution of calcium acetate, treated at 95° C. for 2 hours and filtered. The residue was washed with 4 l of a 0.2 M solution of calcium acetate to thereby give 36 l of an extract containing the sulfated-fucose-containing polysaccharides of *Kjellmaniella crassifolia*.

This filtrate was concentrated to 2 l with the use of an ultrafilter provided with an ultrafiltration membrane of exclusion molecular weight of 100,000. Next, sodium chloride was added thereto so as to give a final concentration of 1.5 M. Further, 5% cetylpyridinium chloride was added thereto until no precipitates were formed any more. Then the precipitates were removed by centrifugation and the supernatant thus obtained was concentrated to 1 l by ultrafiltration. After adding 4 l of ethanol, the precipitates thus formed were collected by centrifugation. To this precipitate was added 100 ml of a 4 M aqueous solution of sodium chloride followed by stirring well. Then ethanol was added thereto to give a concentration of 80% and the mixture was stirred and centrifuged. The obtained precipitate was suspended in 80% ethanol and centrifuged. These procedures were repeated until the absorbance of the supernatant at 260 nm reached 0. The precipitate was dissolved in 2 l of a 2 M aqueous solution of sodium chloride. After removing the insoluble matters by centrifugation, 50 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 or less to thereby completely eliminate the coloring matters and sodium chloride. Next, the insoluble matters were eliminated by centrifugation and filtration followed by freeze-drying. The freeze-dried sulfated-fucose-containing polysaccharide-U weighed 15 g. This sulfated-fucose-containing polysaccharide-U of the present invention contained no coloring matter adsorbed by polysaccharide resins.

When treated with the above-mentioned endofucoidanase, this sulfated-fucose-containing polysaccharide-U was degraded to thereby give the oligosaccharides represented by the above formulae (I), (II) and (III).

Example 7

2 kg of thoroughly dried *Kjellmaniella crassifolia* was ground with a free mill (mfd. by Nara Kikai Seisakusho). The dry powder thus obtained was suspended in 9 l of 80% ethanol and treated at 80° C. for 2 hours. Then the mixture was filtered through a filter paper to thereby give the residue. This residue was repeatedly washed with ethanol and filtered thrice in the same manner as described above to thereby give the residue after ethanol-washing. This residue was suspended in 36 l of a 0.2 M solution of calcium acetate, treated at 95° C. for 2 hours and filtered. The residue was washed with 4 l of a 0.2 M solution of calcium acetate to thereby give 36 l of an extract containing the sulfated-fucose-containing polysaccharides of *Kjellmaniella crassifolia*. To the filtrate thus obtained was added 5% cetylpyridinium chloride until no precipitates were formed any more. Then the precipitates were collected by centrifugation and suspended in 3 l of a 0.4 M aqueous solution of sodium chloride followed by centrifugation and washing. After repeating this washing procedure thrice, 1 l of 4 M aqueous solution of sodium chloride was added to the precipitate and the mixture was well stirred. Then ethanol was added thereto so as to give a concentration of 80% and the mixture was stirred and centrifuged to thereby give the precipitate. The obtained precipitate was suspended in 80% ethanol and centrifuged. These procedures were repeated until the absorbance of the supernatant at 260 nm reached 0. The precipitate was dissolved in 3 l of a 2 M aqueous solution of sodium chloride. After removing the insoluble matters by centrifugation, 100 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 or less to thereby completely eliminate the coloring matters and sodium chloride. Next, the insoluble matters were eliminated by centrifugation and filtration followed by freeze-drying. The freeze-dried sulfated-fucose-containing polysaccharide mixture weighed 90 g. This sulfated-fucose-containing polysaccharide mixture contained no coloring matter adsorbed by polysaccharide resins. 7 g of this freeze-dried sulfated-fucose-containing polysaccharide mixture was weighed out and dissolved in 0.2 M calcium chloride. Then 4,000 ml of a DEAE-Sepharose FF column was equilibrated with 0.2 M calcium chloride. The sulfated-fucose-containing polysaccharide mixture dissolved in the 0.2 M calcium chloride was fed into the DEAE-Sepharose FF column and thoroughly washed with 0.2 M calcium chloride. Next, it was developed by linear gradient elution with sodium chloride of 0 to 4 M. Among the fractions thus eluted, those having sodium chloride concentration of 0.05 to 0.8 M were combined, desalted by dialysis and then freeze-dried. Thus 2.1 g of the sulfated-fucose-containing polysaccharide-U substantially separated from the sulfated-fucose-containing polysaccharide-F was obtained.

Among the fraction eluted above, those having sodium chloride concentration of 0.9 to 1.5 M were combined, desalted by dialysis and then freeze-dried. Thus 4.7 g of the sulfated-fucose-containing polysaccharide-F substantially separated from the sulfated-fucose-containing polysaccharide-U was obtained.

Example 8

Production of Sulfated-Fucose-Containing Polysaccharide-F:

1.2 g of the sulfated-fucose-containing polysaccharide mixture obtained in Example 7 was weighed out and dissolved in a 1.5 M solution of sodium chloride in such a manner as to give a final concentration of 0.2%. Next, 1.25% of cetylpyridinium chloride in a 1.5 M sodium chloride solution was added thereto until no precipitates were formed any more. Then the precipitates were collected by centrifugation and suspended in 500 ml of a 1.5 M aqueous solution of sodium chloride followed by centrifugation and washing. After repeating this washing procedure thrice, 1 l of a 4 M aqueous solution of sodium chloride was added to the precipitate and the mixture was well stirred. Then ethanol was added thereto so as to give a concentration of 80% and the mixture was stirred and centrifuged to thereby give the precipitate. The precipitate was suspended in 80% ethanol and centrifuged. These procedures were repeated until the absorbance of the supernatant at 260 nm reached 0. The precipitate was dissolved in 500 ml of a 2 M aqueous solution of sodium chloride. After removing the insoluble matters by centrifugation, 1 ml of DEAE-Cellulofine A-800 (mfd. by Seikagaku Kogyo) equilibrated with a 2 M aqueous solution of sodium chloride was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafilter provided with a hollow fiber of exclusion molecular weight of 100,000 or less to thereby completely eliminate the coloring matters and sodium chloride. Next, the insoluble matters were eliminated by centrifugation followed by ultrafiltration and freeze-drying. The freeze-dried sulfated-fucose-containing polysaccharide-F weighed 710 mg. This sulfated-fucose-containing polysaccharide-F contained no coloring matter adsorbed by polysaccharide resins. This sulfated-fucose-containing polysaccharide-F was the sulfated-fucose-containing polysaccharide-F of the present invention being free from uronic acid and containing fucose as the main component of the constituting saccharides.

Example 9
Method for Enzymatic Purification of Sulfated-Fucose-Containing Polysaccharide-F:

10 g of the sulfated-fucose-containing polysaccharide mixture obtained in Example 7 was weighed out and dissolved in 500 ml of artificial seawater. Next, 5 U of the above-mentioned endofucoidanase originating in Flavobacterium sp. SA-0082 (FERM BP-5402) was added thereto and reacted at 25° C. for 50 hours. The reaction mixture was ultrafiltered with an ultrafilter provided with a hollow fiber of exclusion molecular weight of 100,000 or less. After completely removing low-molecular weight substances, the insoluble matters were eliminated by centrifugation and filtration followed by freeze-drying. The freeze-dried sulfated-fucose-containing polysaccharide-F weighed 6 g. This sulfated-fucose-containing polysaccharide-F contained no coloring matter adsorbed by polysaccharide resins. It was found out that this sulfated-fucose-containing polysaccharide-F was the sulfated-fucose-containing polysaccharide-F of the present invention being free from uronic acid and containing fucose as the main component of the constituting saccharides.

Example 10
Method for Incubative Purification of Sulfated-Fucose-Containing Polysaccharide-F:

60 g of the sulfated-fucose-containing polysaccharide mixture obtained in Example 7 was weighed out and dissolved in 20 l of artificial seawater. Next, 200 g of peptone and 4 g of yeast extract were added thereto. After feeding into a 30 l jar fermenter and sterilizing, it was inoculated with the above-mentioned Flavobacterium sp. SA-0082 (FERM BP-5402) which was then incubated at 25° C. for 24 hours. After centrifuging to thereby eliminate the cells, the culture medium was ultrafiltered with an ultrafilter provided with a hollow fiber of exclusion molecular weight of 100,000 or less. After completely removing low-molecular weight substances, the insoluble matters were eliminated by centrifugation and filtration followed by freeze-drying. The freeze-dried sulfated-fucose-containing polysaccharide-F weighed 36 g. This sulfated-fucose-containing polysaccharide-F contained no coloring matter adsorbed by polysaccharide resins. It was found out that this sulfated-fucose-containing polysaccharide-F was the sulfated-fucose-containing polysaccharide-F of the present invention being free from uronic acid and containing fucose as the main component of the constituting saccharides.

Example 11

Four portions of 1 g of the freeze-dried sulfated-fucose-containing polysaccharide mixture described in Example 7 were weighed out and dissolved respectively in water, 0.2 M sodium chloride, 0.2 M calcium chloride and 0.2 M magnesium chloride. Next, four DEAE-Sepharose FF columns of 500 ml in volume were prepared. Among these columns, two were equilibrated with 0.2 M sodium chloride, while the other two were equilibrated respectively with 0.2 M calcium chloride and 0.2 M magnesium chloride. One of the columns equilibrated with 0.2 M sodium chloride was washed with water in an amount 10 times as much as the column volume. Next, the sulfated-fucose-containing polysaccharide mixture samples dissolved in water, sodium chloride, calcium chloride and magnesium chloride were fed into the DEAE-Sepharose FF columns which had been equilibrated respectively with water, sodium chloride, calcium chloride and magnesium chloride. Then each column was thoroughly washed with the solution employed in the equilibration and developed by linear gradient elution with sodium chloride of 0 to 4 M. As a result, the whole sulfated-fucose-containing polysaccharide mixtures were adsorbed by the columns only in the systems with the use of calcium chloride and magnesium chloride. On the other hand, the sulfated-fucose-containing polysaccharides were adsorbed only in a small amount corresponding to 0.4 g by the columns equilibrated with water and sodium chloride.

In each column the sulfated-fucose-containing polysaccharide-F of the present invention was substantially separated from the sulfated-fucose-containing polysaccharide-U.

Example 12

7 g of the sulfated-fucose-containing polysaccharide mixture described in Example 1 was weighed out and dissolved in 800 ml of 0.2 M calcium chloride. Next, a 4 l DEAE-Sepharose FF column was equilibrated with 0.2 M calcium chloride and the whole solution of the sulfated-fucose-containing polysaccharide described above was fed into the column. After washing with 8 l of a 0.2 M solution of calcium chloride, it was developed by linear gradient elution with sodium chloride of 0 to 4 M. Among the fractions thus eluted, those from which uronic acid was detected (sodium chloride concentration: about 0.9 M or less, the sulfated-fucose-containing polysaccharide-U) and those from which no uronic acid was detected (sodium chloride concentration: at about 1.2 M, the sulfated-fucose-containing polysaccharide-F) were each desalted and freeze-dried. Thus 1.4 g and 4.8 g of dry preparations were obtained respectively.

Example 13

The sulfated-fucose-containing polysaccharide mixture obtained in Example 1 was treated with the endofucoidanase produced by Flavobacterium sp. SA-0082 (FERM BP-5402). Thus oligosaccharides having the following structures were formed:

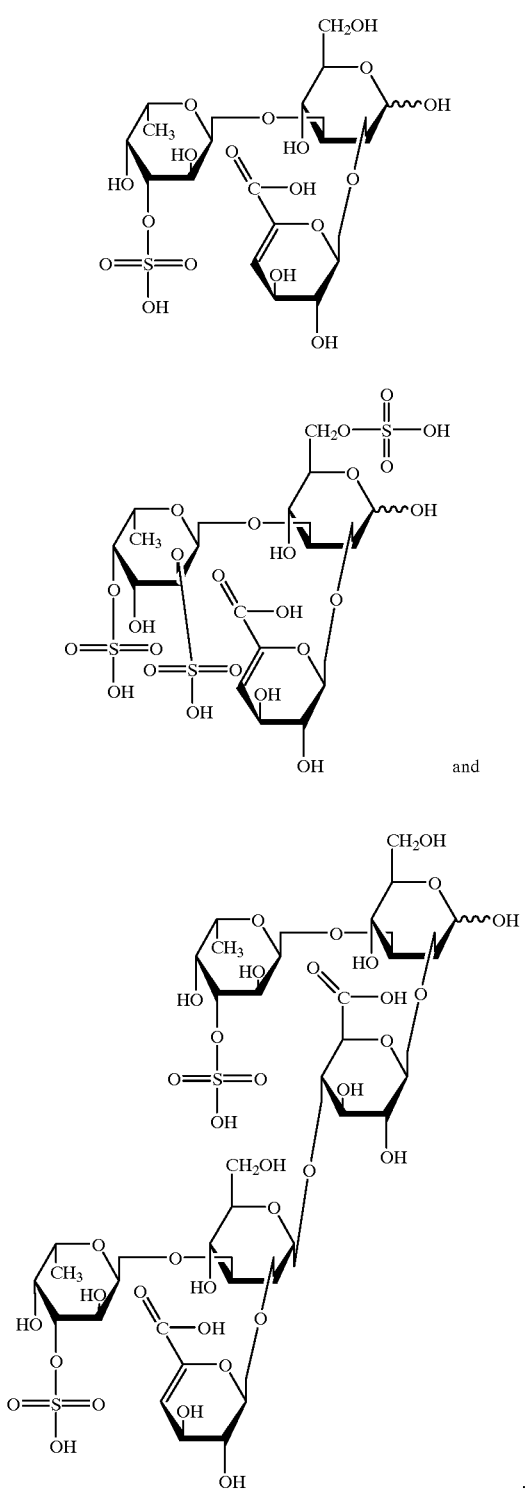

The present inventors effected the enzymatic reaction as described below and thus obtained the above-mentioned oligosaccharides.

Namely, 80 ml of a 2.5% solution of the sulfated-fucose-containing polysaccharide mixture of Example 1, 60 ml of a 50 mM phosphate buffer solution (pH 7.5), 20 ml of 4 M sodium chloride and 40 ml of a 32 mU/ml solution of the endofucoidanase were mixed together and reacted at 25° C. for 48 hours.

Then the reaction mixture was subjected to molecular weight fractionation by using a Cellulofine GCL-300 column (mfd. by Seikagaku Kogyo) and fractions of molecular weight of 2,000 or less were combined. After desalting with Micro Acilyzer G3, it was separated into three fractions by using DEAE-Sepharose FF followed by desalting again and freeze-drying. Thus 250 mg, 310 mg and 52 mg of the oligosaccharides of the above formulae (I), (II) and (III) were obtained respectively.

Example 14

10 g of the sulfated-fucose-containing polysaccharide mixture obtained in Example 1 was dissolved in 500 ml of 0.2 M citric acid and the pH value of the obtained solution was adjusted to 2.9. Then it was treated at 100° C. for 3 hours. To the hydrolyzate thus obtained was added 150 ml of a 1 M solution of calcium acetate. After removing the precipitate thus formed by centrifugation, it was subjected to molecular weight fractionation by gel filtration with the use of Cellulofine GCL-25 (molecular weight: >5,000, 5,000–3,000, 3,000–2,000, 2,000–1,000, 1,000–500, <500). The obtained fractions were referred to as GFd-Oli-1, Gfd-Oli-2, GFd-Oli-3, GFd-Oli-4, GFd-Oli-5 and GFd-Oli-6 in the order of molecular weight (high→low). These six fractions were each desalted and freeze-dried. Thus, 2.3 g, 1.7 g, 0.88 g, 1.8 g, 1.4 g and 0.72 g of dry preparations were obtained respectively.

Example 15

60 g of the sulfated-fucose-containing polysaccharide mixture obtained in Example 1 was weighed out and dissolved in 20 l of artificial seawater. Next, 200 g of peptone and 4 g of yeast extract were added thereto. After feeding into a 30 l jar fermenter and sterilizing, it was inoculated with Flavobacteriu m sp. SA-0082 (FERM BP-5402), which was then incubated at 25° C. for 24 hours. After centrifuging to thereby eliminate the cells, the culture medium was ultrafiltered with an ultrafilter provided with a hollow fiber of exclusion molecular weight of 100,000 or less. After completely removing low-molecular weight substances, the insoluble matters were eliminated by centrifugation and filtration followed by freeze-drying. The freeze-dried sulfated-fucose-containing polysaccharide-F weighed 36 g.

Example 16

5 kg of *Stichopus japonicus* was dissected. Then the internals were removed and the somatic walls were collected. To 200 g of the wet somatic walls was added 500 ml of acetone. After treating with a homogenizer, the mixture was filtered and the residue was washed with acetone until the coloring matters were completely eliminated. The residue was then filtered under suction to thereby give 140 g of a dry product. To this dry product was added 2.8 l of a 0.4 M aqueous solution of sodium chloride. After treating at 100° C. for 1 hour, the mixture was filtered and the residue was thoroughly washed with a 0.4 M aqueous solution of sodium chloride. Thus 3.7 l of the extract was obtained. To this extract was added 5% cetylpyridinium chloride until no precipitates were formed any more. The precipitates thus formed were collected by centrifugation and then suspended in a 0.4 M aqueous solution of sodium chloride again followed by centrifugation. To the precipitate thus obtained was added 1 l of a 4 M aqueous solution of sodium chloride and the obtained mixture was treated with a homogenizer. Then 4 l of ethanol was added thereto under stirring. After stirring for 1 hour, the mixture was filtered to thereby give the precipitate. The obtained precipitate was suspended in 80% ethanol and centrifuged. These procedures were repeated until the absorbance of the supernatant at 260 nm reached 0. The precipitate was suspended in 2 l of a 2 M aqueous solution of sodium chloride and the insoluble matters were eliminated by centrifugation. The supernatant was completely desalted by ultrafiltering with an ultrafilter provided with a membrane of exclusion molecular weight of 30,000. After freeze-drying, 3.7 g of sulfated-fucose-containing polysaccharide were obtained.

Example 17

2 kg of thoroughly dried *Undaria pinnatifida* was ground with a free mill (mfd. by Nara Kikai Seisakusho). The dry powder thus obtained was suspended in 9 l of ethanol and treated at 75° C. for 1 hour. Then the mixture was filtered through a filter paper to thereby give the residue. To this residue was added 9 l of 80% ethanol and the mixture was stirred, treated at 80° C. for 1 hour and filtered through a filter paper to thereby give the residue. This residue was repeatedly washed with 80% ethanol and filtered thrice in the same manner as described above to thereby give 1,908 g of the residue after ethanol-washing. A 684 g portion of this residue was suspended in 9 l of 0.2 M calcium acetate and treated at 95° C. for 1 hour. After allowing to stand for 24 hours, the supernatant was obtained. To the precipitate obtained by eliminating the supernatant was added 9 l of 0.2 M calcium acetate and the mixture was stirred and allowed to stand for 1 hour to thereby give the supernatant. The supernatant thus obtained was combined with the supernatant obtained above. Then it was ultrafiltered with an ultrafilter provided with a hollow fiber of exclusion molecular weight of 10,000 and thus concentrated to 350 ml. The concentrate was then centrifuged. After removing the precipitate, it was subjected to ultrafiltration while adding 2 mM sodium chloride. After completely removing the calcium acetate, the residue was freeze-dried to thereby give 3.2 g of a freeze-dried product. This freeze-dried product contained 3.1 g of the sulfated-fucose-containing polysaccharide.

Example 18

(1) Preparation of *Kjellmaniella crassifolia* Sulfated-Fucose-Containing Polysaccharide Mixture 2 kg of dried *Kjellmaniella crassifolia* was ground with a free mill Model M-2 (mfd. by Nara Kikai Seisakusho). The dry powder thus obtained was treated in 4.5 times as much 80% ethanol at 80° C. for 2 hours and then filtered. The obtained residue was repeatedly washed with 80% ethanol and filtered thrice in the same manner as described above to thereby give 1,870 g of the residue after ethanol-washing. To this residue was added 36 l of water and the mixture was treated at 100° C. for 2 hours to thereby give the extract. The salt concentration of the extract was adjusted to the same level as that of a 400 mM solution of sodium chloride. Then 5% cetylpyridinium chloride was added thereto until no precipitate was formed any more. After centrifuging, the precipitate was repeatedly washed with 80% ethanol to thereby completely eliminate the cetylpyridinium chloride therefrom. Next, it was dissolved in 3 l of 2 M sodium chloride. After removing the insoluble matters by centrifugation, 100 ml of DEAE-Cellulofine A-800 equilibrated with 2 M sodium chloride was suspended therein. The suspension was stirred and then filtered to thereby remove the resin. The filtrate was fed into a 100 ml DEAE-Cellulofine A-800 column equilibrated with 2 M sodium chloride and the fraction passing therethrough was desalted and low-molecular weight matters were removed therefrom by using an ultrafilter (exclusion molecular weight of membrane: 100,000). The precipitate thus formed was eliminated by centrifugation. The supernatant was freeze-dried to thereby give 82.2 g of a purified *Kjellmaniella crassifolia* sulfated-fucose-containing polysaccharide mixture.

(2) Preparation of Sulfated-Fucose-Containing Polysaccharide-F 6 g of the above-mentioned sulfated-fucose-containing polysaccharide mixture originating in *Kjellmaniella crassifolia* was dissolved in 600 ml of 20 mM of sodium acetate (pH 6.0) containing 0.2 M of calcium chloride. Then the solution was fed into a 3600 ml DEAE-Sepharose FF column preliminarily equilibrated with 20 mM of sodium acetate (pH 6.0) containing 0.2 M of calcium chloride. Then the column was thoroughly washed with 20 mM of sodium acetate (pH 6.0) containing 0.2 M of calcium chloride and developed by linear gradient elution with sodium chloride of 0 to 2 M. Then the sulfated-fucose-containing polysaccharide-F fractions eluted at sodium chloride concentrations of 0.75 M or more and above were collected and desalted by using an ultrafilter provided with an ultrafiltration membrane of exclusion molecular weight of 100,000. After freeze-drying, 3.3 g of a freeze-dried preparation of the sulfated-fucose-containing polysaccharide-F was obtained.

(3) Preparation of Endo-Sulfated-Fucose-Containing Polysaccharide Degrading Enzyme Alteromonas sp. SN-1009 (FERM BP-5747) was inoculated into 600 ml of a medium comprising an artificial seawater (pH 8.2, mfd. by Jamarin Laboratory) containing 0.25% of glucose, 1.0% of peptone and 0.05% of yeast extract which had been sterilized (120° C., 20 minutes) and pipetted into a 2 l Erlenmeyer flask. Then the strain was incubated therein at 25° C. for 25 hours to thereby give a seed culture. Into a 30 l jar fermenter was fed 18 l of a medium comprising an artificial seawater (pH 8.0) containing 200 g of peptone, 4 g of yeast extract and 4 ml of a defoaming agent (KM70 mfd. by Shin-Etsu Chemical Co., Ltd.) and sterilized at 120° C. for 20 minutes. After cooling, the medium was inoculated with 20 g of the *Kjellmaniella carssifolia* sulfated-fucose-containing polysaccharide-F prepared by the method of Example 8, which had been separately dissolved in 2 l of artificial seawater sterilized at 120° C. for 15 minutes, and 600 ml of the above-mentioned seed culture followed by incubation at 24° C. for 20 hours under aerating at a rate of 10 1/min and agitating at 250 rpm. After the completion of the incubation, the culture medium was centrifuged to thereby give the cells and the culture supernatant.

When measured by using the sulfated-fucose-containing polysaccharide-F as the substrate, the culture supernatant showed an activity of the sulfated-fucose-containing polysaccharide degrading enzyme of the present invention of 5 mU/ml of the medium.

The culture supernatant was concentrated with an ultrafilter of a fractional molecular weight of 10,000 and the precipitate thus formed was eliminated by centrifugation. Then it was salted out with the use of 85% ammonium sulfate. The precipitate thus formed was taken up by centrifugation and thoroughly dialyzed against a 20 mM Tris hydrochloride buffer (pH 8.2) containing artificial seawater (Jamarin S) diluted 10-fold. Thus 400 ml of a crude enzyme was obtained.

The crude enzyme solution thus obtained was adsorbed by a DEAE-Cellulofine A-800 (mfd. by Seikagaku Kogyo)

column which had been equilibrated with a 20 mM Tris hydrochloride buffer (pH 8.2) containing 5 mM of sodium azide and artificial seawater (Jamarin S) diluted 10-fold. Then the adsorbed matters were thoroughly washed with the same buffer and eluted into the same buffer with the use of solutions containing 100 mM, 200 mM, 300 mM, 400 mM and 600 mM of sodium chloride. The active fractions were combined.

When measured by using the sulfated-fucose-containing polysaccharide-F as the substrate, this partially purified enzyme showed an activity of 10,200 mU (10.2 U). It was not contaminated with other sulfated-fucose-containing polysaccharides degrading enzyme.

A portion of the partially purified enzyme thus obtained was subjected to gel filtration through Sephacryl S-200 which had been equilibrated with a 10 mM Tris hydrochloride buffer (pH 8.0) containing 5 mM of sodium azide and artificial seawater (Jamarin S) diluted 10-fold. The molecular weight thereof thus determined was about 100,000.

(4) By using the partially purified enzyme obtained above and PA-FF respectively as an enzyme source and a substrate, examination was made on the effect of calcium concentration on the activity of this enzyme.

In the enzymatic reaction, use was made of a buffer (pH 7) containing 50 mM of acetic acid, imidazole and Tris hydrochloride. In the reaction mixture, sodium chloride was dissolved so as to give a final concentration of 400 mM.

Figure 23:
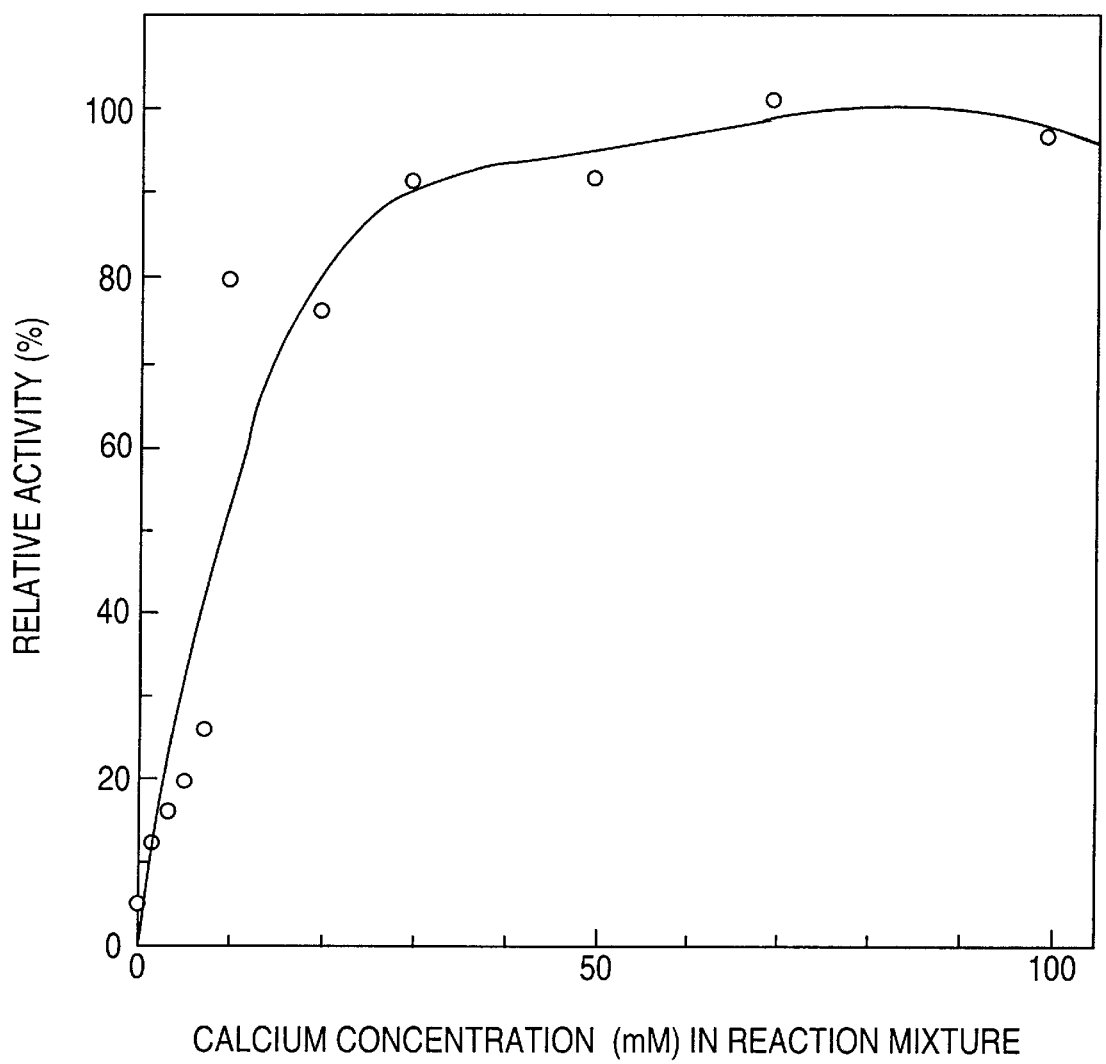
FIG. 23 is a graph which shows the relationship between the relative activity of the endo-sulfated-fucose-containing polysaccharide degrading enzyme obtained by the present invention and the calcium ion concentration in the reaction mixture.

The activity of the enzyme was measured while varying the calcium chloride concentration in the reaction mixture from 0 to 100 mM. FIG. 23 shows the results wherein the ordinate refers to the relative activity (%) while the abscissa refers to the calcium concentration (mM) in the reaction mixture.

Thus it has been found out that the activity of this enzyme is considerably elevated in the presence of a calcium salt.

(5) The endo-sulfated-fucose-containing polysaccharide degrading enzyme of the present invention was maintained at 5° C. for 20 hours under dialyzing against six buffers as specified below and then the residual activity was measured.
1. A 20 mM Tris hydrochloride buffer (pH 8.2).
2. A 20 mM Tris hydrochloride buffer (pH 8.2) containing 5 mM of sodium azide.
3. A 20 mM Tris hydrochloride buffer (pH 8.2) containing 5 mM of sodium azide and 50 mM of sodium chloride.
4. A 20 mM Tris hydrochloride buffer (pH 8.2) containing 5 mM of sodium azide and 500 mM of sodium chloride.
5. A 20 mM Tris hydrochloride buffer (pH 8.2) containing 5 mM of sodium azide, 50 mM of sodium chloride and 10 mM of calcium chloride.
6. A 20 mM Tris hydrochloride buffer (pH 8.2) containing 5 mM of sodium azide and artificial seawater (Jamarin S) diluted 10-fold.

As a result, the sulfated-fucose-containing polysaccharide degrading enzyme of the present invention was inactivated when dialyzed against the buffers 1, 2 and 3. On the other hand, the activity of this enzyme was sustained when dialyzed against the buffers 4, 5 and 6.

Based on these results, it has been found out that this enzyme is stabilized in the presence of 500 mM of sodium chloride or 10 mM of calcium ion.

(6) 5 g of the sulfated-fucose-containing polysaccharide-F prepared above was weighed out and mixed with 471 ml of a 50 mM imidazole buffer (pH 8), 12.5 ml of 4 M sodium chloride, 6.25 ml of 4 M calcium chloride and 10 ml (corresponding to 6 mU) of the partially purified sulfated-fucose-containing polysaccharide degrading enzyme of the present invention obtained in Example 18-(3). After reacting at 25° C. for 120 hours, a degradation product of the sulfated-fucose-containing polysaccharide-F was obtained.

Figure 24:
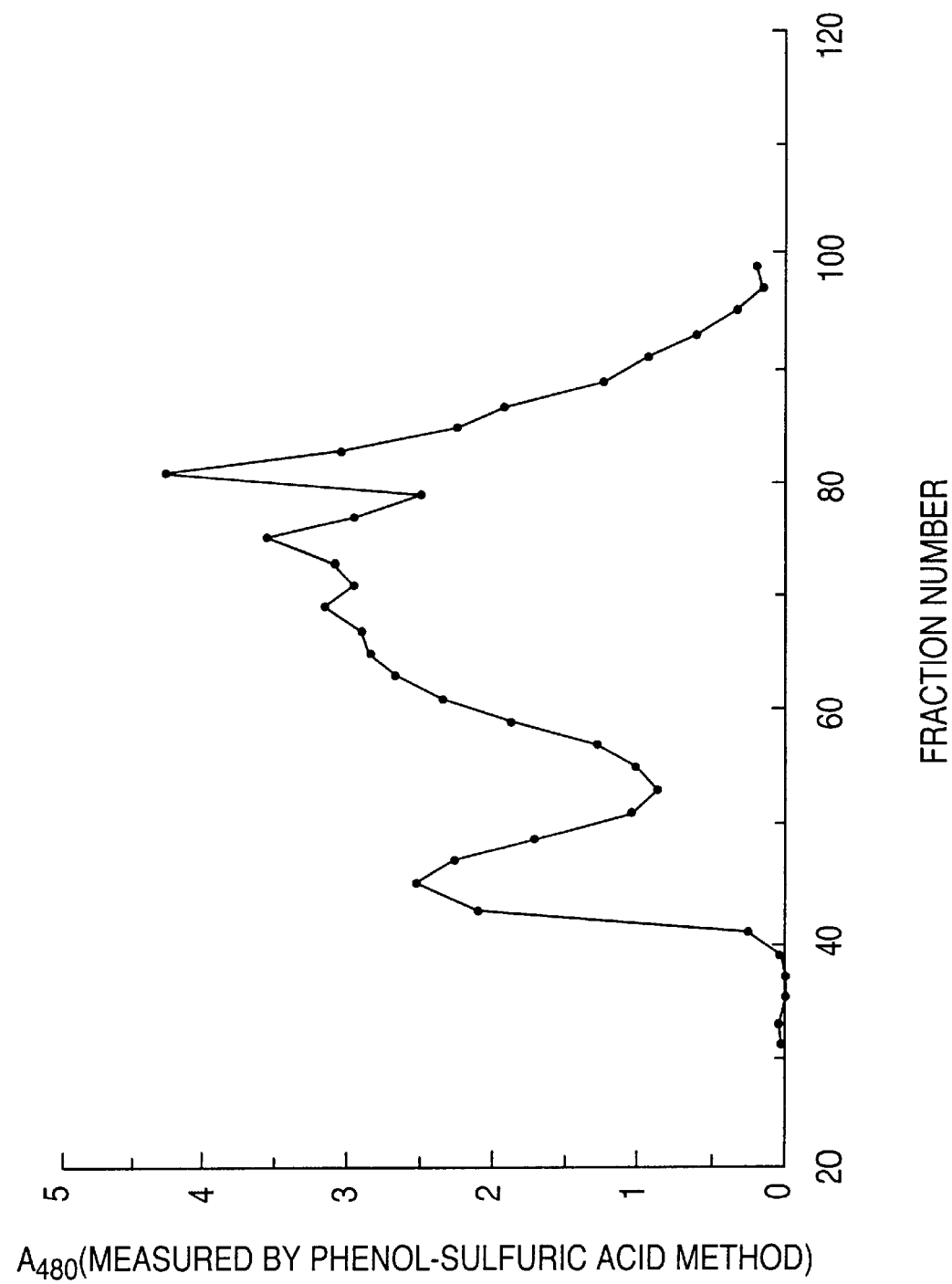
FIG. 24 shows the molecular weight distributions of the sulfated-fucose-containing polysaccharide-F which has been degraded with the endo-sulfated-fucose-containing polysaccharide degrading enzyme obtained by the present invention determined by the gel filtration method with the use of Cellulofine GCL-300 in Example 19-(6).
Figure 25:
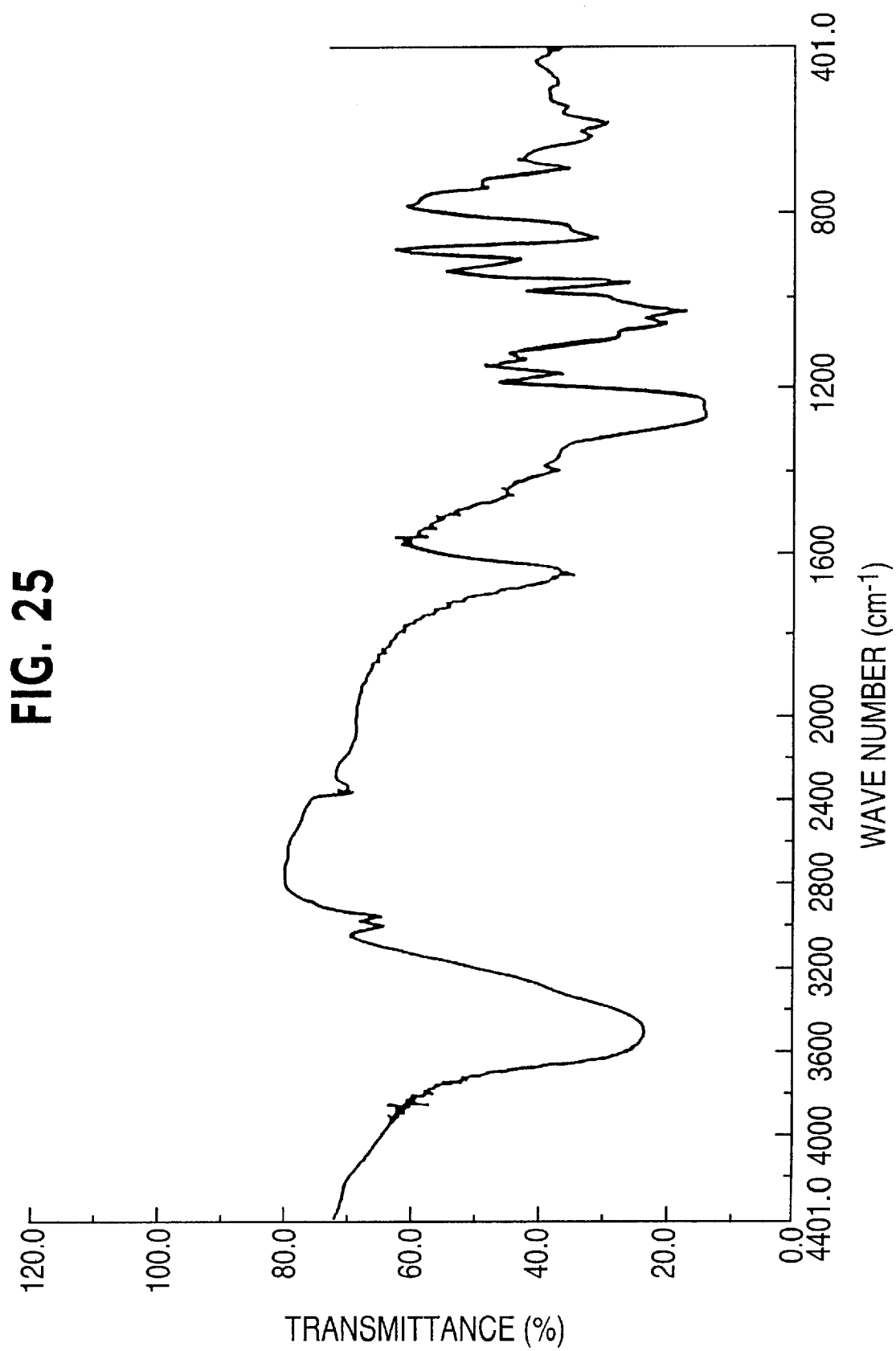
FIG. 25 is the IR spectrum of the sulfated-fucose-containing polysaccharide-F which has been degraded with the endo-sulfated-fucose-containing polysaccharide degrading enzyme obtained by the present invention.
Figure 26:
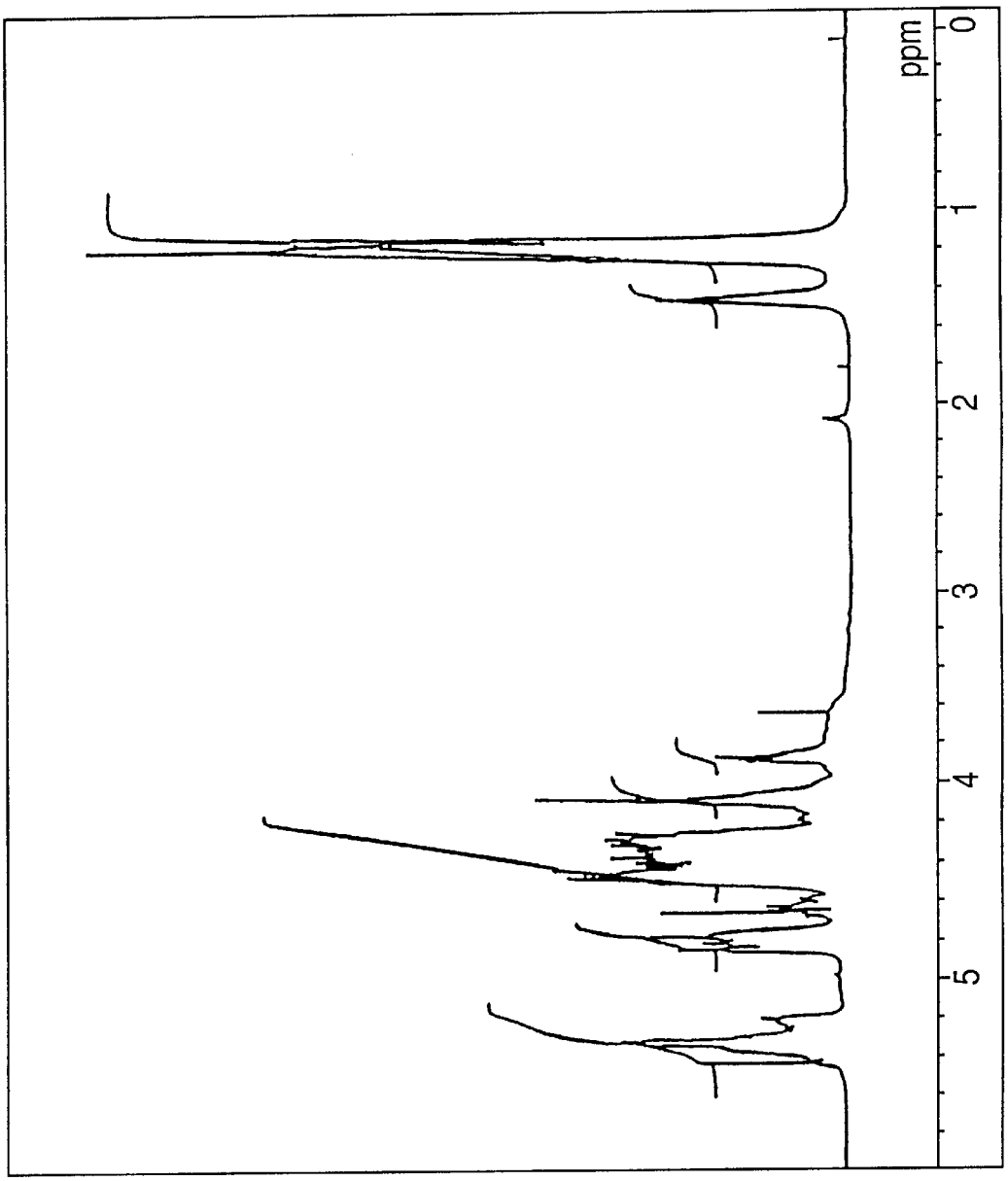
FIG. 26 is the $^1$H-NMR spectrum of the sulfated-fucose-containing polysaccharide-F which has been degraded with the endo-sulfated-fucose-containing polysaccharide degrading enzyme obtained by the present invention.

FIGS. 25 and 26 show respectively the IR and NMR analytical data of the degradation product obtained above. FIG. 24 shows the results of the gel filtration with the use of Cellulofine GCL-300. Namely, this substance shows a molecular weight distribution ranging from 1,000 to 30,000.

This substance contained 46% of sulfate in terms of $SO_4$ (molecular weight: 96) and showed a neutral saccharide composition of fucose and galactose (100:4).

In each of FIGS. 24 to 26, the ordinate and the abscissa have the same meanings respectively as those in FIGS. 2 to 4.

Example 19

Human premyelocytic leukemia cells HL-60 (ATCC CRL-1964) were incubated in RPMI 1640 medium (mfd. by Gibco) containing 10% of fetal calf serum (mfd. by JRH Bioscience) treated at 56° C. for 30 minutes and then suspended in ASF104 medium (mfd. by Ajinomoto Co., Ltd.) in such a manner as to give a concentration of $5 \times 10^5$ cells/9 ml. To four portions of 9 ml of this suspension were added 1 ml portions of 5 mg/ml solutions of the sulfated-fucose-containing polysaccharides obtained in Examples 1, 12 and 15 in physiological saline which had been treated by filtering through a cellulose acetate filter (pore size: 0.20 μm, mfd. by Corning; the same was employed in the subsequent filter treatment). After incubating at 37° C. for 40 hours in the presence of 5% of carbon dioxide, the cells were separated from the supernatant by centrifugation. The cells thus obtained were suspended in 20 μl of a 50 mM Tris hydrochloride buffer (pH 7.8) containing 10 mM of ethylenediaminetetraacetate and 0.5% of sodium lauroyl sarcosinate. Then 1 μl of 10 mg/ml Ribonuclease A (mfd. by Sigma) was added thereto and the mixture was treated at 50° C. for 30 minutes. After adding 1 μl of 10 mg/ml of Proteinase K, the mixture was treated at 50° C. for 1 hour. The cells thus treated were employed as a sample and electrophoresed in a 2% agarose gel under a constant voltage of 100 V. This gel was immersed in an ethidium bromide solution for 30 minutes and then the conditions of the DNA in the gel were examined by using a transilluminator. As a result, DNA ladders characteristic of apoptosis were observed therein. For the further confirmation, the above procedure was repeated using a 10 μg/ml solution of actinomycin D known as a reagent inducing apoptosis as a substitute for the above-mentioned sulfated-fucose-containing polysaccharides. As a result, DNA ladders were observed after incubating for 20 hours similar to the case of the sulfated-fucose-containing polysaccharides.

Based on these results, it has been clarified that the apoptosis of HL-60 cells can be induced by the sulfated-fucose-containing polysaccharides obtained in Examples 1, 12 and 15.

The sulfated-fucose-containing polysaccharides obtained in Examples 1, 12 and 15 were each dissolved in a 30 mM Hepes buffer (pH 7.2) containing 120 mM of sodium chloride so as to give a concentration of 5 mg/ml and treated in an autoclave at 121° C. for 20 minutes. Then the effects of these sulfated-fucose-containing polysaccharides of inducing apoptosis on HL-60 cells (ATCC CCL-240) were examined in the same manner as the one described above. Thus the same results were obtained.

Example 20

Human premyelocytic leukemia cells HL-60 (ATCC CCL-240) were incubated in RPMI 1640 medium (mfd. by Gibco) containing 10% of fetal calf serum (mfd. by JRH Bioscience) treated at 56° C. for 30 minutes and then suspended in ASF104 medium (mfd. by Ajinomoto Co., Ltd.) in such a manner as to give a concentration of $5 \times 10^5$ cells/9 ml. To 9 ml of this suspension was added 1 ml of a 5 mg/ml solution of the sulfated-fucose-containing polysaccharide obtained in Example 15 in physiological saline which had been treated with a filter. After incubating at 37° C. for 20 hours in the presence of 5% of carbon dioxide, the cells were separated from the supernatant by centrifugation. The cells thus obtained were subjected to Giemsa staining in accordance with the method described in "Apotoshisu Jikken Purotokoru", Shujun-sha, supervised by Yasuichi Tanuma, 93–95 (1995). Namely, the cells obtained above were fixed on a slide glass with the use of Carnoy's fixative (acetic acid:methanol=1:3), stained with Giemsa dye (mfd. by Merck & Co., Inc.) and observed under an optical microscope. Thus, nucleus fragments characteristic of apoptosis were observed. This fact indicated that the sulfated-fucose-containing polysaccharide obtained in Example 15 induced apoptosis of the HL-60 cells.

The sulfated-fucose-containing polysaccharide obtained in Example 15 were dissolved in a 30 mM Hepes buffer (pH 7.2) containing 120 mM of sodium chloride so as to give a concentration of 5 mg/ml and treated in an autoclave at 121° C. for 20 minutes. Then the effect of the sulfated-fucose-containing polysaccharide of inducing apoptosis was examined in the same manner as the one described above. Thus the same results were obtained.

Example 21

Human premyelocytic leukemia cells HL-60 (ATCC CCL-240) were incubated in RPMI 1640 medium (mfd. by Gibco) containing 10% of fetal calf serum (mfd. by JRH Bioscience) treated at 56° C. for 30 minutes and then suspended in ASF104 medium (mfd. by Ajinomoto Co., Ltd.) in such a manner as to give a concentration of $5 \times 10^5$ cells/4.5 ml. To four portions of 4.5 ml of this suspension were added 0.5 ml portions of 10 mg/ml solutions of the sulfated-fucose-containing polysaccharides obtained in Examples 1, 15 and 17 in 30 mM Hepes buffer (pH 7.2) containing 120 mM of sodium chloride which had been treated in an autoclave at 121° C. for 20 minutes. After incubating at 37° C. in the presence of 5% of carbon dioxide, the cells were counted by the Trypan Blue staining method 24 hours and 40 hours after the initiation of the incubation.

Figure 27:
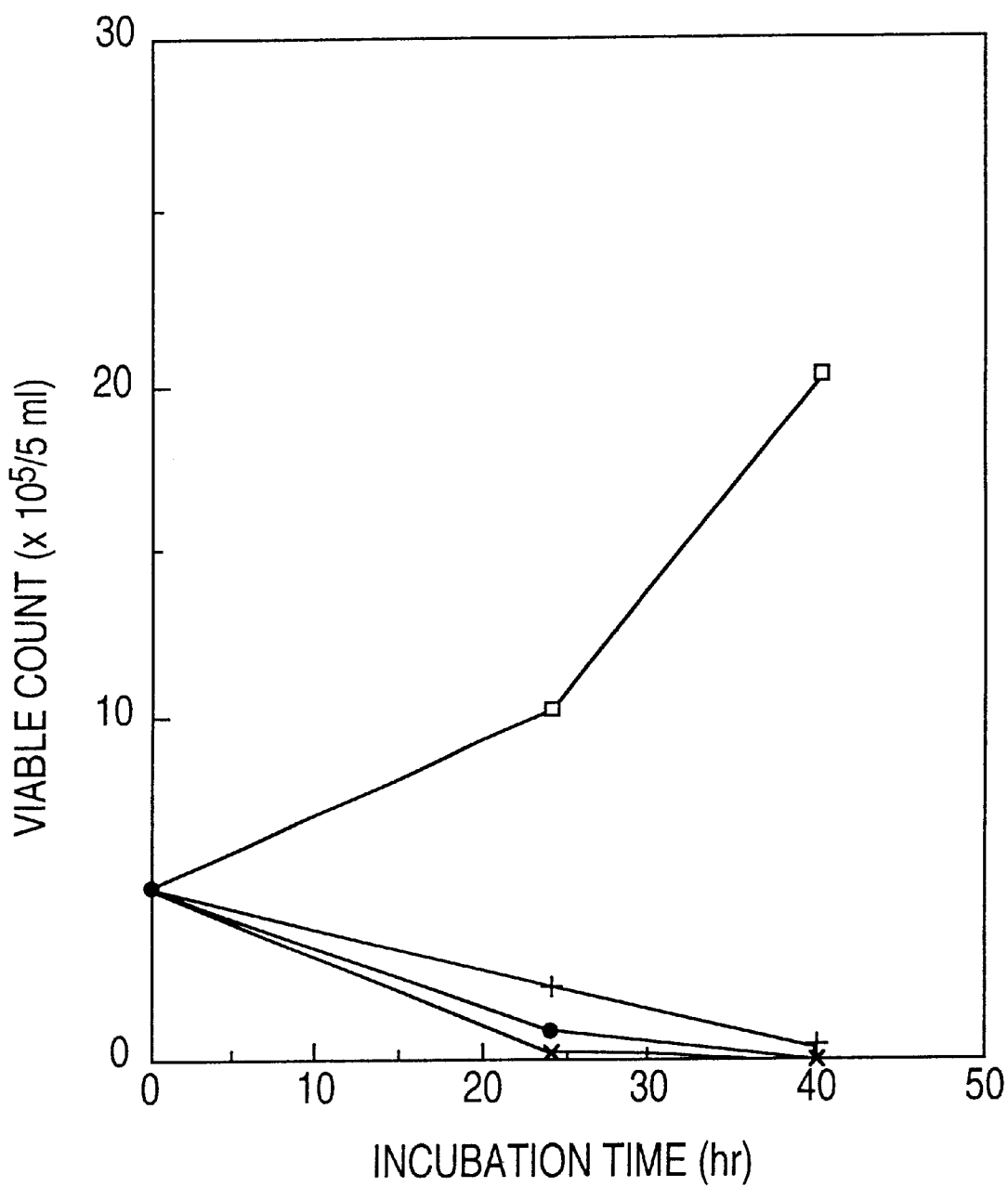
FIG. 27 shows the relationships between the incubation time and the viable count in the culture medium of HL-60 cells to which the sulfated-fucose-containing polysaccharides obtained in Examples 1, 15 and 18 have been added in such an amount as to give a concentration of 1 mg/ml.

The results are shown in FIG. 27 which is a graph showing relationships between the incubation time and the viable count in the culture medium of HL-60 cells to which the sulfated-fucose-containing polysaccharides obtained in Examples 1, 15 and 17 have been added in such an amount as to give a concentration of 1 mg/ml. In this figure, the abscissa refers to the incubation time (hr) while the ordinate refers to the viable count ($\times 10^5$ cells/5 ml) in the culture medium. In FIG. 27, the open square stands for the control (no addition), + stands for the sulfated-fucose-containing polysaccharide obtained in Example 1, the solid circle stands for that obtained in Example 15 and x stands for that obtained in Example 17.

In this case, dead cells showed the morphological characteristics of apoptosis such as shrinkage and fragmentation of the cells. Namely, these results indicate that the sulfated-fucose-containing polysaccharides obtained in Examples 1, 15 and 17 induce the apoptosis of the HL-60 cells and considerably inhibit the growth of these cells.

The sulfated-fucose-containing polysaccharides obtained in Examples 1, 15 and 17 were dissolved in a 30 mM Hepes buffer (pH 7.2) containing 120 mM of sodium chloride so as to give a concentration of 10 mg/ml and treated with a filter. Then the effect of these sulfated-fucose-containing polysaccharides of inducing apoptosis was examined in the same manner as the one described above. Thus the same results were obtained.

Example 22

Human acute lymphatic leukemia cells MOLT-3 (ATCC CRL-1552) were suspended in RPMI 1640 medium (mfd. by Gibco) containing 10% of fetal calf serum (mfd. by JRH Bioscience) treated at 56° C. for 30 minutes in such a manner as to give a concentration of $5 \times 10^5$ cells/9 ml. To five portions of 9 ml of this suspension were added 1 ml portions of 5 mg/ml solutions of the sulfated-fucose-containing polysaccharides obtained in Examples 1, 2, 12 and 16 in physiological saline which had been treated with a filter. After incubating at 37° C. for 60 hours in the presence of 5% of carbon dioxide, the cells were separated from the supernatant by centrifugation. Then the cells thus obtained were suspended in 20 $\mu$l of a 50 mM Tris hydrochloride buffer (pH 7.8) containing 10 mM of ethylenediaminetetraacetate and 0.5% of sodium lauroyl-sarcosinate. Then 1 $\mu$l of 10 mg/ml of Ribonuclease A (mfd. by Sigma) was added thereto and the mixture was treated at 50° C. for 30 minutes. After adding 1 $\mu$l of 10 mg/ml of Proteinase K, the mixture was treated at 50° C. for 1 hour. The cells thus treated were employed as a sample and electrophoresed in a 2% agarose gel under a constant voltage of 100 V. This gel was immersed in an ethidium bromide solution for 30 minutes and then the conditions of the DNA in the gel were examined by using a transilluminator. As a result, DNA ladders characteristic of apoptosis were observed therein. For the further confirmation, the above procedure was repeated using a 10 $\mu$g/ml solution of actinomycin D known as a reagent inducing apoptosis as a substitute for the above-mentioned sulfated-fucose-containing polysaccharides. As a result, DNA ladders were observed after incubating for 20 hours similar to the case of the sulfated-fucose-containing polysaccharides.

Based on these results, it has been clarified that the apoptosis of MOLT-3 cells can be induced by the sulfated-fucose-containing polysaccharides obtained in Examples 1, 2, 12 and 16.

The sulfated-fucose-containing polysaccharides obtained in Examples 1, 2, 12 and 16 were each dissolved in PBS prepared by dissolving 8 g of sodium chloride, 0.2 g of potassium chloride, 2.9 g of disodium hydrogen phosphate dodecahydrate and 0.2 g of potassium dihydrogen phosphate in 1 l of water so as to give a concentration of 5 mg/ml and treated in an autoclave at 121° C. for 20 minutes. Then the effects of these sulfated-fucose-containing polysaccharides of inducing apoptosis were examined in the same manner as the one described above. Thus the same results were obtained.

Example 23

Human acute lymphatic leukemia cells MOLT-3 (ATCC CRL-1552) were incubated at 37° C. in RPMI 1640 medium (mfd. by Gibco) containing 10% of fetal calf serum (mfd. by JRH Bioscience) treated at 56° C. for 30 minutes and then suspended in RPMI 1640 medium in such a manner as to give a concentration of $5 \times 10^3$ cells/ ml. Then the suspension was pipetted into a 24-well plate (mfd. by FALCON) at a ratio of 1.8 ml/well. To the suspension were added 0.2 ml portions of 0.5 mg/ml solutions of the sulfated-fucosecontaining polysaccharide mixture obtained in Example 1, the sulfated-fucose-containing polysaccharide-F obtained in Example 12, the sulfated-fucose-containing polysaccharides obtained in Examples 15 and dextran sulfate (molecular weight: 500,000; mfd. by Wako Pure Chemical Industries, Ltd.) each dissolved in PBS and sterilized followed by incubation at 37° C. in the presence of 5% of carbon dioxide. As a control, PBS alone was added in the same amount and incubation was effected in the same manner. 2, 4, 6 and 8 days after the initiation of the incubation, the cells were counted by the Trypan Blue staining method.

Figure 28:
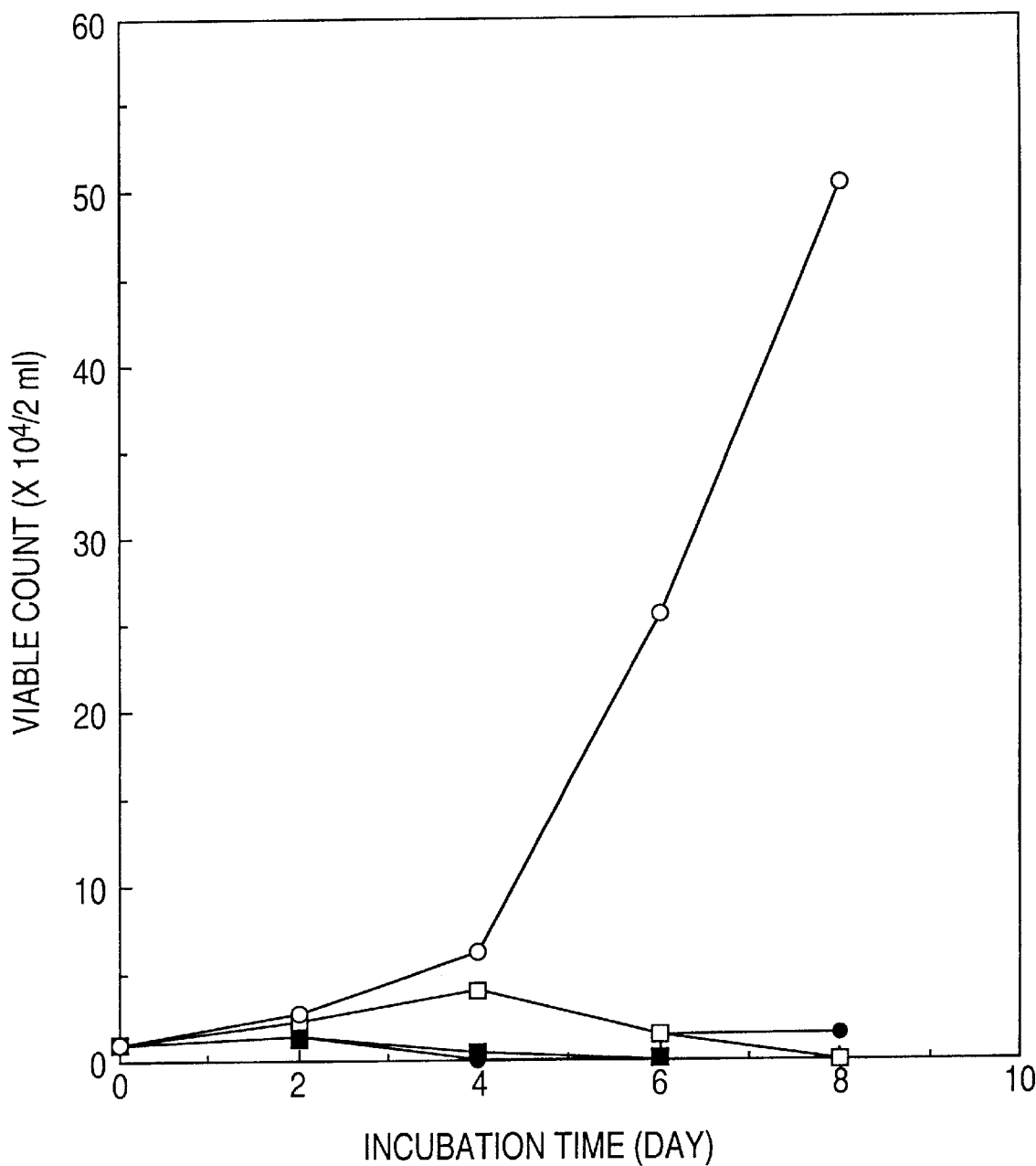
FIG. 28 shows the relationships between the incubation time and the viable count in the culture medium of MOLT-3 cells to which the sulfated-fucose-containing polysaccharides obtained in Example 1, the sulfated-fucose-containing polysaccharide-F obtained in Example 12 and the sulfated-fucose-containing polysaccharides obtained in Example 15 and dextran sulfate have been added.

The results are given in FIG. 28 which shows the relationships between the incubation time and the viable count in the culture medium of MOLT-3 cells to which the sulfated-fucose-containing polysaccharide obtained in Example 1, the sulfated-fucose-containing polysaccharide-F obtained in Example 12 and the sulfated-fucose-containing polysaccharides obtained in Examples 15 and dextran sulfate have been added so as to give a concentration of 0.5 mg/ml. In this figure, the abscissa refers to the incubation time (day) while the ordinate refers to the viable count ($\times 10^4$ cells/2 ml) in the culture medium. In FIG. 28, the open circle stands for the control (no addition), the solid circle stands for the sulfated-fucose-containing polysaccharide-F obtained in Example 12, the open square stands for the sulfated-fucose-containing polysaccharide obtained in Example 1and the solid square stands for that obtained in Example 15. Dextran sulfate shows substantially the same curve as the one obtained by using the sulfated-fucose-containing polysaccharide of Example 15.

In this case, dead cells showed the morphological characteristics of apoptosis such as shrinkage and fragmentation of the cells. Namely, these results indicate that the sulfated-fucose-containing polysaccharide obtained in Example 1, the sulfated-fucose-containing polysaccharide-F obtained in Example 12, the sulfated-fucose-containing polysaccharides obtained in Examples 15 and dextran sulfate induce the apoptosis of the MOLT-3 cells and considerably inhibit the growth of these cells.

The sulfated-fucose-containing polysaccharide obtained in Example 1, the sulfated-fucose-containing polysaccharide obtained in Example 15 and dextran sulfate (molecular weight: 500,000; mfd. by Wako Pure Chemical Industries, Ltd.) were each dissolved in PBS so as to give a concentration of 0.5 mg/ml and treated in an autoclave at 121° C. for 20 minutes. Then the effects thereof of inducing apoptosis were examined in the same manner as the one described above. Thus the same results were obtained.

Example 24

Human premyelocytic leukemia cells HL-60 (ATCC CCL-240) were incubated at 37° C. in RPMI 1640 medium (mfd. by Gibco) containing 10% of fetal calf serum (mfd. by JRH Bioscience) treated at 56° C. for 30 minutes and then suspended in ASF104 medium (mfd. by Ajinomoto Co., Ltd.) in such a manner as to give a concentration of $5\times 10^4$ cells/900 µl. To nine portions of 900 µl of this suspension were respectively added 100 µl portions of physiological saline and 10 mg/ml solutions of the sulfated-fucose-containing polysaccharide preparation obtained in Example 1, F-Fd-1 to F-Fd-4 and three sulfated-fucose-containing polysaccharides obtained in Example 13 in physiological saline which had been treated with a filter. After incubating at 37° C. in the presence of 5% of carbon dioxide for 40 hours, the cells were observed under a microscope to thereby examine the degree of growth and the morphology of the cells.

As a result, the HL-60 cells to which the sulfated-fucose-containing polysaccharide preparation, F-Fd-1 to F-Fd-4 and three sulfated-fucose-containing polysaccharides were added all showed characteristics of apoptosis such as the shrinkage and fragmentation of the cells. The HL-60 cells to which physiological saline was added showed an increase in cell count of about 4 times, while those to which the sulfated-fucose-containing polysaccharide preparation, F-Fd-1 to F-Fd-4 and three sulfated-fucose-containing polysaccharides were added showed no increase therein or a decrease to a level less than $\frac{1}{10}$. These results indicate that the growth of the HL-60 cells were inhibited due to the apoptosis-inducing effects of the sulfated-fucose-containing polysaccharide preparation, F-Fd-1 to F-Fd-4 and three sulfated-fucose-containing polysaccharides.

For the further confirmation, the above procedure was repeated using a 10 µg/ml solution of actinomycin D known as a reagent inducing apoptosis as a substitute for the above-mentioned sulfated-fucose-containing polysaccharides. As a result, the shrinkage and fragmentation of the cells were observed after incubating for 20 hours similar to the case of the sulfated-fucose-containing polysaccharides. Based on these results, it has been clarified that the apoptosis of HL-60 cells can be induced by the sulfated-fucose-containing polysaccharide preparation obtained in Example 1, F-Fd-1 to F-Fd-4 and three sulfated-fucose-containing polysaccharides obtained in Example 13.

The sulfated-fucose-containing polysaccharide preparation obtained in Example 1, F-Fd-1 to F-Fd-4 and three sulfated-fucose-containing polysaccharides obtained in Example 13 were each dissolved in a 30 mM Hepes buffer (pH 7) containing 120 mM of sodium chloride so as to give a concentration of 10 mg/ml and treated in an autoclave at 121° C. for 20 minutes. Then the effects thereof of inducing apoptosis were examined in the same manner as the one described above. Thus the same results were obtained.

Example 25

Pulmonary cancer cells A-549 (ATCC CCL-185), SV40-transformed plumonary cells WI-38VA13 (ATCC CCL-75.1) and hepatic caner cells Hep G2 (ATCC HB-8065) were each suspended in RPMI 1640 medium (mfd. by Gibco) containing 10% of fetal calf serum (mfd. by JRH Bioscience) treated at 56° C. for 30 minutes in such a manner as to give a concentration of $10^4$ cells/1.8 ml. To 1.8 ml portions of the suspension of each cell line were added 200 µl portions of physiological saline and 1 mg/ml solutions of the sulfated-fucose-containing polysaccharides obtained in Examples 1 and 15 and six sulfated-fucose-containing oligosaccharides obtained in Example 14 in physiological saline which had been treated with a filter. After incubating at 37° C. in the presence of 5% of carbon dioxide for 6 days, the cells were observed under a microscope to thereby examine the degree of growth and the morphology of the cells.

As a result, the plumonary cancer cells A-549, the SV40-transformed plumonary cells WI-38VA13 and the hepatic cancer cells Hep G2 to which the sulfated-fucose-containing polysaccharides of Examples 1 and 15 and three fractions of 2,000 or more in molecular weight among the six sulfated-fucose-containing oligosaccharides obtained in Example 14 were added all showed characteristics of apoptosis such as the shrinkage and fragmentation of the cells. The cancer cell lines to which physiological saline was added showed a remarkable increase in cell count, while those to which the sulfated-fucose-containing polysaccharides of Examples 1 and 15 and three fractions of 2,000 or more in molecular weight among the six sulfated-fucose-containing oligosaccharides obtained in Example 14 were added showed each a decrease in cell count. These results indicate that the growth of each of the cancer cell lines was inhibited due to the apoptosis-inducing effects of these sulfated-fucose-containing polysaccharides and oligosaccharides.

The sulfated-fucose-containing polysaccharides obtained in Examples 1 and 15 and six sulfated-fucose-containing oligosaccharides obtained in Example 14 were each dissolved in PBS so as to give a concentration of 1 mg/ml and treated in an autoclave at 121° C. for 20 minutes. Then the effects thereof of inducing apoptosis were examined in the same manner as the one described above. Thus the same results were obtained.

Example 26

Colonic cancer cells HCT 116 (ATCC CCL-247) and gastric cancer cells AGS (ATCC CCL-1739) were each suspended in McCoy's 5a medium (mfd. by Gibco) and Ham's F12 medium (mfd. by Gibco) containing 10% of fetal calf serum (mfd. by JRH Bioscience) treated at 56° C. for 30 minutes in such a manner as to give a concentration of $10^4$ cells/1.8 ml. To 1.8 ml portions of the suspension of each cell line were added 200 $\mu$l portions of physiological saline and 10 mg/ml solutions of the sulfated-fucose-containing polysaccharides obtained in Examples 1, 12 and 15 and four sulfated-fucose-containing oligosaccharides F-Fd-1 to F-Fd-4 in physiological saline which had been treated with a filter. After incubating at 37° C. in the presence of 5% of carbon dioxide for 48 hours, the cells were observed under a microscope to thereby examine the degree of growth and the morphology of the cells.

As a result, the colonic cancer cells HCT 116 and the gastric cancer cells AGS to which the sulfated-fucose-containing polysaccharides obtained in Examples 1, 12 and 15 and four sulfated-fucose-containing oligosaccharides F-Fd-1 to F-Fd-4 were added all showed characteristics of apoptosis such as the shrinkage and fragmentation of the cells. The cancer cell lines to which physiological saline was added showed a remarkable increase in cell count, while those to which the sulfated-fucose-containing polysaccharides of Examples 1, 12 and 15 and four sulfated-fucose-containing oligosaccharides F-Fd-1 to F-Fd-4 were added showed each a decrease in cell count. These results indicate that the growth of each of the cancer cell lines was inhibited due to the apoptosis-inducing effects of these sulfated-fucose-containing polysaccharides and oligosaccharides.

The sulfated-fucose-containing polysaccharides obtained in Examples 1, 12 and 15 and four sulfated-fucose-containing oligosaccharides F-Fd-1 to F-Fd-3 were each dissolved in PBS so as to give a concentration of 10 mg/ml and treated in an autoclave at 121° C. for 20 minutes. Then the effects thereof of inducing apoptosis were examined in the same manner as the one described above. Thus the same results were obtained.

Example 27

Human colonic cancer cells HCT 116 were incubated at 37° C. in McCoy's 5a medium (mfd. by Gibco) containing 10% of fetal calf serum (mfd. by JRH Bioscience) treated at 56° C. for 30 minutes and then suspended in McCoy's 5 medium in such a manner as to give a concentration of $5\times10^3$ cells/ ml. Then the suspension was pipetted into a 24-well plate (mfd. by FALCON) at a ratio of 1.8 ml/well. To the suspension were added 0.2 ml portions of 10 mg/ml solutions of the sulfated-fucose-containing polysaccharide preparation and the sulfated-fucose-containing polysaccharide mixture obtained in Example 1, the sulfated-fucose-containing polysaccharide-F and the sulfated-fucose-containing polysaccharide-U obtained in Example 12, F-Fd-1, F-Fd-2, F-Fd-3 and F-Fd-4, and the sulfated-fucose-containing polysaccharide obtained in Example 15 dissolved in PBS and 5 mg/ml solutions of heparin (mfd. by Wako Pure Chemical Industries, Ltd.) and dextran sulfate (molecular weight: 500,000, mfd. by Wako Pure Chemical Industries, Ltd.) having been treated in an autoclave at 121° C. for 20 minutes followed by incubation at 37° C. in the presence of 5% of carbon dioxide. As a control, PBS alone was added in the same amount and incubation was effected in the same manner. 1, 2, 3 and 4 days after the initiation of the incubation, the viable cells were counted in accordance with the method described in "Soshiki Baiyo no Gijutsu" (second ed.), Asakura Shuppan, ed. by Nippon Soshiki Baiyo Gakkai, 26–28 (1990), namely, by the Trypan Blue staining method on a counting chamber.

Figure 29:
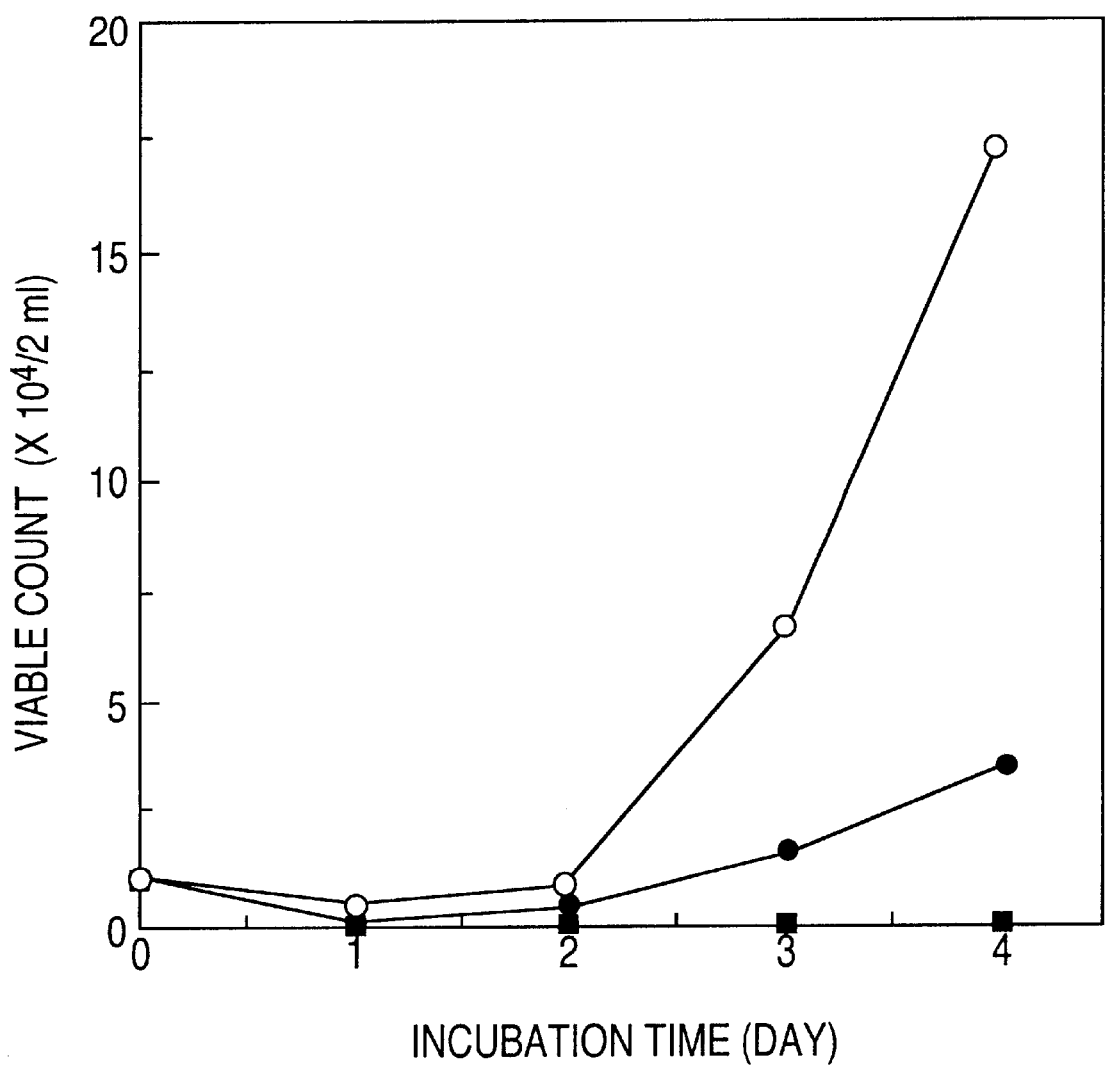
FIG. 29 shows the relationships between the incubation time and the viable count in the culture medium of HCT 116 cells to which the sulfated-fucose-containing polysaccharide-containing preparation obtained in Example 1, the sulfated-fucose-containing polysaccharide mixture obtained in Example 1, the sulfated-fucose-containing polysaccharide-U and sulfated-fucose-containing polysaccharide-F, F-Fd-1, F-Fd-2, F-Fd-3 and F-Fd-4 obtained in Example 12, the sulfated-fucose-containing polysaccharides obtained in Example 15 and heparin dextran sulfate have been added.

The results are given in FIG. 29 which shows the relationships between the incubation time and the viable count in the culture medium of HCT 116 cells to which the sulfated-fucose-containing polysaccharide preparation obtained in Example 1, the sulfated-fucose-containing polysaccharide mixture obtained in Example 1, the sulfated-fucose-containing polysaccharide-U and sulfated-fucose-containing polysaccharide-F obtained in Example 12, F-Fd-1, F-Fd-2, F-Fd-3 and F-Fd-4, and the sulfated-fucose-containing polysaccharide obtained in Example 15 each in a concentration of 1 mg/ml and heparin and dextran sulfate each in a concentration of 0.5 mg/ml have been added. In this figure, the abscissa refers to the incubation time (day) while the ordinate refers to the viable count ($\times10^4$ cells/2 ml) in the culture medium. In FIG. 29, the open circle stands for the control (no addition), the solid circle stands for the sulfated-fucose-containing polysaccharide preparation obtained in Example 1 and the solid square stands for the sulfated-fucose-containing polysaccharide mixture obtained in Example 1. The sulfated-fucose-containing polysaccharide-U and sulfated-fucose-containing polysaccharide-F obtained in Example 12, F-Fd-1, F-Fd-2, F-Fd-3 and F-Fd-4, and the sulfated-fucose-containing polysaccharide obtained in Example 15 show each substantially the same curve as the one of the sulfated-fucose-containing polysaccharide mixture of Example 1. On the other hand, heparin and dextran sulfate show each substantially the same curve as the one of the sulfated-fucose-containing polysaccharide preparation of Example 1.

As a result, the HCT 116 cells to which PBS was added showed a remarkable increase in cell count, while those to which the sulfated-fucose-containing polysaccharide preparation of Example 1, the sulfated-fucose-containing polysaccharide mixture of Example 1, the sulfated-fucose-containing polysaccharide-F and sulfated-fucose-containing polysaccharide-U of Example 12, F-Fd-1, F-Fd-2, F-Fd-3 and F-Fd-4, heparin, and dextran sulfate were added showed each little increase or a decrease in cell count.

The HCT 116 cells to which the sulfated-fucose-containing polysaccharide preparation of Example 1, the sulfated-fucose-containing polysaccharide mixture of Example 1, the sulfated-fucose-containing polysaccharide-F and sulfated-fucose-containing polysaccharide-U of Example 12, F-Fd-1, F-Fd-2, F-Fd-3 and F-Fd-4, the sulfated-fucose-containing polysaccharide of Example 15, heparin and dextran sulfate were added all showed characteristics of apoptosis such as the shrinkage and fragmentation of the cells.

Namely, it has been found out that the growth of the HCT 116 cells is inhibited due to the apoptosis inducing effects of these sulfated-fucose-containing polysaccharides and oligosaccharides, heparin and dextran sulfate.

The sulfated-fucose-containing polysaccharide preparation and sulfated-fucose-containing polysaccharide mixture obtained in Example 1, sulfated-fucose-containing polysaccharide-F and sulfated-fucose-containing polysaccharide-U obtained in Example 12, F-Fd-1, F-Fd-2, F-Fd-3 and F-Fd-4, and the sulfated-fucose-containing polysaccharide obtained in Example 15 were each dissolved in PBS so as to give a concentration of 10 mg/ml. Heparin and dextran sulfate were each dissolved in PBS so as to give a concentration of 5 mg/ml. These solutions were all treated with a filter and then the effects thereof of inducing apoptosis were examined in the same manner as the one described above. Thus the same results were obtained.

Example 28

Human colonic cancer cells HCT 116 were incubated at 37° C. in McCoy's 5a medium (mfd. by Gibco) containing 10% of fetal calf serum (mfd. by JRH Bioscience) treated at 56° C. for 30 minutes and then suspended in McCoy's 5a medium in such a manner as to give a concentration of $5\times10^3$ cells/ ml. Then the suspension was pipetted into a 24-well plate (mfd. by FALCON) at a ratio of 1.8 ml/well. To the suspension were added 0.2 ml portions of 20 mg/ml, 30 mg/ml and 50 mg/ml solutions of the sulfated-fucose-containing polysaccharide preparation obtained in Example 1 in PBS which had been treated in an autoclave at 121° C. for 20 minutes followed by incubation at 37° C. in the presence of 5% of carbon dioxide. As a control, PBS alone was added in the same amount and incubation was effected in the same manner. After the initiation of the incubation, the viable cells were counted with the passage of time in accordance with the method described in "Soshiki Baiyo no Gijutsu" (second ed.), Asakura Shuppan, ed. by Nippon Soshiki Baiyo Gakkai, 26–28 (1990), namely, by the Trypan Blue staining method on a counting chamber.

Figure 30:
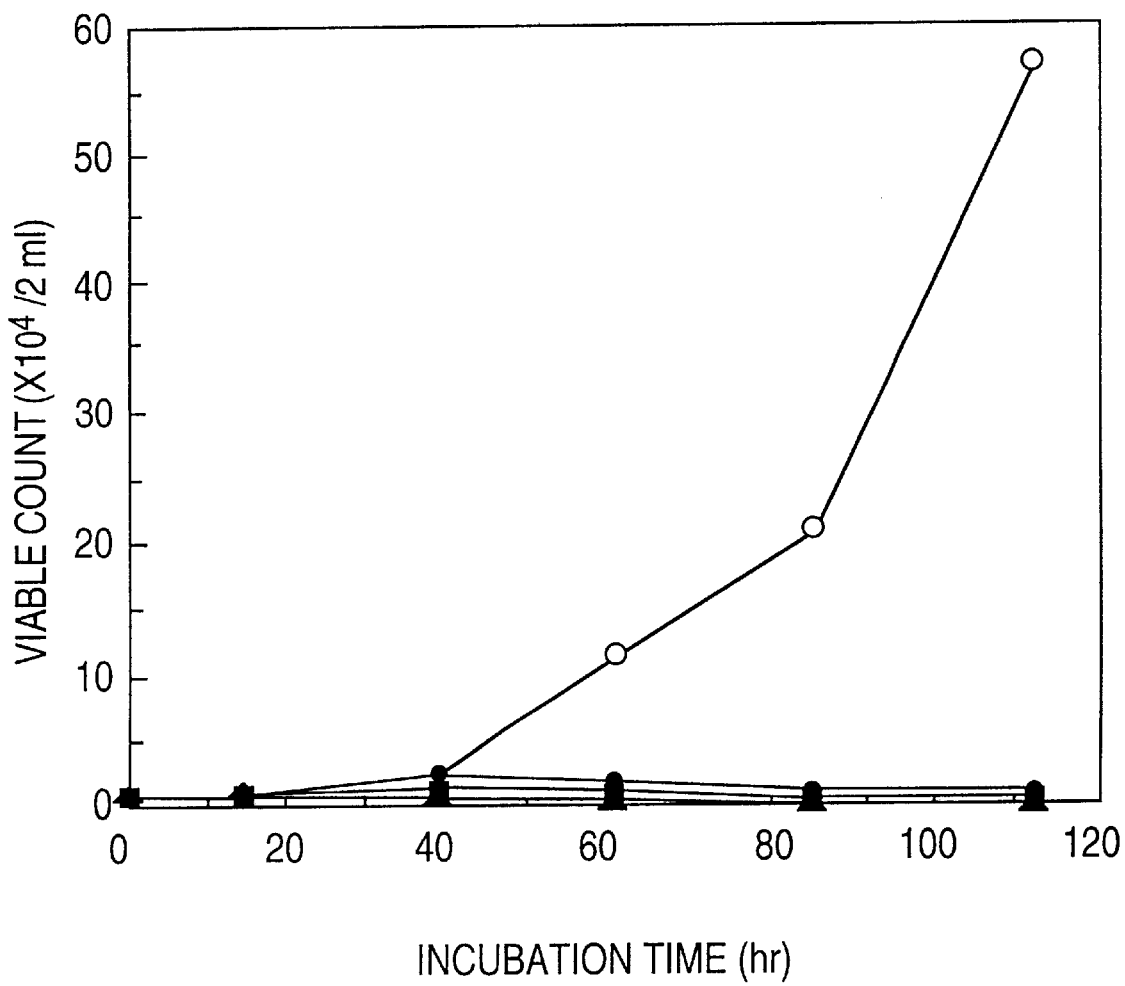
FIG. 30 shows the relationships between the incubation time and the viable count in the culture medium of HCT 116 cells to which the sulfated-fucose-containing polysaccharide preparation obtained in Example 1 has been added at various concentrations.

The results are given in FIG. 30 which shows the relationships between the incubation time and the viable count in the culture medium of HCT 116 cells to which the sulfated-fucose-containing polysaccharide preparation obtained in Example 1 has been added at various concentrations. In this figure, the abscissa refers to the incubation time (hr) while the ordinate refers to the viable count ($\times10^4$ cells/2 ml) in the culture medium. In FIG. 30, the open circle stands for the control (no addition), the solid circle stands for the addition of 2 mg/ml of the sulfated-fucose-containing polysaccharide preparation, the solid square stands for that of 3 mg/ml thereof and the solid triangle stands for that of 5 mg/ml thereof.

As a result, the HCT 116 cells to which PBS was added showed a remarkable increase in cell count, while those to which the sulfated-fucose-containing polysaccharide preparation of Example 1 was added showed each a decrease in cell count.

The HCT 116 cells to which the sulfated-fucose-containing polysaccharide preparation of Example 1 was added all showed characteristics of apoptosis such as the shrinkage and fragmentation of the cells.

Namely, it has been found out that the sulfated-fucose-containing polysaccharide preparation obtained in Example 1 has the effect of inducing apoptosis on the HCT 116 cells at least at a concentration of 2 mg/ml and thus inhibits the growth of the cells.

The sulfated-fucose-containing polysaccharide preparation obtained in Example 1 was dissolved in PBS so as to give concentrations of 20 mg/ml, 30 mg/ml and 50 mg/ml and treated with a filter. Then the effects thereof of inducing apoptosis were examined in the same manner as the one described above. Thus the same results were obtained.

Example 29

Human gastric cancer cells AGS were incubated at 37° C. in Ham's F12 medium (mfd. by Gibco) containing 10% of fetal calf serum (mfd. by JRH Bioscience) treated at 56° C. for 30 minutes and then suspended in Ham's F12 medium in such a manner as to give a concentration of $5\times10^3$ cells/ ml. Then the suspension was pipetted into a 24-well plate (mfd. by FALCON) at a ratio of 1.8 ml/well. To the suspension were added 0.2 ml portions of 20 mg/ml, 30 mg/ml and 50 mg/ml solutions of the sulfated-fucose-containing polysaccharide preparation obtained in Example 1 in PBS which had been treated in an autoclave at 121° C. for 20 minutes followed by incubation at 37° C. in the presence of 5% of carbon dioxide. As a control, PBS alone was added in the same amount and incubation was effected in the same manner. After the initiation of the incubation, the viable cells were counted with the passage of time in accordance with the method described in "Soshiki Baiyo no Gijutsu" (second ed.), Asakura Shuppan, ed. by Nippon Soshiki Baiyo Gakkai, 26–28 (1990), namely, by the Trypan Blue staining method on a counting chamber.

Figure 31:
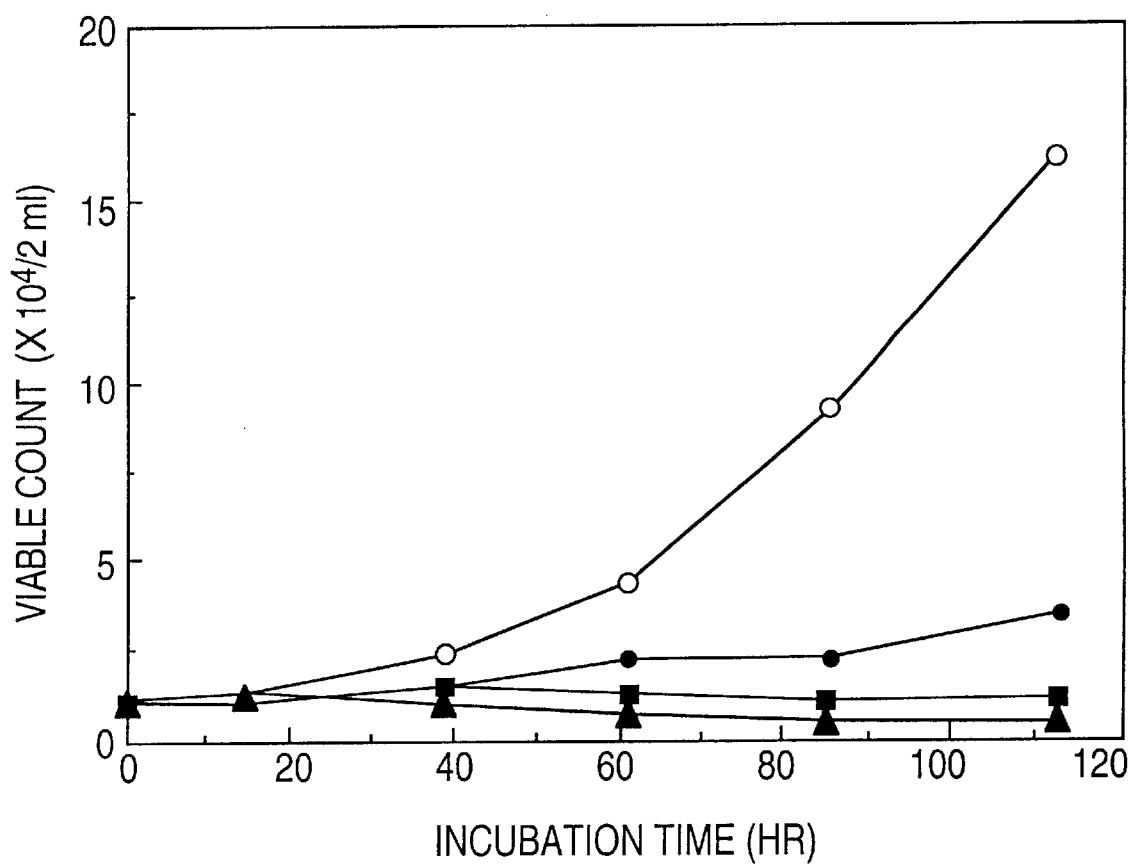
FIG. 31 shows the relationships between the incubation time and the viable count in the culture medium of AGS cells to which the sulfated-fucose-containing polysaccharide preparation obtained in Example 1 has been added at various concentrations.

The results are given in FIG. 31 which shows the relationships between the incubation time and the viable count in the culture medium of AGS cells to which the sulfated-fucose-containing polysaccharide preparation obtained in Example 1 has been added at various concentrations. In this figure, the abscissa refers to the incubation time (hr) while the ordinate refers to the viable count ($\times10^4$ cells/2 ml) in the culture medium. In FIG. 31, the open circle stands for the control (no addition), the solid circle stands for the addition of 2 mg/ml of the sulfated-fucose-containing polysaccharide preparation, the solid square stands for that of 3 mg/ml thereof and the solid triangle for that of 5 mg/ml thereof.

As a result, the AGS cells to which PBS was added showed a remarkable increase in cell count, while those to which the sulfated-fucose-containing polysaccharide preparation of Example 1 was added at a final concentration of 3 mg/ml or more showed a remarkable decrease therein and the growth of the cells to which 2 mg/ml of the sulfated-fucose-containing polysaccharide preparation of Example 1 was largely inhibited.

The AGS cells to which the sulfated-fucose-containing polysaccharide preparation of Example 1 was added showed characteristics of apoptosis such as the shrinkage and fragmentation of the cells.

Namely, it has been found out that the sulfated-fucose-containing polysaccharide preparation obtained in Example 1 has the effect of inducing apoptosis on the AGS cells at least at a concentration of 2 mg/ml and thus inhibits the growth of the cells.

The sulfated-fucose-containing polysaccharide preparation obtained in Example 1 was dissolved in PBS so as to give concentrations of 20 mg/ml, 30 mg/ml and 50 mg/ml and treated with a filter. Then the effects thereof of inducing apoptosis were examined in the same manner as the one described above. Thus the same results were obtained.

Example 30

Human colonic cancer cells SW480 (ATCC CCL-228) were incubated at 37° C. in L-15 medium (mfd. by Gibco)

containing 10% of fetal calf serum (mfd. by JRH Bioscience) treated at 56° C. for 30 minutes and then suspended in L-15 medium in such a manner as to give a concentration of 5×10³ cells/ ml. Then the suspension was pipetted into a 24-well plate (mfd. by FALCON) at a ratio of 1.8 ml/well. To the suspension were added 0.2 ml portions of 10 mg/ml, 30 mg/ml and 50 mg/ml solutions of the sulfated-fucose-containing polysaccharide preparation obtained in Example 1 in PBS which had been treated in an autoclave at 121° C. for 20 minutes followed by incubation at 37° C. in the presence of 5% of carbon dioxide. As a control, PBS alone was added in the same amount and incubation was effected in the same manner. After the initiation of the incubation, the viable cells were counted with the passage of time in accordance with the method described in "Soshiki Baiyo no Gijutsu" (second ed.), Asakura Shuppan, ed. by Nippon Soshiki Baiyo Gakkai, 26–28 (1990), namely, by the Trypan Blue staining method on a counting chamber.

Figure 32:
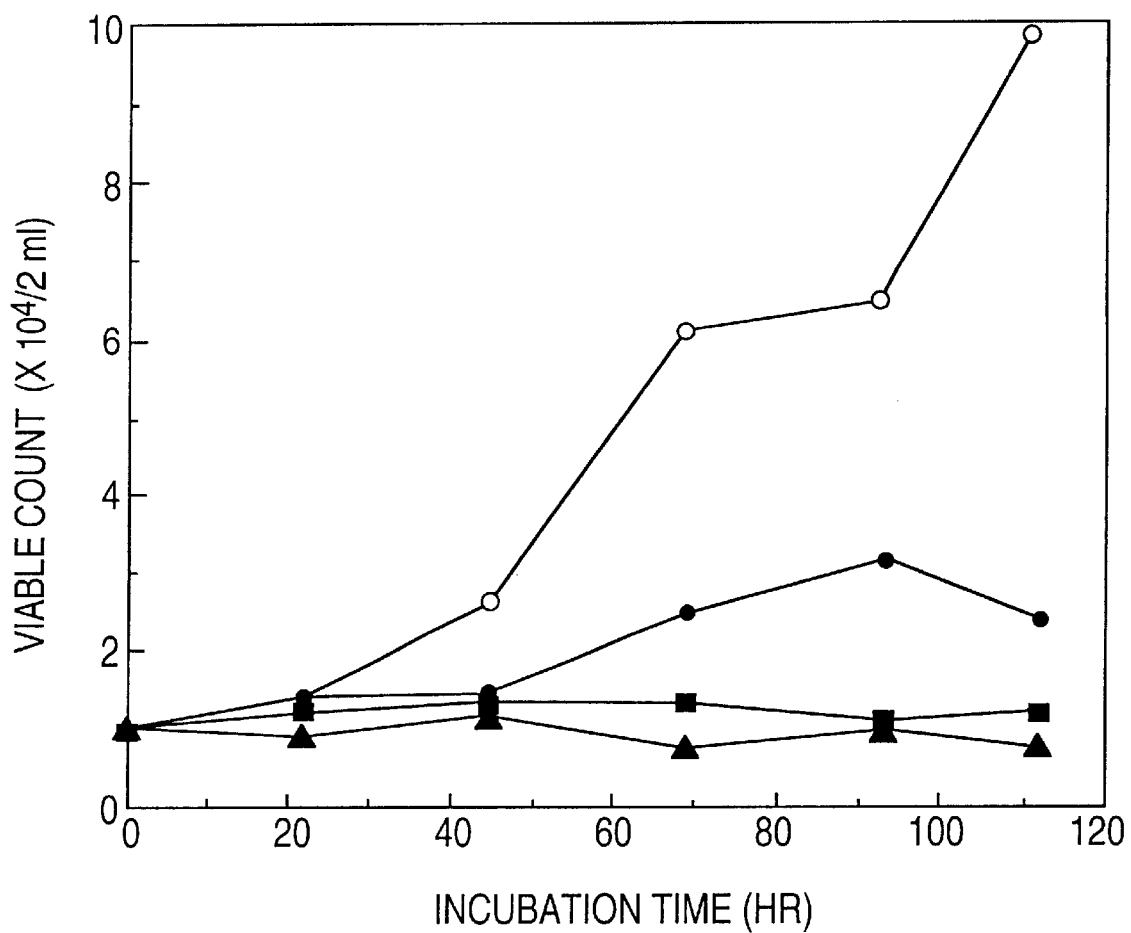
FIG. 32 shows the relationships between the incubation time and the viable count in the culture medium of SW 480 cells to which the sulfated-fucose-containing polysaccharide preparation obtained in Example 1 has been added at various concentrations.

The results are given in FIG. 32 which shows the relationships between the incubation time and the viable count in the culture medium of SW480 cells to which the sulfated-fucose-containing polysaccharide preparation obtained in Example 1 has been added at various concentrations. In this figure, the abscissa refers to the incubation time (hr) while the ordinate refers to the viable count (×10⁴ cells/2 ml) in the culture medium. In FIG. 32, the open circle stands for the control (no addition), the solid circle stands for the addition of 1 mg/ml of the sulfated-fucose-containing polysaccharide preparation, the solid square stands for that of 3 mg/ml thereof and the solid triangle stands for that of 5 mg/ml thereof.

As a result, the SW480 cells to which PBS was added showed a remarkable increase in cell count, while those to which the sulfated-fucose-containing polysaccharide preparation of Example 1 was added at a final concentration of 3 mg/ml or more showed a remarkable decrease therein and the growth of the cells to which 1 mg/ml of the sulfated-fucose-containing polysaccharide preparation of Example 1 was largely inhibited.

The SW480 cells to which the sulfated-fucose-containing polysaccharide preparation of Example 1 was added showed characteristics of apoptosis such as the shrinkage and fragmentation of the cells.

Namely, it has been found out that the sulfated-fucose-containing polysaccharide preparation obtained in Example 1 has the effect of inducing apoptosis on the SW480 cells at least a concentration of 1 mg/ml and thus inhibits the growth of the cells.

The sulfated-fucose-containing polysaccharide preparation obtained in Example 1 was dissolved in PBS so as to give concentrations of 10 mg/ml, 30 mg/ml and 50 mg/ml and treated with a filter. Then the effects thereof of inducing apoptosis were examined in the same manner as the one described above. Thus the same results were obtained.

Example 31

Human colonic cancer cells WiDr (ATCC CCL-218) were incubated at 37° C. in DMEM medium (mfd. by Dainippon Pharmaceutical Co., Ltd.) containing 10% of fetal calf serum (mfd. by JRH Bioscience) and 1% of NEAA (mfd. by Dainippon Pharmaceutical Co., Ltd.) treated at 56° C. for 30 minutes and then suspended in the above-mentioned medium in such a manner as to give a concentration of 5×10³ cells/ ml. Then the suspension was pipetted into a 24-well plate (mfd. by FALCON) at a ratio of 1.8 ml/well.

To the suspension were added 0.2 ml portions of 10 mg/ml solutions of the sulfated-fucose-containing polysaccharide mixture obtained in Example 1, the sulfated-fucose-containing polysaccharide-F obtained in Example 12, F-Fd-3 and F-Fd-4, and the sulfated-fucose-containing polysaccharide obtained in Example 15 dissolved in PBS and treated in an autoclave at 121° C. for 20 minutes followed by incubation at 37° C. in the presence of 5% of carbon dioxide. As a control, PBS alone was added in the same amount and incubation was effected in the same manner. After the initiation of the incubation, the viable cells were counted with the passage of time in accordance with the method described in "Soshiki Baiyo no Gijutsu" (second ed.), Asakura Shuppan, ed. by Nippon Soshiki Baiyo Gakkai, 26–28 (1990), namely, by the Trypan Blue staining method on a counting chamber.

Figure 33:
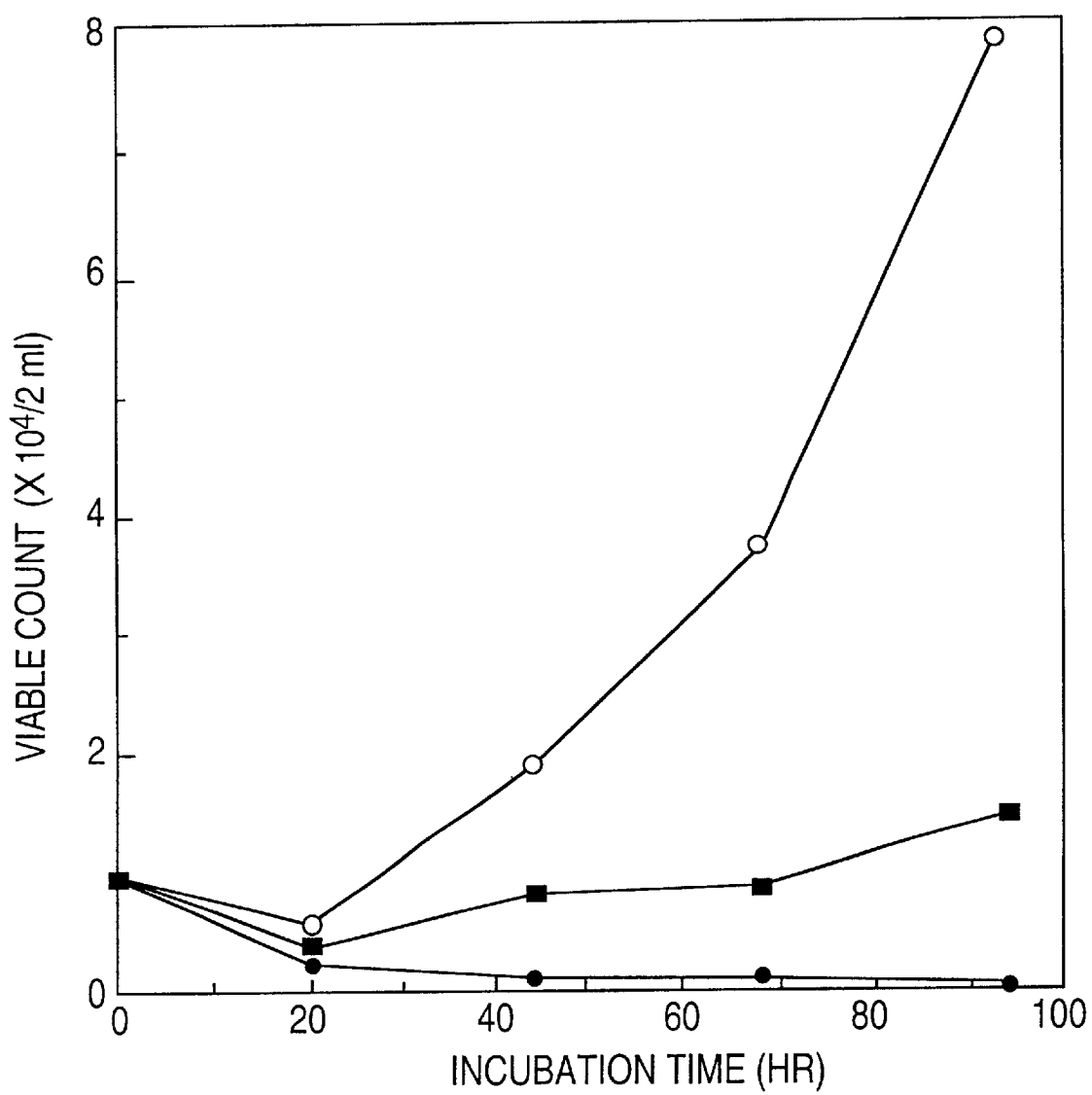
FIG. 33 shows the relationships between the incubation time and the viable count in the culture medium of WiDr cells to which the sulfated-fucose-containing polysaccharide preparation obtained in Example 1, the sulfated-fucose-containing polysaccharide-F, F-Fd-3 and F-Fd-4 obtained in Example 12 and the sulfated-fucose-containing polysaccharides obtained in Example 15 have been added.

The results are given in FIG. 33 which shows the relationships between the incubation time and the viable count in the culture medium of WiDr cells to which the sulfated-fucose-containing polysaccharide mixture obtained in Example 1, the sulfated-fucose-containing polysaccharide-F obtained in Example 12, F-Fd-3 and F-Fd-4, and the sulfated-fucose-containing polysaccharide obtained in Example 15 have been added so as to give each a concentration of 1 mg/ml. In this figure, the abscissa refers to the incubation time (hr) while the ordinate refers to the viable count (×10⁴ cells/2 ml) in the culture medium. In FIG. 33, the open circle stands for the control (no addition), the solid square stands for the sulfated-fucose-containing polysaccharide-F obtained in Example 12 and the solid circle stands for the sulfated-fucose-containing polysaccharide obtained in Example 15. F-Fd-3 and F-Fd-4 show each substantially the same curve as the one of the sulfated-fucose-containing polysaccharide obtained in Example 15.

As a result, the WiDr cells to which PBS was added showed a remarkable increase in cell count, while those to which the sulfated-fucose-containing polysaccharide mixture of Example 1, the sulfated-fucose-containing polysaccharide-F of Example 12, F-Fd-3 and F-Fd-4, and the sulfated-fucose-containing polysaccharide obtained in Example 15 were added showed each a decrease in cell count.

The WiDr cells to which the sulfated-fucose-containing polysaccharide mixture of Example 1, the sulfated-fucose-containing polysaccharide-F of Example 12, F-Fd-3 and F-Fd-4, and the sulfated-fucose-containing polysaccharide of Example 15 were added all showed characteristics of apoptosis such as the shrinkage and fragmentation of the cells.

Namely, it has been found out that the sulfated-fucose-containing polysaccharide mixture obtained in Example 1, the sulfated-fucose-containing polysaccharide-F of Example 12, F-Fd-3 and F-Fd-4, and the sulfated-fucose-containing polysaccharide of Example 15 have the effects of inducing apoptosis on the WiDr cells and thus can inhibit the growth of the cells.

The sulfated-fucose-containing polysaccharide mixture obtained in Example 1, the sulfated-fucose-containing polysaccharide-F obtained in Example 12, F-Fd-3 and F-Fd-4, and the sulfated-fucose-containing polysaccharide obtained in Example 15 were each dissolved in PBS so as to give a concentration of 10 mg/ml and treated with a filter. Then the effects thereof of inducing apoptosis were examined in the same manner as the one described above. Thus the same results were obtained.

Example 32

Human colonic cancer cells WiDr (ATCC CCL-218) were incubated at 37° C. in DMEM medium (mfd. by Dainippon Pharmaceutical Co., Ltd.) containing 10% of fetal calf serum (mfd. by JRH Bioscience) and 1% of NEAA (mfd. by Dainippon Pharmaceutical Co., Ltd.) treated at 56° C. for 30 minutes and then suspended in the above-mentioned medium in such a manner as to give a concentration of $5 \times 10^3$ cells/ml. Then the suspension was pipetted into a 24-well plate (mfd. by FALCON) at a ratio of 1.8 ml/well. To the suspension were added 0.2 ml portions of 10 mg/ml, 30 mg/ml and 50 mg/ml solutions of the sulfated-fucose-containing polysaccharide preparation obtained in Example 1 in PBS which had been treated in an autoclave at 121° C. for 20 minutes followed by incubation at 37° C. in the presence of 5% of carbon dioxide. As a control, PBS alone was added in the same amount and incubation was effected in the same manner. After the initiation of the incubation, the viable cells were counted with the passage of time in accordance with the method described in "Soshiki Baiyo no Gijutsu" (second ed.), Asakura Shuppan, ed. by Nippon Soshiki Baiyo Gakkai, 26–28 (1990), namely, by the Trypan Blue staining method on a counting chamber.

Figure 34:
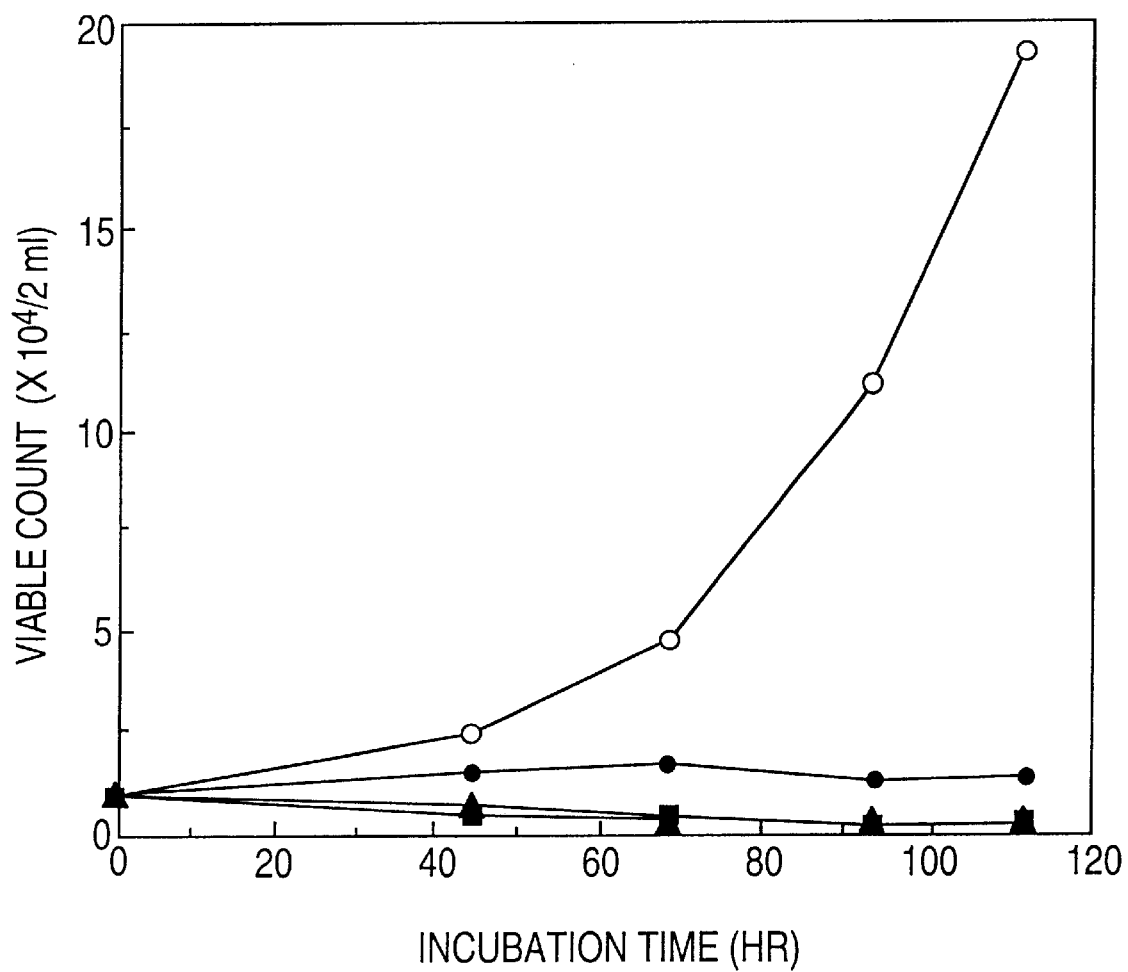
FIG. 34 shows the relationships between the incubation time and the viable count in the culture medium of WiDr cells to which the sulfated-fucose-containing polysaccharide preparation obtained in Example 1 has been added at various concentrations.

The results are given in FIG. 34 which shows the relationships between the incubation time and the viable count in the culture medium of WiDr cells to which the sulfated-fucose-containing polysaccharide preparation obtained in Example 1 has been added at various concentrations. In this figure, the abscissa refers to the incubation time (hr) while the ordinate refers to the viable count ($\times 10^4$ cells/2 ml) in the culture medium. In FIG. 34, the open circle stands for the control (no addition), the solid circle stands for the addition of 1 mg/ml of the sulfated-fucose-containing polysaccharide preparation, the solid square stands for that of 3 mg/ml thereof and the solid triangle stands for that of 5 mg/ml thereof.

As a result, the WiDr cells to which PBS was added showed a remarkable increase in cell count, while those to which the sulfated-fucose-containing polysaccharide preparation of Example 1 was added at a final concentration of 3 mg/ml or more showed a remarkable decrease therein and the growth of the cells to which 1 mg/ml of the sulfated-fucose-containing polysaccharide preparation of Example 1 was largely inhibited.

The WiDr cells to which the sulfated-fucose-containing polysaccharide preparation of Example 1 was added showed characteristics of apoptosis such as the shrinkage and fragmentation of the cells.

Namely, it has been found out that the sulfated-fucose-containing polysaccharide preparation obtained in Example 1 has the effect of inducing apoptosis on the WiDr cells at least at a concentration of 1 mg/ml and thus inhibits the growth of the cells.

The sulfated-fucose-containing polysaccharide preparation obtained in Example 1 was dissolved in PBS so as to give concentrations of 10 mg/ml, 30 mg/ml and 50 mg/ml and treated with a filter. Then the effects thereof of inducing apoptosis were examined in the same manner as the one described above. Thus the same results were obtained.

Example 33

Human premyelocytic leukemia cells HL-60 (ATCC CCL-240) were incubated at 37° C. in RPMI 1640 medium (mfd. by Gibco) containing 10% of fetal calf serum (mfd. by JRH Bioscience) treated at 56° C. for 30 minutes and then suspended in ASF104 medium (mfd. by Ajinomoto Co., Ltd.) in such a manner as to give a concentration of $5 \times 10^4$ cells/900 µl. Then the suspension was pipetted into a 6-well plate (mfd. by FALCON) at a ratio of 4.5 ml/well. To the suspension were added 0.5 ml portions of a 10 mg/ml solution of the freeze-dried degradation product of the sulfated-fucose-containing polysaccharide-F described in Example 19(6) dissolved in 30 mM Hepes buffer (pH 7) containing 120 mM of sodium chloride and treated with a filter followed by incubation at 37° C. in the presence of 5% of carbon dioxide. As a control, the above-mentioned buffer alone was added in the same amount and incubation was effected in the same manner. 22 and 46 hours after the initiation of the incubation, the viable cells were counted in accordance with the method described in "Soshiki Baiyo no Gijutsu" (second ed.), Asakura Shuppan, ed. by Nippon Soshiki Baiyo Gakkai, 26–28 (1990), namely, by the Trypan Blue staining method on a counting chamber.

As a result, it has been found out that the above-mentioned freeze-dried degradation product of the sulfated-fucose-containing polysaccharide-F induces the apoptosis of the HL-60 cells and thus lowers the cell growth rate.

Example 34

Human premyelocytic leukemia cells HL-60 were suspended in RPMI 1640 medium (mfd. by Gibco) containing 10% of fetal calf serum (mfd. by JRH Bioscience) treated at 56° C. for 30 minutes in such a manner as to give a concentration of $5 \times 10^4$ cells/900 µl. To six portions of this suspension were added 100 µl portions of a 10 mg/ml solutions of the sulfated-fucose-containing polysaccharide-F described in Example 18(2), F-Fd-1, F-Fd-2, F-Fd-3 and F-Fd-4 dissolved in 30 mM Hepes buffer (pH 7) containing 120 mM of sodium chloride and treated with a filter followed by incubation at 37° C. in the presence of 5% of carbon dioxide for 46 hours.

22 and 46 hours after the initiation of the incubation, the viable cells in the culture media were counted.

Separately, human premyelocytic leukemia cells HL-60 were suspended in ASF 104 medium (mfd. by Ajinomoto Co., Ltd.) in such a manner as to give a concentration of $5 \times 10^4$ cells/900 µl. To six portions of this suspension were added 100 µl portions of a 10 mg/ml solutions of the sulfated-fucose-containing polysaccharide-F, F-Fd-1, F-Fd-2, F-Fd-3 and F-Fd-4 dissolved in 30 mM Hepes buffer (pH 7) containing 120 mM of sodium chloride and treated with a filter followed by incubation at 37° C. in the presence of 5% of carbon dioxide for 40 hours.

16 and 40 hours after the initiation of the incubation, the viable cells in the culture media were counted.

The two types of the cells thus incubated were observed under a microscope to thereby examine the extent of the growth and the morphology of the cells.

As a result, all of the cells incubated in ASF 104 medium to which the sulfated-fucose-containing polysaccharide-F, F-Fd-1, F-Fd-2, F-Fd-3 and F-Fd-4 were added showed characteristics of apoptosis such as the shrinkage and fragmentation of the cells. In these cases, little increase in the viable cell count was observed or the cells were almost completely exterminated. In contrast, the cells incubated in the medium to which the buffer alone was added were increased almost thrice. In the cases of the cells incubated in RPMI1640 medium, on the other hand, all of the cells in the medium to which F-Fd-1, F-Fd-2, F-Fd-3 and F-Fd-4 were added showed characteristics of apoptosis such as the shrinkage and fragmentation of the cells. In these cases, the cells were almost completely exterminated. In contrast, the cells incubated in the medium to which the buffer alone was added were increased almost thrice, while the cells incubated in the medium to which the sulfated-fucose-containing polysaccharide-F was added were increased by about 2.5 times.

Based on these results, it has been found out that the sulfated-fucose-containing polysaccharide-F exerts a potent effect of inducing apoptosis on cancer cells in a serum-free medium, while F-Fd-1, F-Fd-2, F-Fd-3 and F-Fd-4 exert potent effects of inducing apoptosis on cancer cells in both of a serum-free medium and a serum-containing medium.

For the further confirmation, human premyelocytic leukemia cells HL-60 were suspended in RPMI 1640 medium (mfd. by Gibco) containing 10% of fetal calf serum (mfd. by JRH Bioscience) treated at 56° C. for 30 minutes in such a manner as to give a concentration of $5 \times 10^4$ cells/900 µl. To two portions of 9 ml of this suspension were added 1 ml portions of 30 mM Hepes buffer (pH 7) containing 120 mM of sodium chloride and a 10 mg/ml solution of F-Fd-4 dissolved in this buffer and treated by filtering. After incubating at 37° C. for 16 hours in the presence of 5% of carbon dioxide, the cells were separated from the supernatant by centrifugation.

The cells thus obtained were suspended in 20 µl of a 50 mM Tris hydrochloride buffer (pH 7.8) containing 10 mM of ethylenediaminetetraacetate and 0.5% of sodium lauroyl-sarcosinate. Then 1 µl of 10 mg/ml Ribonuclease A (mfd. by Sigma) was added thereto and the mixture was treated at 50° C. for 30 minutes. After adding 1 µl of 10 mg/ml of Proteinase K, the mixture was treated at 50° C. for 30 minutes. The cells thus treated were employed as a sample and electrophoresed in a 2% agarose gel under a constant voltage of 100 V. This gel was immersed in an ethidium bromide solution for 30 minutes and then the conditions of the DNA in the gel were examined by using a transilluminator. As a result, DNA ladders characteristic of apoptosis were observed therein. For the further confirmation, the above procedure was repeated using Actinomycin D known as a reagent inducing apoptosis as a substitute for the above-mentioned F-Fd-4. As a result, DNA ladders were observed similar to the case with the use of F-Fd-4.

Based on these results, it has been clarified that when the sulfated-fucose-containing polysaccharide-F is degraded with the endo-sulfated-fucose-containing polysaccharide degrading enzyme of the present invention, the effect thereof of inducing apoptosis on cancer cells is enhanced.

Example 35

Venous bloods were collected from a healthy female aged 21 and a healthy male aged 32 and diluted 2-fold with a solution containing, per liter of the solution, 100 mg of glucose, 0.74 mg of $CaCl_2 \cdot H_2O$, 19.92 mg of $MgCl_2$, 40.26 mg of KCl, 7371 mg of NaCl and 1,756.5 mg of Tris hydrochloride. Next, it was gently layered over twice as much a solution for separating lymphocytes (marketed from Dainippon Pharmaceutical Co., Ltd.) which had been preliminarily fed into a centrifugal tube and then centrifuged at 18 to 20° C. and 400×g for 30 minutes. After the completion of the centrifugation, the lymphocyte fraction in the upper layer of the solution for separating lymphocytes was taken up.

The normal lymphocytes thus obtained were added to a 24-well plate at a rate of $1.9 \times 10^5$ cells/well followed by the addition thereto of 1.8 ml portions of RPMI-1640 medium containing 10% of fetal calf serum (treated at 56° C. for 30 minutes) and 0.2 ml of 5 mg/ml of each of the sulfated-fucose-containing polysaccharides obtained in the above Examples and degradation products thereof. Then the lymphocytes were incubated at 37° C. As a control, physiological saline alone was added as a substitute for the sulfated-fucose-containing polysaccharide solution. After the initiation of the incubation, morphological changes and the viable count of the cells in each well were monitored under a microscope. As a result, no difference in the morphology of the cells was observed among the wells containing various sulfated-fucose-containing polysaccharides, those containing the degradation products thereof and the control well. Also, little difference was observed in the viable count. On the day 13, almost all of the cells were exterminated in every well. Based on these results, it has been found out that the sulfated-fucose-containing polysaccharides and degradation products thereof exert no toxicity on normal cells even at such a concentration as to potently induce apoptosis of cancer cells.

Example 36
Antitumor Effect of Sulfated-Fucose-Containing Polysaccharide-U on Solid Cancer:

A mouse solid cancer MethA ($4 \times 10^6$ cells/mouse) was subcutaneously injected into the abdomen of a male BALB/c mouse aged 8 weeks and weighing about 20 g. Subsequently, the sulfated-fucose-containing polysaccharide-U described in Example 6 was subcutaneously injected into the same site in a dose of 100 mg/kg/day for 10 days. Into the control group, physiological saline was injected in the same manner. 2 weeks thereafter, the cancer tissue formed in the abdomen of the mouse was taken out and weighed. Table 2 shows the results. Namely, the average tumor weight of the control group was 1.25 g, while that of the sulfated-fucose-containing polysaccharide-U-administration group was 0.28 g, thus showing a significant ($p<0.01$ to the control) antitumor effect. The inhibitory ratio was 77.6%.

TABLE 2

| Mouse (n) | Tumor weight (g) (mean ± SD) | Inhibitory ratio (%) |
|---|---|---|
| control (8) | 1.25 ± 0.10 | – |
| invention (8) | 0.28 ± 0.07 | 77.6 |

Example 37
Carcinostatic Effect of Sulfated-Fucose-Containing Polysaccharide:

(1) To the dorsal region of nineteen male Spragure-Dawley rats aged 6 weeks was subcutaneously administered 7.4 mg/kg of azoxymethane (mfd. by Nacalai Tesque). Subsequently, the chemical was subcutaneously administered to the dorsal region of the animal once a week till the 10th week. At the administration, azoxymethane was dissolved in a 0.1 M phosphate buffer (pH 6.5) containing 0.9% of sodium chloride and the concentration of the solution was controlled to give a dose of 100 µl each time.

Simultaneously with the first administration of azoxymethane, 70 ml of a hot water extract of *Kjellmaniella crassifolia* prepared in accordance with the method described in Example 1 was given to five rats among nineteen as described above everyday as drinking water till the 30th week. This hot water extract contained 2 mg/ml of the sulfated-fucose-containing polysaccharide mixture. Thus, the sulfated-fucose-containing polysaccharide mixture was orally administered everyday in a dose of 140 mg/kg/day.

To fourteen rats among nineteen as described above, not sulfated-fucose-containing polysaccharide but tap water was given as the drinking water and these animals were referred to as a control group.

Till the 30th week, the incidence of external ear focal cancer was observed in all of the fourteen rats among fourteen of the control group. In the group to which the sulfated-fucose-containing polysaccharide mixture was administered, in contrast thereto, one rat among five suffered from the cancer, thus showing a remarkable carcinostatic effect.

Till the 30th week, three rats died in the control group, while all animals survived in the group with the administration of the sulfated-fucose-containing polysaccharide mixture. On the 30th week, the average body weights of the control group and the group with the administration of the sulfated-fucose-containing polysaccharide mixture were respectively 716 g and 817 g. On the other hand, the average body weight of the group (five rats) to which no azoxymethane was administered was 788 g. That is to say, the body weight gain of the group with the administration of the sulfated-fucose-containing polysaccharide mixture was comparable to that of the group with no azoxymethane administration.

Next, four rats were selected from the control group and 40 ml of the above-mentioned hot water extract of *Kjellmaniella crassifolia* (containing 80 mg of the sulfated-fucose-containing polysaccharide mixture) was orally administered thereto everyday as the drinking water from the 30th week. On the 36th week, two rats among four showed remarkable shrinkage of the external ear focal cancer, thus showing the antitumor effect of the sulfated-fucose-containing polysaccharides.

As described above, it has been found out that the oral administration of the sulfated-fucose-containing polysaccharides is efficacious in preventing carcinogenesis caused by a carcinogenic chemical, preventing the inhibition of body weight gain due to a carcinogenic chemical and shrinking cancer tissues.

Example 38: Injection

The sulfated-fucose-containing polysaccharide mixture produced in Example 1 was dissolved in water for injection to give a 5% solution. This solution was packed in vials for freeze-drying in an amount of 50 mg/vial as the sulfated-fucose-containing polysaccharides followed by freeze-drying. Separately, 2 ml of physiological saline was added as a solvent.

Example 40: Injection

An injection of the following formulation was produced:

| | |
|---|---|
| sulfated-fucose-containing polysaccharide-U (Example 12) | 40 mg |
| physiological saline | q.s. |
| | 2 ml/ample. |

Similarly, another injection was prepared with the use of the sulfated-fucose-containing polysaccharide-F of Example 12.

Example 40: Tablet

A tablet of the following formulation was produced:

| | |
|---|---|
| sulfated-fucose-containing polysaccharide preparation (Example 1) | 10 mg |
| corn starch | 65 mg |
| carboxymethylcellulose | 20 mg |
| polyvinylpyrrolidone | 3 mg |
| magnesium stearate | 2 mg |
| | 100 mg/tablet. |

Example 41: Injection

F-Fd-1 was dissolved in water for injection to give a 5% solution. This solution was packed in vials for freeze-drying in an amount of 50 mg/vial in terms of the sulfated-fucose-containing polysaccharides followed by freeze-drying. Separately, 2 ml of physiological saline was added as a solvent.

Example 42: Injection

An injection of the following formulation was produced:

| | |
|---|---|
| freeze-dried degradation product of sulfated-fucose-containing polysaccharide-F (obtained in Example 19(6)) | 40 mg |
| physiological saline | q.s. |
| | 2 ml/ample. |

Example 43: Tablet

A tablet of the following formulation was produced:

| | |
|---|---|
| freeze-dried degradation product of sulfated-fucose-containing polysaccharide-F (obtained in Example 18(6) | 10 mg |
| corn starch | 65 mg |
| carboxymethylcellulose | 20 mg |
| polyvinylpyrrolidone | 3 mg |
| magnesium stearate | 2 mg |
| | 100 mg/tablet. |

Effects of the Invention

The present invention provides drugs which have the effects of inducing apoptosis on unnecessary or pathogenic cells, induce apoptosis of lesion cells in diseases in association with the abnormal proliferation of cells such as cancer and viral diseases and thus are useful in the prevention and treatment of various diseases. In digestive cancers such as colonic cancer and gastric cancer, in particular, the apoptosis of the cancer cells can be induced by orally administering the drugs of the present invention. Thus the drugs of the present invention, which contain as the active ingredient sulfated-fucose-containing polysaccharides and/or degradation products thereof originating in natural foods, are anticancer drugs highly suitable for digestive cancers. The drugs of the present invention further exert carcinostatic effects and thus can prevent carcinogenesis caused by carcinogenic chemicals. Because of originating in edible materials such as edible brown algae and sea cucumber, the drugs of the present invention can be supplied at a low price in a large amount and are excellent in the high safety. Furthermore, the daily intake of foods or drinks containing the sulfated-fucose-containing polysaccharides and/or degradation products thereof contributes to the maintenance and enhancement of human health. The present invention further provides a method for conveniently inducing apoptosis which is applicable to studies for revealing the mechanism of apoptosis, developing apoptosis induction inhibitors and the like.

The present invention further provides the sulfated-fucose-containing polysaccharide-U and degradation products thereof, which are substantially free from the sulfated-fucose-containing polysaccharide-F and from which highly reactive coloring matters have been eliminated, useful in the fields of sugar chain engineering, medicine and the like. Also, a method for efficiently producing the same is provided.

The present invention further provides the sulfated-fucose-containing polysaccharide-F and degradation products thereof, which are substantially free from the sulfated-fucose-containing polysaccharide-U and from which highly reactive coloring matters have been eliminated, useful in the fields of sugar chain engineering, medicine and the like. Also, a method for efficiently producing the same is provided.

The present invention furthermore provides an endo-sulfated-fucose-containing polysaccharide degrading enzyme, which is usable in analyzing the structure of the sulfated-fucose-containing polysaccharide-F, degrading the sulfated-fucose-containing polysaccharide-F and producing the degradation products of the sulfated-fucose-containing polysaccharide-F useful in the detection of the biological activities of the sulfated-fucose-containing polysaccharide-F; a process for producing this enzyme; and degradation products of the sulfated-fucose-containing polysaccharide-F having potent effects of inducing apoptosis of cancer cells which are obtained by using this enzyme.

Owing to the present invention, the endo-sulfated-fucose-containing polysaccharide-F degrading enzyme, which cannot be produced in a stable state by the conventional methods, can be produced in a highly stable state in the presence of calcium ions. According to the present invention, furthermore, the endo-sulfated-fucose-containing polysaccharide degrading enzyme can act very efficiently in the presence of calcium ions.

What is claimed is:

1. An apoptosis inducer comprising (a) as an active ingredient, a sulfated-fucose-containing polysaccharide and/or degradation product(s) thereof having an apoptosis inducing activity, wherein said sulfated-fucose-containing polysaccharide (1) contains uronic acid, and (2) can be degraded by a fucoidanase produced by Flavobacterium sp. SA-0082 (FERM BP-5402) to form one or more compounds having the following formulae (I), (II) or (III):

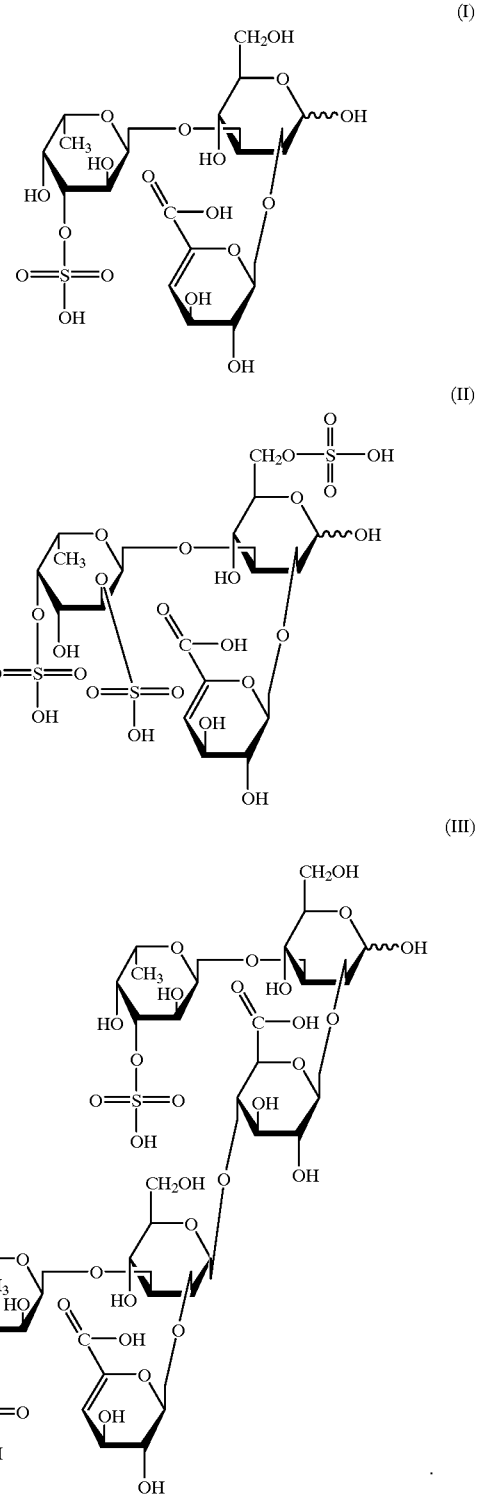

and (b) pharmaceutically acceptable carrier.

2. The apoptosis inducer as set forth in claim 1, which comprises said degradation product(s) of said sulfated-fucose-containing polysaccharide.

3. The apoptosis inducer as set forth in claim 2, wherein said degradation product(s) is one or more compound(s) having the following formulae (I), (II) or (III):

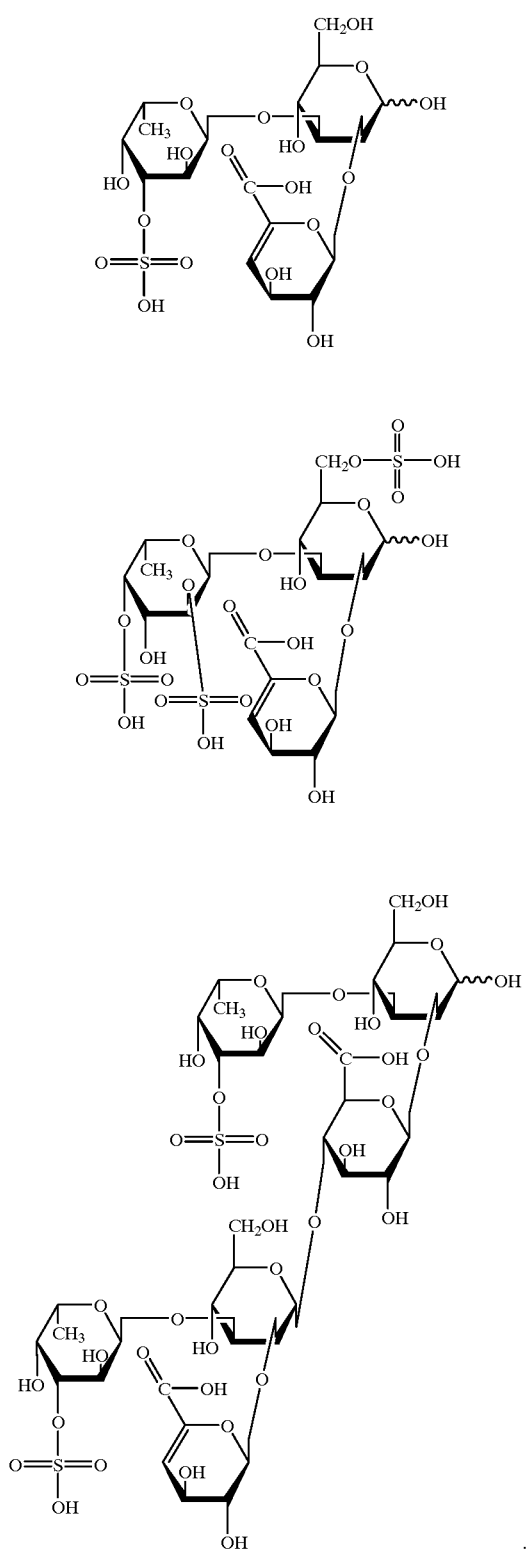

4. The apoptosis inducer as set forth in claim 1, wherein said degradation product(s)

(1) is obtained by treating said sulfated-fucose-containing polysaccharide with an endo-sulfated-fucose-containing polysaccharide degrading enzyme produced by Flavobacterium sp. SA-0082 (FERM BP-5402), and (2) has a molecular weight of 100,000 or greater.

5. The apoptosis inducer as set forth in claim 1, wherein said degradation product(s)

(1) is obtained by incubating Flavobacterium sp. SA-0082 (FERM BP-5402) in the presence of said sulfated-fucose-containing polysaccharide, and (2) has a molecular weight of 100,000 or greater.

6. The apoptosis inducer as set forth in claim 1, wherein said degradation product(s) is obtained by degrading said sulfated-fucose-containing polysaccharide with an acid.

7. The apoptosis inducer as set forth in claim 6, wherein said degradation product was subjected to molecular weight fractionation.

8. A method for inducing apoptosis which comprises administering, as an active ingredient, a sulfated-fucose-containing polysaccharide and/or degradation product(s) thereof having an apoptosis inducing activity, to a cell to induce apoptosis, wherein said sulfated-fucose-containing polysaccharide (1) contains uronic acid, and (2) can be degraded by a fucoidanase produced by Flavobacterium sp. SA-0082 (FERM BP-5402) to form one or more compounds having the following formulae (I), (II) or (III):

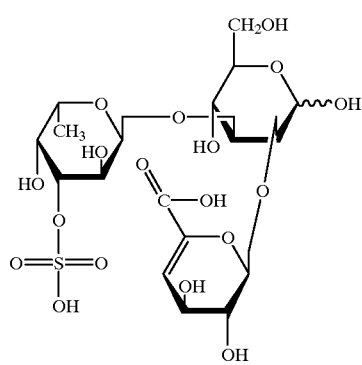

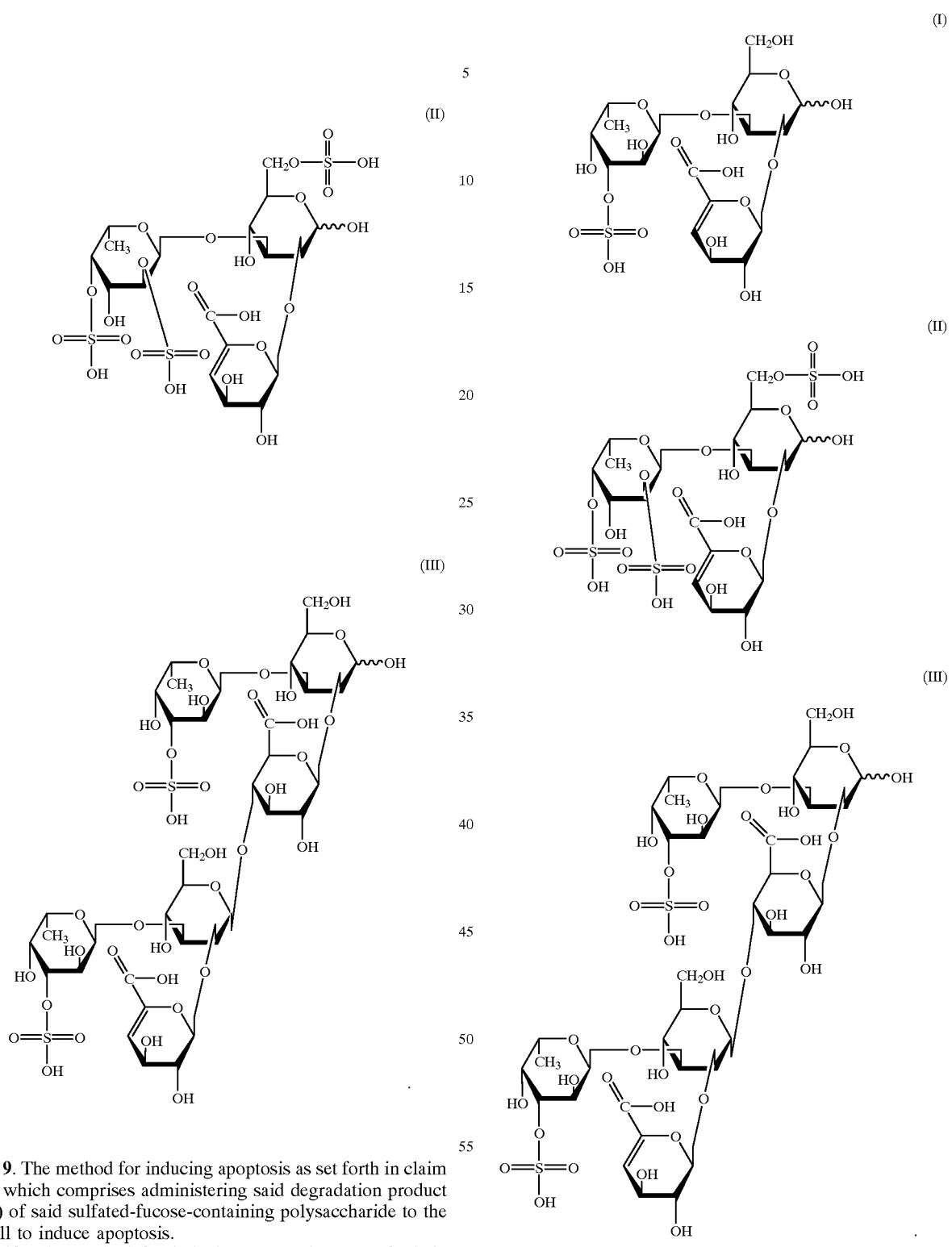
9. The method for inducing apoptosis as set forth in claim 8, which comprises administering said degradation product(s) of said sulfated-fucose-containing polysaccharide to the cell to induce apoptosis.
10. The method for inducing apoptosis as set forth in claim 9, wherein said degradation product(s) is one or more compound(s) having the following formulae (I), (II) or (III):

11. The method for inducing apoptosis as set forth in claim 8, wherein said degradation product(s)

(1) is obtained by treating said sulfated-fucose-containing polysaccharide with an endo-sulfated-fucose-containing polysaccharide degrading enzyme produced by Flavobacterium sp. SA-0082 (FERM BP-5402), and (2) has a molecular weight of 100,000 or greater.

12. The method for inducing apoptosis as set forth in claim 8, wherein said degradation product(s)

(1) is obtained by incubating Flavobacterium sp. SA-0082 (FERM BP-5402) in the presence of said sulfated-fucose-containing polysaccharide, and (2) has a molecular weight of 100,000 or greater.

13. The method for inducing apoptosis as set forth in claim 8, wherein said degradation product(s) is obtained by degrading said sulfated-fucose-containing polysaccharide with an acid.

14. The method for inducing apoptosis as set forth in claim 13, wherein said degradation product(s) was subjected to molecular weight fractionation.

15. A sulfated-fucose-containing polysaccharide; which (1) contains uronic acid, and (2) can be degraded by a fucoidanase produced by Flavobacterium sp. SA-0082 (FERM BP-5402) to form one or more compounds having the following formulae (I), (II) or (III):

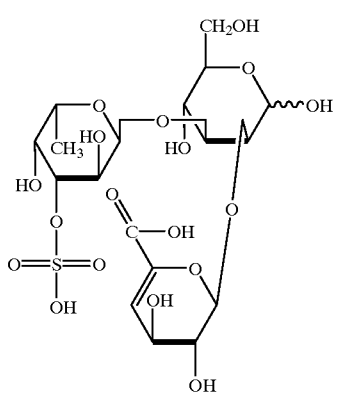

(I)

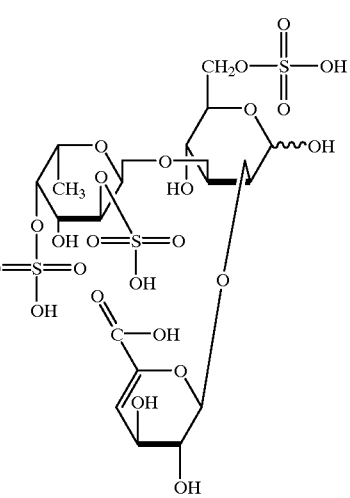

(II)

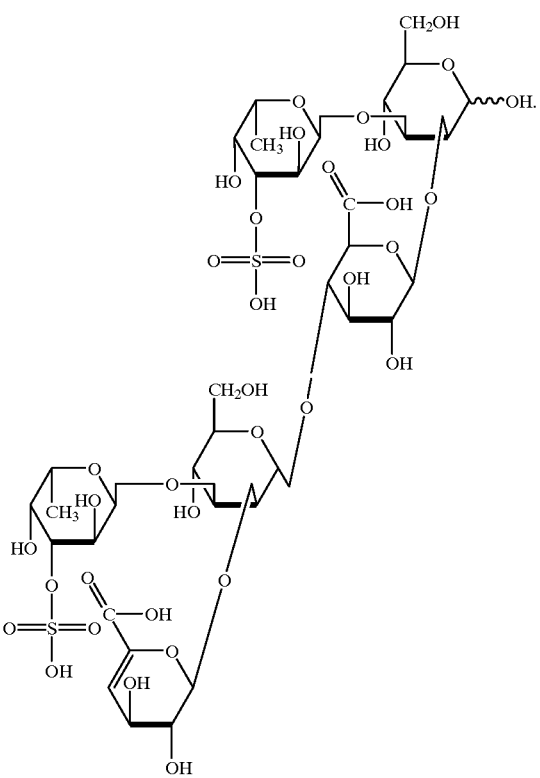

(III)

16. A process for producing the sulfated-fucose-containing polysaccharide as set forth in claim 15, which comprises treating a mixture of sulfated-fucose-containing polysaccharides with a chemical which aggregates acidic polysaccharides in the presence of salts, to extract the sulfated-fucose containing polysaccharides.

17. The process for producing the sulfated-fucose-containing polysaccharide as set forth in claim 16, wherein the chemical is cetylpyridinium chloride.

18. A process for producing the sulfated-fucose-containing polysaccharide as set forth in claim 15, which comprises treating a mixture of sulfated-fucose-containing polysaccharides with an anion exchange resin in the presence of a divalent cation to extract the sulfated-fucose containing polysaccharides.

19. A process for producing the sulfated-fucose-containing polysaccharide as set forth in claim 15, which comprises extracting the sulfated-fucose-containing polysaccharide from a mixture of sulfated-fucose-containing polysaccharides and removing coloring matters contained in the sulfated-fucose-containing polysaccharides with a polysaccharide substance or a substance having an anion exchange group.

20. The process for producing the sulfated-fucose-containing polysaccharide as set forth in claim 19, wherein the polysaccharide substance is a polysaccharide resin.

21. The process for producing the sulfated-fucose-containing polysaccharide as set forth in any of claims 16–20, wherein the sulfated-fucose-containing polysaccharide mixture is obtained by a method comprising extracting sulfated-fucose-containinge polysaccharide from marine algae with acetate and calcium ions.

* * * * *